United States Patent [19]

Takagi et al.

[11] Patent Number: 5,608,109
[45] Date of Patent: Mar. 4, 1997

[54] INSECTICIDAL HYDRAZINE DERIVATIVES

[75] Inventors: Kazuhiro Takagi; Tetsuji Ohshima, both of Nishinomiya; Nobuyoshi Hasegawa, Osaka; Chiaki Katoh, Kawachinagano; Atsushi Kanaoka, Hashimoto; Hideo Kanno, Ibaraki, all of Japan

[73] Assignee: Nihon Nohyaku Co., Ltd., Tokyo, Japan

[21] Appl. No.: 350,462

[22] Filed: Dec. 7, 1994

[30] Foreign Application Priority Data

Dec. 8, 1993 [JP] Japan ..................... 5-340886

[51] Int. Cl.$^6$ ............. C07C 281/14; C07C 309/64; C07C 309/71; C07C 309/72; A01N 47/34
[52] U.S. Cl. ............. 564/36; 544/168; 544/406; 546/245; 558/388; 564/81; 564/149
[58] Field of Search ............... 564/36, 81, 149; 514/583, 590, 237.5, 255, 330, 520; 544/168, 406; 546/245; 550/388

[56] References Cited

U.S. PATENT DOCUMENTS

| | | | |
|---|---|---|---|
| 3,558,654 | 1/1971 | Bamford et al. | 564/36 X |
| 3,712,914 | 1/1973 | Tilles | 564/36 X |
| 3,753,680 | 8/1973 | Tilles | 564/36 X |
| 4,606,987 | 8/1986 | Matsuura et al. | 564/36 X |
| 5,118,830 | 6/1992 | Findeisen et al. | 558/417 |
| 5,182,303 | 1/1993 | Daub et al. | 514/583 |
| 5,376,685 | 12/1994 | Stanek et al. | 514/583 |
| 5,395,855 | 3/1995 | Stanek et al. | 514/632 |

FOREIGN PATENT DOCUMENTS

| | | | |
|---|---|---|---|
| 0462456 | 12/1991 | European Pat. Off. | 564/76 |
| 0486937 | 5/1992 | European Pat. Off. | 564/76 |
| 5-17428 | 1/1993 | Japan | 564/76 |
| 5-4958 | 1/1993 | Japan | 564/76 |
| 5-32603 | 2/1993 | Japan | 564/76 |
| 5-262712 | 10/1993 | Japan | 564/26 |
| 7-53501 | 2/1995 | Japan | 564/76 |
| 9206076 | 4/1992 | WIPO | 564/76 |
| 94-06758 | 3/1994 | WIPO | 564/36 |
| 94-08954 | 4/1994 | WIPO | 564/36 |

OTHER PUBLICATIONS

Chemical Abstracts, vol. 54, No. 5, 10 Mar. 1960, Columbus, Ohio, US; abstract No. 4482i, C. Runti, L. Sindellari, pp. 877–893.

Chemical Abstracts, vol. 103, No. 11, 16 Sep. 1985, Columbia, Ohio, US; abstract No. 88088p, E. Occelli et al., p. 629 & Farmaco, Ed. Sci., vol. 40, No. 2, 1985, pp. 86–101.

Chemical Abstracts, vol. 99, No. 21, 21 Nov. 1983, Columbus, Ohio, US; abstract No. 175414j, Chin, Hsiao–Ling M., p. 588.

Chemical Abstracts, vol. 81, , No. 23, 9 Dec. 1974, Columbus, Ohio, US; abstract No. 151744u, U. Oyman, p. 490 & Chim. Acta. Turc., vol. 2, No. 1, 1974, pp. 65–81.

Chemical Abstracts, vol. 79, No. 13, 1 Oct. 1973, Columbus, Ohio, US; abstract No. 78571w, U. Petersen, H. Heitzer, p. 496 & Justus Liebigs and Chem., No. 5–6, 1973, pp. 944–960.

Chemical Abstracts, vol. 55, No. 22, 30 Oct. 1961, Columbus, Ohio, US; abstract No. 22215a, E. Bulka et al. & Chem. Ber., vol. 94, 1961, pp. 1122–1126.

Chemical Abstracts, vol. 54, No. 12, 25 Jun. 1960, Columbia, Ohio, US; abstract No. 11980c, E. N. Zil'Berman, A. E. Kulikova & Zhur. Obshchei Khim., vol. 29, 1959, pp. 3039–3041.

Chemical Abstracts, vol. 83, No. 15, 13 Oct. 1975, Columbus, Ohio; abstract No. 126292d, B. Prescott p. 40 & Int. J. Clin. Pharmacol. Biopharm., vol. 11, No. 4, 1975, pp. 332–335.

*Primary Examiner*—Floyd D. Higel
*Attorney, Agent, or Firm*—Cushman Darby & Cushman IP Group of Pillsbury Madison & Sutro LLP

[57] ABSTRACT

The present invention relates to a hydrazine derivative represented by the formula (I):

$$Ar^1-A-\underset{\underset{R^1}{|}}{\overset{\overset{W}{\|}}{C}}-N-Ar^2$$

(wherein each of $Ar^1$ and $Ar^2$ is a substituted or unsubstituted phenyl group, a substituted or unsubstituted heteroaryl group, or the like, $R^1$ is an alkyl group or the like, and A is a divalent radical having —C=N—N— or —CH—NH—N— as a fundamental skeleton), which is a useful compound as an agricultural and horticultural insecticide.

4 Claims, No Drawings

INSECTICIDAL HYDRAZINE DERIVATIVES

BACKGROUND OF THE INVENTION

Field of the Invention

The present invention relates to hyrazine derivatives represented by the following general formula (I) and agricultural and horticultural insecticides:

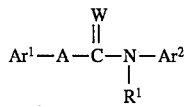

wherein $Ar^1$ and $Ar^2$, which may be the same or different, are unsubstituted phenyl groups; substituted phenyl groups having 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which may be the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which may be the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups; unsubstituted 5- or 6-membered heteroaryl groups having 1 to 3 heteroatoms which may be the same or different and are selected from the group consisting of nitrogen atom, oxygen atom and sulfur atom; or substituted 5- or 6-membered heteroaryl groups which are the same as the above unsubstituted 5- or 6-membered heteroaryl groups, except for having as the substituent(s) one or more halogen atoms or $(C_{1-6})$alkyl groups, which may be the same or different, $R^1$ is a hydrogen atom, a $(C_{1-6})$alkyl group, a $(C_{2-6})$alkenyl group or a $(C_{2-6})$alkynyl group, A is

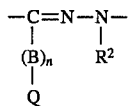

[wherein $R^2$ is a hydrogen atom, a $(C_{1-6})$alkyl group, a $(C_{2-6})$alkenyl group or a $(C_{2-6})$alkynyl group, B is an unsubstituted and linear or branched $(C_{1-6})$alkylene group, a substituted and linear or branched $(C_{1-6})$alkylene group having one or more halogen atoms or $(C_{1-6})$alkoxy groups as the substituent(s), an unsubstituted and linear or branched $(C_{2-6})$alkenylene group, a substituted and linear or branched $(C_{2-6})$alkenylene group having one or more halogen atoms or $(C_{1-6})$alkoxy groups as the substituent(s), an unsubstituted and linear or branched $(C_{2-6})$alkynylene group, or a substituted and linear or branched $(C_{2-6})$alkynylene group having one or more halogen atoms or $(C_{1-6})$alkoxy groups as the substituent(s), the branched alkylene, alkenylene or alkynylene group being able to form a ring having 3 to 7 carbon atoms by bonding of substituents on the same carbon atom to each other, n is zero or 1, Q is a cyano group; a nitro group; a $(C_{2-6})$alkenyl group; a $(C_{2-6})$alkynyl group; an unsubstituted phenyl$(C_{2-6})$alkenyl group; a substituted phenyl$(C_{2-6})$alkenyl group having on the ring 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which may be the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which may be the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups; an unsubstituted phenyl$(C_{2-6})$alkynyl group; a substituted phenyl$(C_{2-6})$alkynyl group having on the ring 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which may be the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which may be the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups; a $(C_{2-6})$alkynyl$(C_{2-6})$alkenyl group; a $(C_{2-6})$alkenyl$(C_{2-6})$alkynyl group;

—$OR^3$ (wherein $R^3$ is a hydrogen atom; a $(C_{1-6})$alkyl group; a halo$(C_{1-6})$alkyl group; a $(C_{1-6})$alkoxy$(C_{1-6})$alkyl group; a $(C_{1-6})$alkylthio$(C_{1-6})$alkyl group; a $(C_{1-6})$alkylsulfinyl$(C_{1-6})$alkyl group; a $(C_{1-6})$alkylsulfonyl$(C_{1-6})$alkyl group; a halo$(C_{1-6})$alkylthio$(C_{1-6})$alkyl group; a halo$(C_{1-6})$alkylsulfinyl$(C_{1-6})$alkyl group; a halo$(C_{1-6})$alkylsulfonyl$(C_{1-6})$alkyl group; a cyano$(C_{1-6})$alkyl group; a $(C_{3-6})$cycloalkyl group; a $(C_{3-6})$cycloalkyl$(C_{1-6})$alkyl group; a $(C_{1-6})$alkoxycarbonyl$(C_{1-6})$alkyl group; a $(C_{1-6})$alkylcarbonyl$(C_{1-6})$alkyl group; a $(C_{1-6})$alkylcarbonyl group; an unsubstituted amino$(C_{1-6})$alkyl group; a substituted amino$(C_{1-6})$alkyl group having one or two substituents which may be the same or different and are selected from the group consisting of $(C_{1-6})$alkyl groups and $(C_{1-6})$alkylcarbonyl groups; an unsubstituted carbamoyl$(C_{1-6})$alkyl group; a substituted carbamoyl$(C_{1-6})$alkyl group having one or two substituents which may be the same or different and are selected from $(C_{1-6})$alkyl groups; an unsubstituted phenyl group; a substituted phenyl group having 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which may be the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which may be the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups; an unsubstituted phenyl$(C_{1-6})$alkyl group; a substituted phenyl$(C_{1-6})$alkyl group having on the ring 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which may be the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which may be the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups; an unsubstituted phenyl$(C_{2-6})$alkenyl group; a substituted phenyl$(C_{2-6})$alkenyl group having on the ring 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which may be the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which may be the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups; an unsubstituted phenyl$(C_{2-6})$alkynyl group; a substituted phenyl$(C_{2-6})$alkynyl group having on the ring 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which may be the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which may be the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups; a 5- or 6-membered heteroaryl group having 1 to 3 heteroatoms which may be the same or different and are selected from the group consisting of oxygen atom, sulfur atom and nitrogen atom; or a 5- or 6-membered heteroaryl$(C_{1-6})$alkyl group having 1 to 3 heteroatoms which may be the same or different and are selected from the group consisting of oxygen atom, sulfur atom and nitrogen atom);

$$-(SO_2)_m R^3$$

(wherein $R^3$ is as defined above, and m is zero, 1 or 2);

$$-COOR^4$$

(wherein $R^4$ is a hydrogen atom, a $(C_{1-6})$alkyl group, a halo$(C_{1-6})$alkyl group, a $(C_{2-6})$alkenyl group, a halo$(C_{2-6})$alkenyl group, a $(C_{2-6})$alkynyl group or a halo$(C_{2-6})$alkynyl group);

$$-\overset{O}{\underset{\|}{P}}(OR^4)_2$$

(wherein $R^4$ is as defined above);

$$-CON(R^5)R^6$$

(wherein $R^5$ is a hydrogen atom; a $(C_{1-6})$alkyl group; a $(C_{2-6})$alkenyl group; a $(C_{2-6})$alkynyl group; an unsubstituted phenyl group; or a substituted phenyl group having 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which may be the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which may be the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups, and $R^6$ is a hydrogen atom; a $(C_{1-6})$alkyl group; a halo$(C_{1-6})$alkyl group; a $(C_{2-6})$alkenyl group; a $(C_{2-6})$alkynyl group; a $(C_{1-6})$alkoxy$(C_{1-6})$alkyl group; a halo$(C_{1-6})$alkoxy$(C_{1-6})$alkyl group; a $(C_{1-6})$alkylthio$(C_{1-6})$alkyl group; a halo$(C_{1-6})$alkylthio$(C_{1-6})$alkyl group; a $(C_{1-6})$alkylsulfinyl$(C_{1-6})$alkyl group; a halo$(C_{1-6})$alkylsulfinyl$(C_{1-6})$alkyl group; a $(C_{1-6})$alkylsulfonyl$(C_{1-6})$alkyl group; a halo$(C_{1-6})$alkylsulfonyl$(C_{1-6})$alkyl group; a cyano$(C_{1-6})$alkyl group; a hydroxy$(C_{1-6})$alkyl group; a $(C_{3-6})$cycloalkyl group; a $(C_{3-6})$cycloalkyl$(C_{1-6})$alkyl group; a $(C_{1-6})$alkoxycarbonyl$(C_{1-6})$alkyl group; a $(C_{1-6})$alkylcarbonyl$(C_{1-6})$alkyl group; a carbamoyl$(C_{1-6})$alkyl group; a substituted carbamoylalkyl group having one or two substituents which may be the same or different and are selected from $(C_{1-6})$alkyl groups; an unsubstituted amino$(C_{1-6})$alkyl group; a substituted amino$(C_{1-6})$alkyl group having one or two substituents which may be the same or different and are selected from the group consisting of $(C_{1-6})$alkyl groups and $(C_{1-6})$alkylcarbonyl groups; or a 5- or 6-membered heteroaryl$(C_{1-6})$alkyl group having 1 to 3 heteroatoms which may be the same or different and are selected from the group consisting of oxygen atom, sulfur atom and nitrogen atom, $R^5$ and $R^6$ being able to be taken together to represent a $(C_{4-6})$alkylene group which may contain, between adjacent carbon atoms of the carbon chain, —O—, —(SO)$_m$— (wherein m is as defined above), or —N(R$^7$)— (wherein R$^7$ has the meaning described below), and said alkylene group being able to have one or more substituents which may be the same or different and are selected from the group consisting of (C$_{1-6}$)alkyl groups, (C$_{1-6}$)alkoxycarbonyl groups and phenyl group);

—SO$_2$N(R$^5$)(R$^6$)

(wherein R$^5$ and R$^6$ are as defined above);

—N(R$^7$)R$^8$ (wherein R$^7$ and R$^8$, which may be the same or different, are hydrogen atoms; formyl groups; cyano groups; (C$_{1-6}$)alkyl groups; (C$_{2-6}$)alkenyl groups; (C$_{2-6}$)alkynyl groups; (C$_{1-6}$)alkylcarbonyl groups; halo(C$_{1-6}$)alkylcarbonyl groups; (C$_{1-6}$)alkoxycarbonyl groups; halo(C$_{1-6}$)alkoxycarbonyl groups; (C$_{3-6}$)cycloalkylcarbonyl group; phenoxycarbonyl groups; (C$_{1-6}$)alkylsulfonyl groups; unsubstituted carbamoyl groups; substituted carbamoyl groups having as the substituent(s) one or two (C$_{1-6}$)alkyl groups which may be the same or different; unsubstituted carbamoyl(C$_{1-6}$)alkyl groups; substituted carbamoyl(C$_{1-6}$)alkyl groups having as the substituent(s) one or two (C$_{1-6}$)alkyl groups which may be the same or different; unsubstituted thiocarbamoyl groups; substituted thiocarbamoyl groups having as the substituent(s) one or two (C$_{1-6}$)alkyl groups which may be the same or different; unsubstituted sulfamoyl groups; substituted sulfamoyl groups having as the substituent(s) one or two (C$_{1-6}$)alkyl groups which may be the same or different; unsubstituted (C$_{1-6}$)alkoxycarboimidoyl groups; substituted (C$_{1-6}$)alkoxycarboimidoyl groups having (C$_{1-6}$)alkyl group as the substituent; unsubstituted (C$_{1-6}$)alkylthiocarboimidoyl groups; substituted (C$_{1-6}$)alkylthiocarboimidoyl groups having (C$_{1-6}$)alkyl group as the substituent; unsubstituted phenyl groups; substituted phenyl groups having 1 to 5 substituents which may be the same or different and are selected from the group consisting of halogen atoms, cyano group, nitro group, (C$_{1-6}$)alkyl groups, halo(C$_{1-6}$)alkyl groups, (C$_{1-6}$)alkoxy groups, halo(C$_{1-6}$)alkoxy groups, (C$_{1-6}$)alkylthio groups, halo(C$_{1-6}$)alkylthio groups, (C$_{1-6}$)alkylsulfinyl groups, halo(C$_{1-6}$)alkylsulfinyl groups, (C$_{1-6}$)alkylsulfonyl groups, halo(C$_{1-6}$)alkylsulfonyl groups, (C$_{1-6}$)alkoxycarbonyl groups, unsubstituted phenoxy group, substituted phenoxy groups having 1 to 5 substituents which may be the same or different and are selected from the group consisting of halogen atoms, (C$_{1-6}$)alkyl groups and halo(C$_{1-6}$)alkyl groups, unsubstituted pyridyloxy group, substituted pyridyloxy groups having 1 to 4 substituents which may be the same or different and are selected from the group consisting of halogen atoms, (C$_{1-6}$)alkyl groups and halo(C$_{1-6}$)alkyl groups, dioxy(C$_{1-3}$)alkylene groups, and dioxyhalo(C$_{1-3}$)alkylene groups; unsubstituted phenyl(C$_{1-6}$)alkyl groups; substituted phenyl(C$_{1-6}$)alkyl groups having on the ring 1 to 5 substituents which may be the same or different and are selected from the group consisting of halogen atoms, cyano group, nitro group, (C$_{1-6}$)alkyl groups, halo(C$_{1-6}$)alkyl groups, (C$_{1-6}$)alkoxy groups, halo(C$_{1-6}$)alkoxy groups, (C$_{1-6}$)alkylthio groups, halo(C$_{1-6}$)alkylthio groups, (C$_{1-6}$)alkylsulfinyl groups, halo(C$_{1-6}$)alkylsulfinyl groups, (C$_{1-6}$)alkylsulfonyl groups, halo(C$_{1-6}$)alkylsulfonyl groups, (C$_{1-6}$)alkoxycarbonyl groups, unsubstituted phenoxy group, substituted phenoxy groups having 1 to 5 substituents which may be the same or different and are selected from the group consisting of halogen atoms, (C$_{1-6}$)alkyl groups and halo(C$_{1-6}$)alkyl groups, unsubstituted pyridyloxy group, substituted pyridyloxy groups having 1 to 4 substituents which may be the same or different and are selected from the group consisting of halogen atoms, (C$_{1-6}$)alkyl groups and halo(C$_{1-6}$)alkyl groups, dioxy(C$_{1-3}$)alkylene groups, and dioxyhalo(C$_{1-3}$)alkylene groups; unsubstituted phenylcarbamoyl groups; substituted phenylcarbamoyl groups having on the ring 1 to 5 substituents which may be the same or different and are selected from the group consisting of halogen atoms, cyano group, nitro group, (C$_{1-6}$)alkyl groups, halo(C$_{1-6}$)alkyl groups, (C$_{1-6}$)alkoxy groups, halo(C$_{1-6}$)alkoxy groups, (C$_{1-6}$)alkylthio groups, halo(C$_{1-6}$)alkylthio groups, (C$_{1-6}$)alkylsulfinyl groups, halo(C$_{1-6}$)alkylsulfinyl groups, (C$_{1-6}$)alkylsulfonyl groups, halo(C$_{1-6}$)alkylsulfonyl groups, (C$_{1-6}$)alkoxycarbonyl groups, unsubstituted phenoxy group, substituted phenoxy groups having 1 to 5 substituents which may be the same or different and are selected from the group consisting of halogen atoms, (C$_{1-6}$)alkyl groups and halo(C$_{1-6}$)alkyl groups, unsubstituted pyridyloxy group, substituted pyridyloxy groups having 1 to 4 substituents which may be the same or different and are selected from the group consisting of halogen atoms, (C$_{1-6}$)alkyl groups and halo(C$_{1-6}$)alkyl groups, dioxy(C$_{1-3}$)alkylene groups, and dioxyhalo(C$_{1-3}$)alkylene groups; unsubstituted phenylcarbonyl groups; substituted phenylcarbonyl groups having on the ring 1 to 5 substituents which may be the same or different and are selected from the group consisting of halogen atoms, cyano group, nitro group, (C$_{1-6}$)alkyl groups, halo(C$_{1-6}$)alkyl groups, (C$_{1-6}$)alkoxy groups, halo(C$_{1-6}$)alkoxy groups, (C$_{1-6}$)alkylthio groups, halo(C$_{1-6}$)alkylthio groups, (C$_{1-6}$)alkylsulfinyl groups, halo(C$_{1-6}$)alkylsulfinyl groups, (C$_{1-6}$)alkylsulfonyl groups, halo(C$_{1-6}$)alkylsulfonyl groups, (C$_{1-6}$)alkoxycarbonyl groups, unsubstituted phenoxy group, substituted phenoxy groups having 1 to 5 substituents which may be the same or different and are selected from the group consisting of halogen atoms, (C$_{1-6}$)alkyl groups and halo(C$_{1-6}$)alkyl groups, unsubstituted pyridyloxy group, substituted pyridyloxy groups having 1 to 4 substituents which may be the same or different and are selected from the group consisting of halogen atoms, (C$_{1-6}$)alkyl groups and halo(C$_{1-6}$)alkyl groups, dioxy(C$_{1-3}$)alkylene groups, and dioxyhalo(C$_{1-3}$)alkylene groups; unsubstituted phenylsulfonyl groups; or substituted phenylsulfonyl groups having on the ring 1 to 5 substituents which may be the same or different and are selected from the group consisting of halogen atoms, cyano group, nitro group, (C$_{1-6}$)alkyl groups, halo(C$_{1-6}$)alkyl groups, (C$_{1-6}$)alkoxy groups, halo(C$_{1-6}$)alkoxy groups, (C$_{1-6}$)alkylthio groups, halo(C$_{1-6}$)alkylthio groups, (C$_{1-6}$)alkylsulfinyl groups, halo(C$_{1-6}$)alkylsulfinyl groups, (C$_{1-6}$)alkylsulfonyl groups, halo(C$_{1-6}$)alkylsulfonyl groups, (C$_{1-6}$)alkoxycarbonyl groups, unsubstituted phenoxy group, substituted phenoxy groups having 1 to 5 substituents which may be the same or different and are selected from the group consisting of halogen atoms, (C$_{1-6}$)alkyl groups and halo(C$_{1-6}$)alkyl groups, unsubstituted pyridyloxy group, substituted pyridyloxy groups having 1 to 4 substituents which may be the same or different and are selected from the group consisting of halogen atoms, (C$_{1-6}$)alkyl groups and halo(C$_{1-6}$)alkyl groups, dioxy(C$_{1-3}$)alkylene groups, and dioxyhalo(C$_{1-3}$)alkylene groups);

—C(R$^9$)=NOR$^4$ (wherein R$^4$ is as defined above, and R$^9$ is a hydrogen atom, a (C$_{1-6}$)alkyl group, a halo(C$_{1-6}$)alkyl group, an unsubstituted phenyl group, or a substituted phenyl group having 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups);

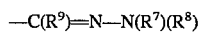

(wherein $R^7$, $R^8$ and $R^9$ are as defined above); or

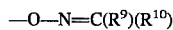

(wherein $R^9$ is as defined above, and $R^{10}$ is a hydrogen atom, a $(C_{1-6})$alkyl group, a halo$(C_{1-6})$alkyl group, an unsubstituted phenyl group, or a substituted phenyl group having 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups)],

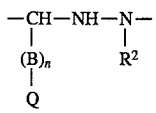

[wherein $R^2$, B, Q and n are as defined above],

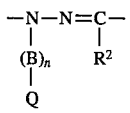

[wherein $R^2$, B, Q and n are as defined above], or

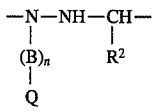

[wherein $R^2$, B, Q and n are as defined above], and W is an oxygen atom or a sulfur atom. More particularly, the hydrazine derivatives of the general formula (I) of the present invention include hydrazine derivatives represented by the following general formulas (I-1), (I-2), (I-3) and (I-4).

General formula (I-1):

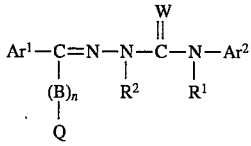 (I-1)

General formula (I-2):

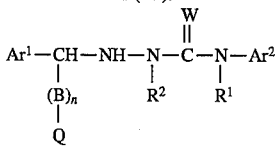 (I-2)

General formula (I-3):

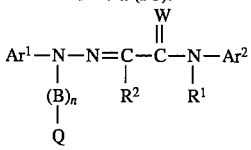 (I-3)

General formula (I-4):

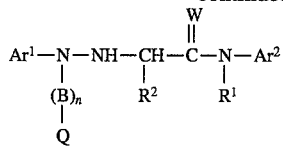 (I-4)

wherein $Ar^1$, $Ar^2$, $R^1$, $R^2$, B, n, Q and W are as defined above.

In the definition of the hydrazine derivatives of the general formula (I) of the present invention, the term "$(C_{1-6})$alkyl group", for example, means a linear or branched alkyl group having 1 to 6 carbon atoms, such as methyl, ethyl, n-propyl, i-propyl, n-butyl, i-butyl, s-butyl, t-butyl, n-pentyl, n-hexyl or the like. The prefix "halo" is used for expressing that a group has as its substituent(s) one or more halogen atoms which may be the same or different and are selected from chlorine, bromine, iodine and fluorine atoms. The term "haloalkyl group" means a substituted alkyl group having as the substituent(s) one or more halogen atoms which may be the same or different and are selected from the group consisting of chlorine atom, bromine atom, iodine atom and fluorine atom. The term "heteroaryl" in "heteroaryl group" or "heteroarylalkyl group" means a 5- to 6-membered ring having 1 to 3 heteroatoms which may be the same or different and are selected from the group consisting of oxygen atom, hydrogen atom and nitrogen atom, for example, heterocyclic groups such as furyl group, thienyl group, oxazole group, thiazole group, pyrazole group, imidazole group, pyridine group, etc.

The hydrazine derivatives of the general formulas (I-1) and (I-3) of the present invention have geometrical isomers, i.e., E-form and Z-form. The present invention also includes the E-form, the Z-form, and mixtures thereof. The hydrazine derivatives of the general formulas (I-2) and (I-4) have optical isomers, i.e., R-form and S-form. The present invention also includes the R-form, the S-form, and mixtures thereof.

Of the hydrazine derivatives of the general formula (I), compounds having a preferable structure are the hydrazine derivatives of the general formula (I-1). As the substituents of the hydrazine derivatives of the general formula (I-1), $Ar^1$ and $Ar^2$ are preferably unsubstituted phenyl groups or substituted phenyl groups having 1 to 3 substituents which may be the same or different and are selected from the group consisting of halogen atoms, cyano group, nitro group, alkyl groups, haloalkyl groups, alkoxy groups and haloalkoxy groups. $R^1$ and $R^2$, which may be the same or different, are preferably hydrogen atoms, or methyl groups. B is preferably a methylene, a ethylene or a propylene group, or n is preferably zero.

Q is preferably a substituent such as cyano group, $-OR^3$, $-S(O)_mR^3$, $-COOR^4$, $-CON(R^5)(R^6)$, or $N(R^7)(R^8)$.

RELATED ART

Japanese Patent Unexamined Publication Nos. 5-4958, 5-17428, 5-32603 and 5-262712 and WO92/06076, etc. disclose hydrazines similar to those of the present inventions and discloses them as effective as insecticides.

SUMMARY OF THE INVENTION

The present inventors earnestly investigated for developing a novel agricultural and horticultural insecticide and consequently found that the hydrazine derivatives of the general formula (I) are novel compounds not concretely described in prior references and not known in any literature, and are insecticides which have an excellent insecticidal effect at a low dose and are harmless to environment, whereby the present invention has been accomplished.

The above-mentioned hydrazine of the general formula (I) of the present invention which is useful as an agricultural and horticultural insecticide can be produced, for example, by any of the following processes.

Production process 1.

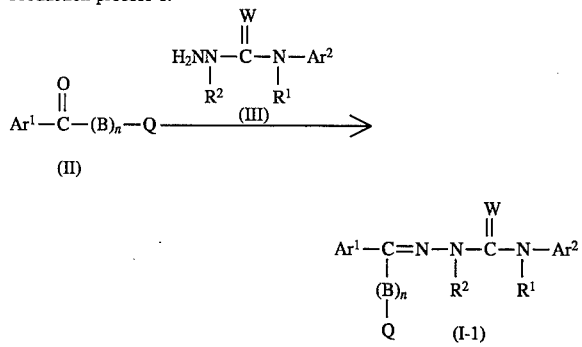

wherein $Ar^1$, $Ar^2$, $R^1$, $R^2$, B, n, Q and W are as defined above.

A hydrazine derivative of the general formula (I-1) can be produced by reacting a compound of the general formula (II) with a compound of the general formula (III) in the presence of an inert solvent and in the presence or absence of a catalyst.

As the inert solvent usable in this reaction, any inert solvent may be used so long as it does not markedly inhibit the progress of the reaction. There may be used, for example, alcohols such as methanol, ethanol, propanol, butanol, etc.; halogenated hydrocarbons such as dichloromethane, chloroform, carbon tetrachloride, etc.; non-halogenated or halogenated aromatic hydrocarbons such as benzene, toluene, xylene, chlorobenzene, etc.; nitriles such as acetonitrile, benzonitrile, etc.; acyclic or cyclic ethers such as Methyl Cellosolve, diethyl ether, diglyme, dioxane, tetrahydrofuran, etc.; carboxylic acids such as acetic acid, etc.; dimethylacetamide; dimethyl sulfoxide; and water. These inert solvents may be used singly or as a mixture thereof.

As the catalyst used in the reaction, there can be used, for example, inorganic acids such as hydrochloric acid, sulfuric acid, and the like; or organic acids such as p-toluenesulfonic acid and the like. As to the amount of the catalyst used, it is sufficient that the catalyst is present in the reaction system in an amount of 0.001 to 10% by weight based on the weight of the compound of the general formula (II).

Since the reaction is an equimolar reaction, it is sufficient that the reactants are used in equimolar amounts, though either of them may be used in excess.

The reaction temperature is chosen in the range of room temperature to the boiling point of the inert solvent used, and is preferably 70° C. to 80° C.

Although the reaction time is varied depending on the reaction temperature, the degree of the reaction, etc., it may be properly chosen in the range of several minutes to 48 hours.

After completion of the reaction, the desired compound is isolated from a reaction solution containing the desired compound by a conventional method such as distilling-off of the solvent, solvent extraction, etc., and if necessary, purified by recrystallization, column chromatography, etc., whereby the desired compound can be produced.

The compound of the general formula (II) can be produced from a corresponding benzoic acid, benzaldehyde or acetophenone by a conventional process, and the compound of the general formula (III) can be produced by the following process:

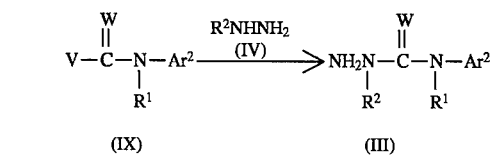

wherein $Ar^2$, $R^1$, $R^2$ and W are as defined above, and V is a halogen atom or a leaving group such as ($C_{1-6}$)alkoxy group, phenoxy group, p-nitrophenoxy group or imidazole group).

The compound of the general formula (III) can be produced by reacting a compound of the general formula (IX) with a hydrazine of the general formula (IV) in the presence of an inert solvent and a base.

Production process 2.

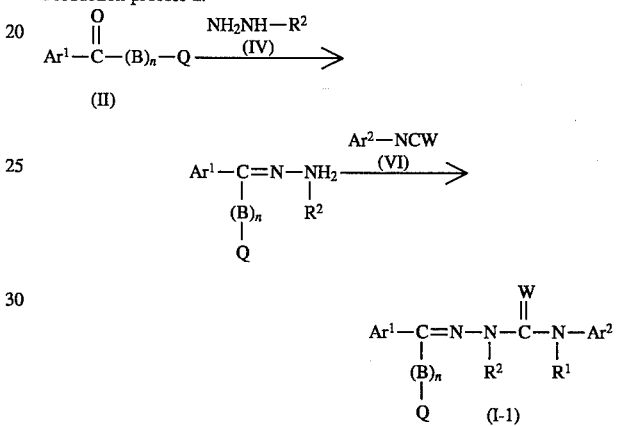

wherein $Ar^1$, $Ar^2$, $R^1$, $R^2$, B, n, Q and W are as defined above, except that $R^1$ is a hydrogen atom.

A hydrazine derivative of the general formula (I-1) can be produced by reacting a compound of the general formula (II) with a hydrazine of the structural formula (IV) in the presence of an inert solvent and in the presence or absence of a catalyst to obtain a compound of the general formula (V), and reacting the compound (V) with a compound of the general formula (VI) in the presence of an inert solvent and in the presence or absence of a catalyst after or without isolating the compound (V).

2-1. General formula (II)→general formula (V)

As the inert solvent usable in this reaction, there can be used, for example, the inert solvents exemplified in production process 1. The kind and amount of the catalyst used in this reaction may be selected from those exemplified in production process 1.

The hydrazine of the structural formula (IV) may be used in the form of either any of various salts or an aqueous solution having a suitable concentration. As to the amount of this hydrazine used, the hydrazine can be used in an amount equimolar with or larger than the amount of the compound of the general formula (II). Preferably, the amount is properly chosen in the range of 2 to 10 moles per mole of the compound of the general formula (II).

The reaction temperature may be properly chosen in the range of room temperature to the boiling point of the inert solvent used, and is preferably 70° C. to 100° C.

Although the reaction time is varied depending on the degree of the reaction, the reaction temperature, etc., it may be chosen in the range of several minutes to 48 hours.

After completion of the reaction, the desired compound is isolated from a reaction solution containing the desired compound by a conventional method such as distilling-off of the solvent, solvent extraction, or the like, and if necessary, purified by recrystallization, column chromatography, etc., whereby the desired compound can be produced.

The compound of the general formula (V) produced by this reaction may be subjected to the subsequent reaction either after isolation and purification by the above method, or without isolation.

2-2. General formula (V)→general formula (I-1)

As the inert solvent usable in this reaction, there can be used, for example, the inert solvents exemplified in production process 1 except for the alcohols, the carboxylic acids and water. There can also be used esters such as ethyl acetate and the like and pyridines.

As the catalyst usable in the reaction, there can be used, for example, amines such as triethyamine. The amount of the catalyst used may be properly chosen in the range of a catalytic amount to excess moles over the compound of the general formula (V).

Since the reaction is an equimolar reaction, it is sufficient that the reactants are used in equimolar amounts, though either of them may be used in excess.

The reaction temperature may be chosen in the range of $-20°$ C. to the boiling point of the inert solvent used, and is preferably $-10°$ C. to room temperature.

Although the reaction time is varied depending on the degree of the reaction, the reaction temperature, etc., it may be chosen in the range of several minutes to 48 hours.

After completion of the reaction, the same treatment as in 2-1 is carried out, whereby the desired compound can be produced.

Production process 3.
[when n = 0 and Q = S(O)$_m$—R$^3$ in the general formula (I-1)]

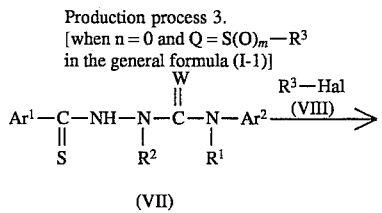

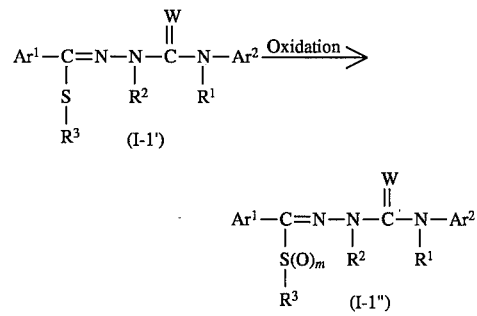

wherein Ar$^1$, Ar$^2$, R$^1$, R$^2$, R$^3$, m and W are as defined above, and Hal is a halogen atom.

A hydrazine derivative of the general formula (I-1') can be produced by reacting a compound of the general formula (VII) with a compound of the general formula (VIII) in the presence of an inert solvent and a base. A hydrazine derivative of the general formula (I-1") can be produced by oxidizing the hydrazine derivative of the general formula (I-1') in the presence of an inert solvent and an oxidizing agent after or without isolating this compound.

3-1. General formula (VII)→general formula (I-1')

As the inert solvent usable in this reaction, any inert solvent may be used so long as it does not markedly inhibit the progress of the reaction. There may be used, for example, alcohols such as methanol, ethanol, propanol, butanol, etc.; halogenated hydrocarbons such as dichloromethane, chloroform, carbon tetrachloride, etc.; non-halogenated or halogenated aromatic hydrocarbons such as benzene, toluene, xylene, chlorobenzene, etc.; nitriles such as acetonitrile, benzonitrile, etc.; carboxylic acids such as acetic acid, etc.; dimethylformamide; dimethylacetamide; dimethyl sulfoxide; and water. These inert solvents may be used singly or as a mixture thereof.

As the base used in the reaction, an inorganic base or an organic base may be used. As the inorganic base, there may be used, for example, hydroxides, carbonates or hydrogencarbonates of alkali metal atoms or alkaline earth metal atoms, such as sodium hydroxide, potassium hydroxide, calcium hydroxide, sodium carbonate, potassium carbonate, calcium carbonate, sodium hydrogencarbonate, etc. As the organic base, there may be used triethylamine, pyridine, etc. The amount of the base used may be chosen in the range of 1 mole to excess moles per mole of the compound of the general formula (VII).

Since the reaction is an equimolar reaction, it is sufficient that the compound of the general formula (VII) and the compound of the general formula (VIII) are used in equimolar amounts, though either of them may be used in excess.

The reaction temperature is preferably chosen in the range of room temperature to the boiling point of the inert solvent used, and is more preferably a room temperature or thereabout.

Although the reaction time is varied depending on the reaction temperature, the degree of the reaction, etc., it may be properly chosen in the range of several minutes to 48 hours.

After completion of the reaction, the desired compound is isolated from a reaction solution containing the desired compound by a conventional method such as distilling-off of the solvent, solvent extraction, or the like, and if necessary, purified by recrystallization, column chromatography, etc., whereby the desired compound can be produced.

3-2. General formula (I-1')→general formula (I-1")

As the inert solvent usable in this reaction, the same inert solvent as used in 3-1 can be used and any of the alcohols or water is preferably used.

As the oxidizing agent, there can be used, for example, hydrogen peroxide, monopersulfate compounds (e.g. sodium peroxymonosulfate), benzoyl peroxide and m-chloroperbenzoic acid. Of these, monopersulfate compound or m-chloroperbenzoic acid is preferable. Although the amount of the oxidizing agent used is varied depending on the desired monooxide or dioxide compound, it is preferably chosen in the range of 1 mole to excess moles per mole of the compound of the general formula (I-1'). Preferably, the oxidizing agent is used in excess.

The reaction temperature is preferably chosen in the range of room temperature to the boiling point of the inert solvent used, more preferably in the range of room temperature to 50° C.

Although the reaction time is varied depending on the reaction temperature, the degree of the reaction, etc., it may be chosen in the range of several minutes to 48 hours.

After completion of the reaction, the desired compound is isolated from a reaction solution containing the desired compound by a conventional method such as distilling-off of the solvent, solvent extraction, or the like, and if necessary, purified by recrystallization, column chromatography, etc., whereby the desired compound can be produced.

The compound of the general formula (VII), i.e., the starting material in the reaction can be produced according to J.O.C. 26, 5221 (1961).

Typical examples of the hydrazine derivatives of the general formula (I-1) produced by production processes 1, 2 and 3 are given in Table 1 but they are not intended in any way to limit the scope of the present invention.

General formula (I-1):

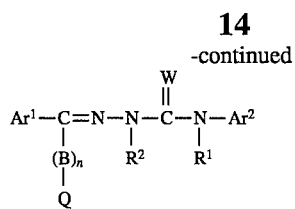

TABLE 1

($R^1$ = H, W = 0, Ph = phenyl)

| No. | $Ar^1$ | $Ar^2$ | $R^2$ | $(B)_n$ | Q | Melting point (°C.) |
|---|---|---|---|---|---|---|
| 1 | Ph | 4-Cl—Ph | H | $CH_2$ | —O—Ph | 197 |
| 2 | Ph | 4-Cl—Ph | H | $CH_2$ | —S—Ph | 200 |
| 3 | Ph | 4-Cl—Ph | H | $CH_2$ | —SO Ph | 191 (decomp.) |
| 4 | Ph | 4-Cl—Ph | H | $CH_2$ | —$SO_2CH_3$ | 232 |
| 5 | Ph | 4-Cl—Ph | H | $CH_2$ | —CONH—Ph | 218 |
| 6 | Ph | 4-Br—Ph | H | $CH_2$ | —$SO_2CH_3$ | 232 |
| 7 | Ph | 4-$CF_3$—Ph | H | $CH_2$ | —O—Ph | 199 |
| 8 | Ph | 4-$CF_3$—Ph | H | $CH_2$ | —S—Ph | 197 |
| 9 | Ph | 4-$CF_3$—Ph | H | $CH_2$ | —SO—Ph | 188 (decomp.) |
| 10 | Ph | 4-$OCF_3$—Ph | H | — | —$CONH_2$ | 218 Z-form |
| 11 | Ph | 4-$OCF_3$—Ph | H | — | —$CONH_2$ | 221 E-form |
| 12 | Ph | 4-$OCF_3$—Ph | H | — | —$CONHCH_3$ | 178 Z-form |
| 13 | Ph | 4-$OCF_3$—Ph | H | — | —$CONHCH_3$ | 115 E-form |
| 14 | Ph | 4-$OCF_3$—Ph | H | — | —$CON(CH_3)_2$ | 175 |
| 15 | Ph | 4-$OCF_3$—Ph | H | — | —CON(Ph)($CH_3$) | 131 |
| 16 | Ph | 4-$OCF_3$—Ph | H | — | —CONH—Ph-4-$OCF_3$ | 190 |
| 17 | Ph | 4-$OCF_3$—Ph | H | — | —CON(piperidine) | 175 |
| 18 | Ph | 4-$OCF_3$—Ph | H | — | —CON(morpholine) | 155 |
| 19 | Ph | 4-$OCF_3$—Ph | H | — | —CON(piperazine-NH) | Vitreous |
| 20 | Ph | 4-$OCF_3$—Ph | H | — | —CON(piperazine-$NCH_3$) | 161 |
| 21 | Ph | 4-$OCF_3$—Ph | H | — | —CON(piperazine-$NCH_2$—Ph) | Vitreous |
| 22 | Ph | 4-$OCF_3$—Ph | H | — | —CON(piperazine-$NCO_2CH_3$) | 186 |
| 23 | Ph | 4-$OCF_3$—Ph | H | — | —$CO_2CH_3$ | 130 |
| 24 | Ph | 4-$OCF_3$—Ph | H | $CH_2$ | —CN | 179 |
| 25 | Ph | 4-$OCF_3$—Ph | H | $CH_2$ | —$OCH_3$ | 131 |
| 26 | Ph | 4-$OCF_3$—Ph | H | $CH_2$ | —O—Ph | 184 |
| 27 | Ph | 4-$OCF_3$—Ph | H | $CH_2$ | —O—Ph-4-$NO_2$ | 172 |
| 28 | Ph | 4-$OCF_3$—Ph | H | $CH_2$ | —O—Ph-4-CN | 190 E-form |

TABLE 1-continued (R¹ = H, W = 0, Ph = phenyl)

| No. | Ar¹ | Ar² | R² | (B)ₙ | Q | Melting point (°C.) |
|---|---|---|---|---|---|---|
| 29 | Ph | 4-OCF₃—Ph | H | CH₂ | —O—Ph-4-CN | 179 Z-form |
| 30 | Ph | 4-OCF₃—Ph | H | CH₂ | —SH | 191 |
| 31 | Ph | 4-OCF₃—Ph | H | CH₂ | —SCH₃ | 186 |
| 32 | Ph | 4-OCF₃—Ph | H | CH₂ | —SO₂CH₃ | 232 |
| 33 | Ph | 4-OCF₃—Ph | H | CH₂ | —SC₃H₇-i | 163 |
| 34 | Ph | 4-OCF₃—Ph | H | CH₂ | —SCH₂C≡CH | 184 |
| 35 | Ph | 4-OCF₃—Ph | H | CH₂ | —SCH₂CO₂CH₃ | 128 |
| 36 | Ph | 4-OCF₃—Ph | H | CH₂ | —SCOCH₃ | 177 |
| 37 | Ph | 4-OCF₃—Ph | H | CH₂ | —S—Ph | 192 |
| 38 | Ph | 4-OCF₃—Ph | H | CH₂ | —S—Ph-4-Cl | 196 |
| 39 | Ph | 4-OCF₃—Ph | H | CH₂ | —S—Ph-4-NO₂ | 186 |
| 40 | Ph | 4-OCF₃—Ph | H | CH₂ | —SO—Ph | 192 (decomp.) |
| 41 | Ph | 4-OCF₃—Ph | H | CH₂ | —SO—Ph-4-Cl | 190 |
| 42 | Ph | 4-OCF₃—Ph | H | CH₂ | —SO₂—Ph | 219 |
| 43 | Ph | 4-OCF₃—Ph | H | CH₂ | —SO₂—Ph-4-NO₂ | 218 |
| 44 | Ph | 4-OCF₃—Ph | H | CH₂ | —CO₂C₂H₅ | 208 |
| 45 | Ph | 4-OCF₃—Ph | H | CH₂ | —CONHC₄H₉-t | 172 |
| 46 | Ph | 4-OCF₃—Ph | H | CH₂ | —CONH—Ph | 270 (decomp.) |
| 47 | Ph | 4-OCF₃—Ph | H | CH₂ | —CONH—Ph-4-Cl | 243 |
| 48 | Ph | 4-OCF₃—Ph | H | CH₂ | —CONH—Ph-4-Br | 276 |
| 49 | Ph | 4-OCF₃—Ph | H | CH₂ | —CONH—Ph-4-CN | 180 |
| 50 | Ph | 4-OCF₃—Ph | H | CH₂ | —CONH—Ph-4-CH₃ | 210 (decomp.) |
| 51 | Ph | 4-OCF₃—Ph | H | CH₂ | —CONH—Ph-4-C₃H₇-i | 164 |
| 52 | Ph | 4-OCF₃—Ph | H | CH₂ | —CONH—Ph-4-OCH₃ | 189 |
| 53 | Ph | 4-OCF₃—Ph | H | CH₂ | —CONH—Ph-4-OCF₃ | 187 |
| 54 | Ph | 4-OCF₃—Ph | H | CH₂ | —N(CH₃)₂ | 60 E-form |
| 55 | Ph | 4-OCF₃—Ph | H | CH₂ | —N(CH₃)₂ | 210 Z-form |
| 56 | Ph | 4-OCF₃—Ph | H | CH₂ | —NHCHO | 181 |
| 57 | Ph | 4-OCF₃—Ph | H | —CH(CH₃)— | —NHCHO | 167 |
| 58 | Ph | 4-OCF₃—Ph | H | CH₂ | —NHCOCH₃ | 222 |
| 59 | Ph | 4-OCF₃—Ph | H | CH₂ | —NHCOC₃H₇-i | 205 |
| 60 | Ph | 4-OCF₃—Ph | H | CH₂ | NHCO₂C₂H₅ | 152 |
| 61 | Ph | 4-OCF₃—Ph | H | CH₂ | —NHCONHC₂H₅ | 201 |
| 62 | Ph | 4-OCF₃—Ph | H | CH₂ | —NHCON(C₂H₅)₂ | 86 |
| 63 | Ph | 4-OCF₃—Ph | H | CH₂ | —NH—Ph | 170 E-form |
| 64 | Ph | 4-OCF₃—Ph | H | CH₂ | —NH—Ph | 120 Z-form |
| 65 | Ph | 4-OCF₃—Ph | H | CH₂ | —NHCO—Ph | 197 |
| 66 | Ph | 4-OCF₃—Ph | H | CH₂ | —NHCO—Ph-4-Cl | 202 |
| 67 | Ph | 4-OCF₃—Ph | H | CH₂ | —NHCO—Ph-2,4-Cl₂ | 207 |
| 68 | Ph | 4-OCF₃—Ph | H | CH₂ | NHCO—Ph-4-NO₂ | 235 |
| 69 | Ph | 4-OCF₃—Ph | H | CH₂ | —NHCO—Ph-4-CN | 186 |
| 70 | Ph | 4-OCF₃—Ph | H | CH₂ | —NHSO₂—Ph-4-Cl | 150 |
| 71 | Ph | 4-OCF₃—Ph | H | CH₂ | —NHSO₂—Ph-4-CH₃ | 150 |
| 72 | Ph | 4-OCF₃—Ph | H | (CH₂)₂ | —CN | 181 |
| 73 | Ph | 4-OCF₃—Ph | H | (CH₂)₂ | —OC₂H₅ | 134.1 |
| 74 | Ph | 4-OCF₃—Ph | H | (CH₂)₂ | —NHCHO | 185 |
| 75 | Ph | 4-OCF₃—Ph | H | (CH₂)₂ | —N(CHO)₂ | 198 |
| 76 | Ph | 4-OCF₃—Ph | H | (CH₂)₂ | —NHCOCH₃ | 210 |
| 77 | Ph | 4-OCF₃—Ph | H | (CH₂)₂ | —NHCO₂CH₃ | 208 |
| 78 | Ph | 4-OCF₃—Ph | H | (CH₂)₂ | —NHCON(CH₃)₂ | 183 |
| 79 | Ph | 4-OCF₃—Ph | H | (CH₂)₂ | —NHCO—Ph-4-Cl | 222 |
| 80 | Ph | 4-OCF₃—Ph | H | (CH₂)₂ | —NHSO₂CH₃ | 188 |
| 81 | Ph | 4-OCF₃—Ph | H | (CH₂)₂ | —NHSO₂N(CH₃)₂ | 191 |
| 82 | Ph | 4-OCF₃—Ph | H | —CH(CH₃)— | —CN | paste |
| 83 | Ph | 4-OCF₃—Ph | H | —CH(CH₃)— | —NHCO—Ph | 150 |

TABLE 1-continued ($R^1$ = H, W = 0, Ph = phenyl)

| No. | Ar¹ | Ar² | R² | (B)ₙ | Q | Melting point (°C.) |
|---|---|---|---|---|---|---|
| 84 | Ph | 4-OCF₃—Ph | H | —C(CH₃)₂— | —CN | 149 |
| 85 | Ph | 4-OCF₃—Ph | H | —C— (cyclopropyl) | —SCH₃ | 121 E:Z = 4:1 |
| 86 | Ph | 4-OCF₃—Ph | H | —C— (cyclopropyl) | —SCH₂—Ph | paste Z-form |
| 87 | Ph | 4-OCF₃—Ph | H | —C— (cyclopropyl) | —SCH₂—Ph | paste E-form |
| 88 | Ph | 4-OCF₃—Ph | CH₃ | CH₂ | —SO₂CH₃ | 157 |
| 89 | Ph | 4-OCF₃—Ph | CH₃ | —CH(CH₃)— | —SO₂CH₃ | paste |
| 90 | Ph | 4-SCF₃—Ph | H | —C— (cyclopropyl) | —SCH₃ | paste |
| 91 | 2-Cl—Ph | 4-OCF₃—Ph | H | CH₂ | —O—Ph-4-CN | 145 Z-form |
| 92 | 2-Cl—Ph | 4-OCF₃—Ph | H | CH₂ | —O—Ph-4-CN | 127 E-form |
| 93 | 3-Cl—Ph | 4-OCF₃—Ph | H | — | —CO₂CH₃ | 134 |
| 94 | 3-Cl—Ph | 4-OCF₃—Ph | H | — | —CONH₂ | 213 E:Z = 1:1 |
| 95 | 3-Cl—Ph | 4-OCF₃—Ph | H | — | —CONHCH₃ | 191 Z-form |
| 96 | 3-Cl—Ph | 4-OCF₃—Ph | H | — | —CONHCH₃ | paste E-form |
| 97 | 3-Cl—Ph | 4-OCF₃—Ph | H | — | —CON(CH₃)₂ | 139 |
| 98 | 3-Cl—Ph | 4-OCF₃—Ph | H | — | —CON(C₂H₅)₂ | vitreous |
| 99 | 3-Cl—Ph | 4-OCF₃—Ph | H | — | —CONHC₃H₇-n | 177 Z-form |
| 100 | 3-Cl—Ph | 4-OCF₃—Ph | H | — | —CONHC₃H₇-n | paste E-form |
| 101 | 3-Cl—Ph | 4-OCF₃—Ph | H | — | —CON(C₃H₇-i)₂ | 185 |
| 102 | 3-Cl—Ph | 4-OCF₃—Ph | H | — | —CONH—cyclohexyl | 209 Z-form |
| 103 | 3-Cl—Ph | 4-OCF₃—Ph | H | — | —CONH—cyclohexyl | vitreous E-form |
| 104 | 3-Cl—Ph | 4-OCF₃—Ph | H | — | —CON(CH₃)—cyclohexyl | paste |
| 105 | 3-Cl—Ph | 4-OCF₃—Ph | H | — | —CON(piperidinyl-4-COOC₂H₅) | paste |
| 106 | 3-Cl—Ph | 4-OCF₃—Ph | H | — | —CON(morpholino) | vitreous |

TABLE 1-continued (R¹ = H, W = 0, Ph = phenyl)

| No. | Ar¹ | Ar² | R² | (B)ₙ | Q | Melting point (°C.) |
|---|---|---|---|---|---|---|
| 107 | 3-Cl—Ph | 4-OCF₃—Ph | H | — | —CON⟨⟩NH | vitreous |
| 108 | 3-Cl—Ph | 4-OCF₃—Ph | H | — | —CON⟨⟩NCOOCH₃ | vitreous |
| 109 | 3-Cl—Ph | 4-OCF₃—Ph | H | — | —CON⟨⟩NCOCH₃ | vitreous |
| 110 | 3-Cl—Ph | 4-OCF₃—Ph | H | — | —CON⟨⟩NCO—Ph-2-Cl | 204 |
| 111 | 3-Cl—Ph | 4-OCF₃—Ph | H | — | —CON⟨⟩NCONHC₂H₅ | vitreous |
| 112 | 3-Cl—Ph | 4-OCF₃—Ph | H | — | —CON⟨⟩NCON(C₂H₅)₂ | vitreous |
| 113 | 3-Cl—Ph | 4-OCF₃—Ph | H | CH₂ | —O—Ph-3-NO₂ | 182 |
| 114 | 3-Cl—Ph | 4-OCF₃—Ph | H | CH₂ | —O—Ph-4-NO₂ | 120 |
| 115 | 3-Cl—Ph | 4-OCF₃—Ph | H | CH₂ | —O—Ph-4-CN | 105 |
| 116 | 3-Cl—Ph | 4-OCF₃—Ph | H | CH₂ | —O—Ph-4-COOCH₃ | 220 |
| 117 | 3-Cl—Ph | 4-OCF₃—Ph | H | CH₂ | —O—Ph-4-SCH₃ | 201 |
| 118 | 3-Cl—Ph | 4-OCF₃—Ph | H | CH₂ | —O—Ph-4-SOCH₃ | 155 |
| 119 | 3-Cl—Ph | 4-OCF₃—Ph | H | CH₂ | —NHCOC₂H₅ | 192 |
| 120 | 3-Cl—Ph | 4-OCF₃—Ph | H | CH₂ | —NHCOC₃H₇-n | 157 |
| 121 | 3-Cl—Ph | 4-OCF₃—Ph | H | CH₂ | —NHCOC₃H₇-i | 203 |
| 122 | 3-Cl—Ph | 4-OCF₃—Ph | H | CH₂ | —NHCOC₄H₉-t | 157 |
| 123 | 3-Cl—Ph | 4-OCF₃—Ph | H | CH₂ | —NHCO—⟨⟩-H | 198 |
| 124 | 3-Cl—Ph | 4-OCF₃—Ph | H | CH₂ | —NHCO—Ph | 199 |
| 125 | 3-Cl—Ph | 4-OCF₃—Ph | H | (CH₂)₂ | —CN | 158 |
| 126 | 3-Cl—Ph | 4-OCF₃—Ph | H | (CH₂)₂ | —CO₂C₂H₅ | 111 |
| 127 | 3-Cl—Ph | 4-OCF₃—Ph | H | (CH₂)₂ | —CONH₂ | 196 |
| 128 | 3-Cl—Ph | 4-OCF₃—Ph | H | (CH₂)₂ | —CON(CH₃)₂ | 119 |
| 129 | 3-Cl—Ph | 4-OCF₃—Ph | H | (CH₂)₂ | —CON(C₂H₅)₂ | 123 |
| 130 | 3-Cl—Ph | 4-OCF₃—Ph | H | (CH₂)₂ | —CONHC₃H₇-n | 225 |
| 131 | 3-Cl—Ph | 4-OCF₃—Ph | H | (CH₂)₂ | —CONHCH₂CH=CH₂ | 215 |
| 132 | 3-Cl—Ph | 4-OCF₃—Ph | H | (CH₂)₂ | —CONHCH₂CN | 230 |
| 133 | 3-Cl—Ph | 4-OCF₃—Ph | H | (CH₂)₂ | CONHCH₂CONHCH₃ | 225 |
| 134 | 3-Cl—Ph | 4-OCF₃—Ph | H | (CH₂)₂ | CONHCH₂CO₂C₂H₅ | 216 |
| 135 | 3-Cl—Ph | 4-OCF₃—Ph | H | (CH₂)₂ | —CONCH₂CO₂CH₃ (I CH₃) | 156 |
| 136 | 3-Cl—Ph | 4-OCF₃—Ph | H | (CH₂)₂ | —CONCH₂CONHCH₃ (I CH₃) | 170 |
| 137 | 3-Cl—Ph | 4-OCF₃—Ph | H | (CH₂)₂ | —CONHCH₂—Ph | 223 |
| 138 | 3-Cl—Ph | 4-OCF₃—Ph | H | (CH₂)₂ | —CONHCH₂—⟨furan-O⟩ | 215 |

TABLE 1-continued (R¹ = H, W = 0, Ph = phenyl)

| No. | Ar¹ | Ar² | R² | (B)ₙ | Q | Melting point (°C.) |
|---|---|---|---|---|---|---|
| 139 | 3-Cl—Ph | 4-OCF₃—Ph | H | (CH₂)₂ | —CON(CH₂CH₂)₂O | 156 |
| 140 | 3-Cl—Ph | 4-OCF₃—Ph | H | (CH₂)₂ | —CON(CH₂CH₂)₂NCH₃ | 168 |
| 141 | 3-Cl—Ph | 4-OCF₃—Ph | H | (CH₂)₃ | —CN | 152 |
| 142 | 3-Cl—Ph | 4-OCF₃—Ph | H | CH₂CH(CH₃) | —CN | 57 |
| 143 | 3-Cl—Ph | 4-OCF₃—Ph | H | CH₂CH(CH₃) | —CONH₂ | 218 |
| 144 | 3-Cl—Ph | 4-OCF₃—Ph | H | CHCH₂(CH₃) | —CONH₂ | 66 |
| 145 | 3-Cl—Ph | 4-OCF₃—Ph | H | (CH₂)₄ | —CN | 169 |
| 146 | 4-Cl—Ph | 4-OCF₃—Ph | H | CH₂ | —O—Ph 4-NO₂ | 180 |
| 147 | 4-Cl—Ph | 4-OCF₃—Ph | H | CH₂ | —O—Ph-4-CN | 200 |
| 148 | 4-Cl—Ph | 4-OCF₃—Ph | H | CH₂ | —S—Ph-4-NO₂ | 190 |
| 149 | 4-Cl—Ph | 4-OCF₃—Ph | H | CH₂ | —S—Ph-4-CH₃ | 195 |
| 150 | 4-Cl—Ph | 4-OCF₃—Ph | H | CH₂ | —SO—Ph-4-NO₂ | 197 |
| 151 | 4-Cl—Ph | 4-OCF₃—Ph | H | CH₂ | —SO—Ph-4-CH₃ | 185 |
| 152 | 4-Cl—Ph | 4-OCF₃—Ph | H | CH₂ | —SO₂—Ph-4-NO₂ | 230 |
| 153 | 4-Cl—Ph | 4-OCF₃—Ph | H | CH₂ | —SO₂—Ph-4-CH₃ | 237 |
| 154 | 4-Cl—Ph | 4-OCF₃—Ph | H | CH₂ | —NHCO—Ph | 190 |
| 155 | 4-Cl—Ph | 4-OCF₃—Ph | H | (CH₂)₂ | —N(CH₃)₂ | 125 |
| 156 | 4-Cl—Ph | 4-OCF₃—Ph | H | (CH₂)₂ | —CONH₂ | 215 |
| 157 | 4-Cl—Ph | 4-OCF₃—Ph | H | (CH₂)₄ | —CN | 180 |
| 158 | 3-Br—Ph | 4-OCF₃—Ph | H | (CH₂)₂ | —CONH₂ | 209 |
| 159 | 4-Br—Ph | 4-OCF₃—Ph | H | CH₂ | —O—Ph-4-CN | 210 |
| 160 | 4-F—Ph | 4-OCF₃—Ph | H | — | —CO₂CH₃ | paste Z-form |
| 161 | 4-F—Ph | 4-OCF₃—Ph | H | — | —CO₂CH₃ | 166 E-form |
| 162 | 4-F—Ph | 4-OCF₃—Ph | H | — | —CONHCH₃ | 168 Z-form |
| 163 | 4-F—Ph | 4-OCF₃—Ph | H | — | —CONHCH₃ | vitreous E-form |
| 164 | 4-F—Ph | 4-OCF₃—Ph | H | — | —CON(CH₃)₂ | 152 |
| 165 | 4-F—Ph | 4-OCF₃—Ph | H | — | —CON(C₂H₅)₂ | vitreous |
| 166 | 4-F—Ph | 4-OCF₃—Ph | H | — | —CON(CH₂CH₂)₂ (pyrrolidine/piperidine ring) | 154 |
| 167 | 4-F—Ph | 4-OCF₃—Ph | H | — | —CON(CH₂CH₂)₂O | 178 |
| 168 | 4-F—Ph | 4-OCF₃—Ph | H | — | —CON(CH₂CH₂)₂NCOOCH₃ | 215 |
| 169 | 4-F—Ph | 4-OCF₃—Ph | H | — | —CON(CH₂CH₂)₂NCOOC₃H₇-i | 180 |
| 170 | 3-NO₂—Ph | 4-OCF₃—Ph | H | CH₂ | —O—Ph-4-CN | 190 |
| 171 | 3-CH₃—Ph | 4-OCF₃—Ph | H | CH₂ | —O—Ph-4-CN | 160 |
| 172 | 3-CH₃—Ph | 4-OCF₃—Ph | H | CH₂ | —NHCO—Ph | 194 |

TABLE 1-continued ($R^1$ = H, W = 0, Ph = phenyl)

| No. | $Ar^1$ | $Ar^2$ | $R^2$ | $(B)_n$ | Q | Melting point (°C.) |
|---|---|---|---|---|---|---|
| 173 | 3-$CH_3$—Ph | 4-$OCF_3$—Ph | H | $(CH_2)_2$ | —$CONH_2$ | 231 |
| 174 | 4-$CH_3$—Ph | 4-$OCF_3$—Ph | H | $(CH_2)_2$ | —$N(CH_3)_2$ | 170 |
| 175 | 3-$CF_3$—Ph | 4-$OCF_3$—Ph | H | — | —$CO_2CH_3$ | 141 Z-form |
| 176 | 3-$CF_3$—Ph | 4-$OCF_3$—Ph | H | — | —$CO_2CH_3$ | 137 E-form |
| 177 | 3-$CF_3$—Ph | 4-$OCF_3$—Ph | H | — | —CH=C($CH_3)_2$ | 131 |
| 178 | 3-$CF_3$—Ph | 4-$OCF_3$—Ph | H | — | —$CON(CH_3)_2$ | vitreous |
| 179 | 3-$CF_3$—Ph | 4-$OCF_3$—Ph | H | — | —$CONHC_4H_9$-t | 160 Z-form |
| 180 | 3-$CF_3$—Ph | 4-$OCF_3$—Ph | H | — | —$CONHC_4H_9$-t | 169 E-form |
| 181 | 3-$CF_3$—Ph | 4-$OCF_3$—Ph | H | — | —CONH—Ph | paste Z-form |
| 182 | 3-$CF_3$—Ph | 4-$OCF_3$—Ph | H | — | —CONH—Ph | 140 E-form |
| 183 | 3-$CF_3$—Ph | 4-$OCF_3$—Ph | H | — | —CON(morpholino) O | 148 |
| 184 | 3-$CF_3$—Ph | 4-$OCF_3$—Ph | H | — | —CON(piperazino)NCN | 102 |
| 185 | 3-$CF_3$—Ph | 4-$OCF_3$—Ph | H | — | —CON(piperazino)NCOOCH$_3$ | paste |
| 186 | 3-$CF_3$—Ph | 4-$OCF_3$—Ph | H | — | —CON(piperazino)NCOOC$_3$H$_7$-i | 98 |
| 187 | 3-$CF_3$—Ph | 4-$OCF_3$—Ph | H | — | —CON(piperazino)NSO$_2$CH$_3$ | 107 |
| 188 | 3-$CF_3$—Ph | 4-$OCF_3$—Ph | H | — | —CON(piperazino)NCSNHCH$_3$ | 157 |
| 189 | 3-$CF_3$—Ph | 4-$OCF_3$—Ph | H | — | —$CON(CH_2CN)_2$ | 101 |
| 190 | 3-$CF_3$—Ph | 4-$OCF_3$—Ph | H | — | —CONCH$_2$CN / CH$_3$ | paste |
| 191 | 3-$CF_3$—Ph | 4-$OCF_3$—Ph | H | — | —$CONHCH_2CH_2OCH_3$ | 146 Z-form |
| 192 | 3-$CF_3$—Ph | 4-$OCF_3$—Ph | H | — | —$CONHCH_2CH_2OCH_3$ | 85 E-form |
| 193 | 3-$CF_3$—Ph | 4-$OCF_3$—Ph | H | — | —CONCH$_2$Ph / CH$_3$ | 194 |
| 194 | 3-$CF_3$—Ph | 4-$OCF_3$—Ph | H | — | —CON(piperazino)NCOC$_4$H$_9$-t | 188 |

TABLE 1-continued (R¹ = H, W = 0, Ph = phenyl)

| No. | Ar¹ | Ar² | R² | (B)ₙ | Q | Melting point (°C.) |
|---|---|---|---|---|---|---|
| 195 | 3-CF₃—Ph | 4-OCF₃—Ph | H | — | —CON(trans-2,6-dimethylmorpholine) | 189 |
| 196 | 3-CF₃—Ph | 4-OCF₃—Ph | H | — | —CON(2-methyl-6-phenylmorpholine) | paste |
| 197 | 3-CF₃—Ph | 4-OCF₃—Ph | H | CH₂ | —OCH₃ | 142 |
| 198 | 3-CF₃—Ph | 4-OCF₃—Ph | H | CH₂ | —O—Ph-4-CN | 165 |
| 199 | 3-CF₃—Ph | 4-OCF₃—Ph | H | CH₂ | —SC₃H₇-i | 164 |
| 200 | 3-CF₃—Ph | 4-OCF₃—Ph | H | CH₂ | —SO₂C₃H₇-i | 224 |
| 201 | 3-CF₃—Ph | 4-OCF₃—Ph | H | CH₂ | —SC₄H₉-t | 209 |
| 202 | 3-CF₃—Ph | 4-OCF₃—Ph | H | CH₂ | —SCH₂-cyclopropyl | 180 |
| 203 | 3-CF₃—Ph | 4-OCF₃—Ph | H | CH₂ | —SOCH₂-cyclopropyl | 214 |
| 204 | 3-CF₃—Ph | 4-OCF₃—Ph | H | CH₂ | —SCH₂CH=CH₂ | 131 |
| 205 | 3-CF₃—Ph | 4-OCF₃—Ph | H | CH₂ | —SOCH₂CH=CH₂ | 188 |
| 206 | 3-CF₃—Ph | 4-OCF₃—Ph | H | CH₂ | —SCH₂C≡CH | 155 |
| 207 | 3-CF₃—Ph | 4-OCF₃—Ph | H | CH₂ | —SCH₂CN | 182 |
| 208 | 3-CF₃—Ph | 4-OCF₃—Ph | H | CH₂ | —SCH₂CH₂CN | 123 |
| 209 | 3-CF₃—Ph | 4-OCF₃—Ph | H | CH₂ | —SCH₂CO₂CH₃ | 145 |
| 210 | 3-CF₃—Ph | 4-OCF₃—Ph | H | CH₂ | —SOCH₂CO₂CH₃ | 197 |
| 211 | 3-CF₃—Ph | 4-OCF₃—Ph | H | CH₂ | —SCH₂CO₂C₂H₅ | 134 |
| 212 | 3-CF₃—Ph | 4-OCF₃—Ph | H | CH₂ | —SCH₂CH₂CO₂CH₃ | 133 |
| 213 | 3-CF₃—Ph | 4-OCF₃—Ph | H | CH₂ | —SOCH₂CH₂CO₂CH₃ | 166 |
| 214 | 3-CF₃—Ph | 4-OCF₃—Ph | H | CH₂ | —SCH₂CONH₂ | 178 |
| 215 | 3-CF₃—Ph | 4-OCF₃—Ph | H | CH₂ | —SCH₂CONHC₃H₇-i | 212 |
| 216 | 3-CF₃—Ph | 4-OCF₃—Ph | H | CH₂ | —SCH₂CONHC₄H₉-t | 178 |
| 217 | 3-CF₃—Ph | 4-OCF₃—Ph | H | CH₂ | —SCH₂COCH₃ | 164 |
| 218 | 3-CF₃—Ph | 4-OCF₃—Ph | H | CH₂ | —SOCH₂COCH₃ | 182 |
| 219 | 3-CF₃—Ph | 4-OCF₃—Ph | H | CH₂ | —SCOCH₃ | 173 |
| 220 | 3-CF₃—Ph | 4-OCF₃—Ph | H | CH₂ | —SCN | 169 |
| 221 | 3-CF₃—Ph | 4-OCF₃—Ph | H | CH₂ | —CO₂C₂H₅ | 163 |
| 222 | 3-CF₃—Ph | 4-OCF₃—Ph | H | CH₂ | —CONHC₄H₉-t | 171 |
| 223 | 3-CF₃—Ph | 4-OCF₃—Ph | H | CH₂ | —CONH-cyclohexyl | 197 |
| 224 | 3-CF₃—Ph | 4-OCF₃—Ph | H | CH₂ | —CONH—Ph-4-CN | 174 |
| 225 | 3-CF₃—Ph | 4-OCF₃—Ph | H | CH₂ | —NHCO-cyclopropyl | 224 |
| 226 | 3-CF₃—Ph | 4-OCF₃—Ph | H | CH₂ | —NHCO—Ph | 197 |
| 227 | 3-CF₃—Ph | 4-OCF₃—Ph | H | CH₂ | —NHCO—Ph-2-Cl | 214 |
| 228 | 3-CF₃—Ph | 4-OCF₃—Ph | H | CH₂ | —NHCO—Ph-3-Cl | 189 |
| 229 | 3-CF₃—Ph | 4-OCF₃—Ph | H | CH₂ | —NHCO—Ph-4-Cl | 207 |
| 230 | 3-CF₃—Ph | 4-OCF₃—Ph | H | CH₂ | —NHCO—Ph-4-NO₂ | 205 |
| 231 | 3-CF₃—Ph | 4-OCF₃—Ph | H | CH₂ | —NHCO₂—Ph | 194 |
| 232 | 3-CF₃—Ph | 4-OCF₃—Ph | H | (CH₂)₂ | —CN | 156 |
| 233 | 3-CF₃—Ph | 4-OCF₃—Ph | H | (CH₂)₂ | —CONH₂ | 203 |
| 234 | 3-CF₃—Ph | 4-OCF₃—Ph | H | (CH₂)₂ | —COOC₂H₅ | 153 |
| 235 | 3-CF₃—Ph | 4-OCF₃—Ph | H | (CH₂)₂ | —CON(C₂H₅)₂ | 148 |

TABLE 1-continued ($R^1$ = H, W = O, Ph = phenyl)

| No. | Ar¹ | Ar² | R² | (B)ₙ | Q | Melting point (°C.) |
|---|---|---|---|---|---|---|
| 236 | 3-$CF_3$—Ph | 4-$OCF_3$—Ph | H | $(CH_2)_2$ | —CON(morpholino) | 160 |
| 237 | 3-$CF_3$—Ph | 4-$OCF_3$—Ph | H | —CH(CH$_3$)— | —O—Ph-4-CN | paste E:Z = 1:1 |
| 238 | 3-$CF_3$—Ph | 4-$OCF_3$—Ph | H | —CH$_2$CH(CH$_3$)— | —CON($C_2H_5$)$_2$ | 142 |
| 239 | 3-$CF_3$—Ph | 4-$OCF_3$—Ph | H | CH$_2$CH(CH$_3$) | —CON(morpholino) | vitreous |
| 240 | 3-$CF_3$—Ph | 4-$OCF_3$—Ph | H | $(CH_2)_3$ | —CN | 175 |
| 241 | 3-$CF_3$—Ph | 4-$OCF_3$—Ph | H | $(CH_2)_3$ | —$CO_2C_2H_5$ | 151 |
| 242 | 3-$CF_3$—Ph | 4-$OCF_3$—Ph | H | $(CH_2)_3$ | —$CONH_2$ | 177 |
| 243 | 3-$CF_3$—Ph | 4-$OCF_3$—Ph | H | CH$_2$CH(CH$_3$) | —$CO_2C_2H_5$ | 118 E-form |
| 244 | 3-$CF_3$—Ph | 4-$OCF_3$—Ph | H | CH$_2$CH(CH$_3$) | —$CO_2C_2H_5$ | paste Z-form |
| 245 | 3-$CF_3$—Ph | 4-$OCF_3$—Ph | H | CH$_2$CH(CH$_3$) | —CN | 153 |
| 246 | 3-$CF_3$—Ph | 4-$OCF_3$—Ph | H | CH$_2$CH(CH$_3$) | —$CONH_2$ | 165 |
| 247 | 3-$CF_3$—Ph | 4-$OCF_3$—Ph | H | cyclopropyl —C< | —$CO_2C_2H_5$ | paste |
| 248 | 3-$CF_3$—Ph | 4-$OCF_3$—Ph | H | $(CH_2)_4$ | —$CONH_2$ | 194 |
| 249 | 3-$CF_3$—Ph | 4-$OCF_3$—Ph | H | $(CH_2)_4$ | —CN | 169 |
| 250 | 3-$CF_3$—Ph | 4-$OCF_3$—Ph | H | $(CH_2)_5$ | —CN | 139 |
| 251 | 3-$CF_3$—Ph | 4-$OCF_3$—Ph | H | $(CH_2)_{10}$ | —CN | 100 |
| 252 | 3-$CF_3$—Ph | 4-$OCF_3$—Ph | H | cyclopropyl —C< | —$SCH_3$ | 142 |
| 253 | 4-$CF_3$—Ph | 4-$OCF_3$—Ph | H | $(CH_2)_2$ | —$CONH_2$ | 203 |
| 254 | 3-$OCH_3$—Ph | 4-$OCF_3$—Ph | H | $CH_2$ | —O—Ph-4-CN | 180 |
| 255 | 3-$OCH_3$—Ph | 4-$OCF_3$—Ph | H | $CH_2$ | —NHCHO | 180 |
| 256 | 3-$OCH_3$—Ph | 4-$OCF_3$—Ph | H | $CH_2$ | —NHCO—Ph | 181 |
| 257 | 3-$OCH_3$—Ph | 4-$OCF_3$—Ph | H | $CH_2$ | —NHCO—Ph-4-$CH_3$ | 189 |
| 258 | Ph | 4-Cl—Ph | H | — | —$SCH_3$ | 114 |
| 259 | Ph | 4-Cl—Ph | H | — | —$SCH_2$—Ph—$CO_2C_4H_9$-t | 150 |
| 260 | Ph | 4-Cl—Ph | H | — | —$SO_2CH_3$ | 191 |
| 261 | Ph | 4-Cl—Ph | H | — | —$SCH_2$—Ph-4-$NO_2$ | 133 |
| 262 | Ph | 4-Cl—Ph | H | — | —$SOCH_3$ | 159 |
| 263 | Ph | 4-Cl—Ph | H | $CH_2$ | —$NO_2$ | 181 |
| 264 | Ph | 4-$OCF_3$—Ph | H | — | —C(CH$_3$)=NOCH$_2$CH=CHCH$_3$ | 130 |
| 265 | Ph | 4-$OCF_3$—Ph | H | — | —C(CH$_3$)=NO—$C_4H_9$-n | 115 Z-FORM |
| 266 | Ph | 4-$OCF_3$—Ph | H | — | —C(CH$_3$)=NO—$C_4H_9$-n | 179 E-FORM |

TABLE 1-continued ($R^1$ = H, W = 0, Ph = phenyl)

| No. | $Ar^1$ | $Ar^2$ | $R^2$ | $(B)_n$ | Q | Melting point (°C.) |
|---|---|---|---|---|---|---|
| 267 | Ph | 4-$OCF_3$—Ph | H | — | —C(CH$_3$)=NOH | 212 |
| 268 | Ph | 4-$OCF_3$—Ph | H | — | —CH=NOH | 164 |
| 269 | Ph | 4-$OCF_3$—Ph | H | — | —C(CH$_3$)=NO—$C_3H_7$-i | 60 Z-FORM |
| 270 | Ph | 4-$OCF_3$—Ph | H | — | —C(CH$_3$)=NO—$C_3H_7$-i | 142 E-form |
| 271 | Ph | 4-$OCF_3$—Ph | H | — | —CH=NO—$C_3H_7$-i | 150 |
| 272 | Ph | 4-$OCF_3$—Ph | H | — | —CH=NNHCO$_2$C$_2$H$_5$ | 100 |
| 273 | Ph | 4-$OCF_3$—Ph | H | — | —CH=NOCH$_2$C≡CH | 169 E-form |
| 274 | Ph | 4-$OCF_3$—Ph | H | — | —CH=NOCH$_2$C≡CH | 115 Z-form |
| 275 | Ph | 4-$OCF_3$—Ph | CH$_3$ | — | —SCH$_3$ | paste |
| 276 | Ph | 4-$OCF_3$—Ph | H | — | —SCH$_3$ | 105 |
| 277 | Ph | 4-$OCF_3$—Ph | H | — | —SOCH$_3$ | 136 |
| 278 | Ph | 4-$OCF_3$—Ph | H | — | —SC$_3$H$_7$-i | 122 |
| 279 | Ph | 4-$OCF_3$—Ph | H | — | —SOC$_3$H$_7$-i | paste |
| 280 | Ph | 4-$OCF_3$—Ph | H | — | —SO$_2$C$_3$H$_7$-i | 124 (decomp.) |
| 281 | Ph | 4-$OCF_3$—Ph | H | — | —SCH$_2$CH=CH$_2$ | paste |
| 282 | Ph | 4-$OCF_3$—Ph | H | — | —SCH$_2$C≡CH | 85 |
| 283 | Ph | 4-$OCF_3$—Ph | H | — | —SCH$_2$CO$_2$CH$_3$ | 80 |
| 284 | Ph | 4-$OCF_3$—Ph | H | — | —S(CH$_2$)$_3$COCH$_3$ | paste |
| 285 | Ph | 4-$OCF_3$—Ph | H | CH$_2$ | —SO$_2$N(CH$_3$)—Ph | 157 |
| 286 | Ph | 4-$OCF_3$—Ph | H | CH$_2$ | —SO$_2$N(CH$_3$)—C$_4$H$_9$-n | 180 |
| 287 | Ph | 4-$OCF_3$—Ph | H | CH$_2$ | —ON=C(CH$_3$)$_2$ | 140 |
| 288 | Ph | 4-$OCF_3$—Ph | H | CH$_2$ | —P(O)(OCH$_3$)$_2$ | 153 |
| 289 | Ph | 4-$OCF_3$—Ph | H | CH$_2$ | —SO$_2$N(morpholino) 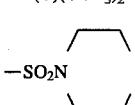 | 222 |
| 290 | Ph | 4-$OCF_3$—Ph | H | CH$_2$ | —SO$_2$N(CH$_3$)$_2$ | 210 |
| 291 | Ph | 4-$OCF_3$—Ph | H | CH$_2$ | —S-(pyrimidinyl) 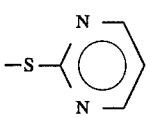 | 145 |
| 292 | Ph | 4-$OCF_3$—Ph | H | $(CH_2)_2$ | —CONH—Ph-4-$OCF_3$ | 237 |
| 293 | Ph | 4-$OCF_3$—Ph | H | $(CH_2)_2$ | —CONH$_2$ | 203 |
| 294 | Ph | 4-$OCF_3$—Ph | H | CH=CH | —CONH—Ph-4-$OCF_3$ | 231 |
| 295 | 3-Cl—Ph | 4-Cl—Ph | CH$_3$ | — | —S—Ph-4-Cl | 148 |
| 296 | 3-Cl—Ph | 4-Cl—Ph | CH$_3$ | — | —S—Ph | 128 |
| 297 | 3-Cl—Ph | 4-Cl—Ph | H | $(CH_2)_2$ | —CONH$_2$ | 206 |
| 298 | 3-Cl—Ph | 4-Br—Ph | H | $(CH_2)_2$ | —CONH$_2$ | 214 |
| 299 | 3-Cl—Ph | 4-F—Ph | H | $(CH_2)_2$ | —CONH$_2$ | 201 |
| 300 | 3-Cl—Ph | 3,5-$Cl_2$—Ph | H | $(CH_2)_2$ | —CONH$_2$ | 193 |
| 301 | 3-Cl—Ph | 4-CN—Ph | H | $(CH_2)_2$ | —CONH$_2$ | 219 |
| 302 | 3-Cl—Ph | 4-$NO_2$—Ph | H | $(CH_2)_2$ | —CONH$_2$ | 232 |
| 303 | 3-Cl—Ph | 4-$CF_3$—Ph | H | $(CH_2)_2$ | —CONH$_2$ | 218 |
| 304 | 3-Cl—Ph | 4-$CF_3$—Ph | CH$_3$ | — | —S—Ph | 130 |
| 305 | 3-Cl—Ph | 4-$OC_3H_7$-i-Ph | H | $(CH_2)_2$ | —CONH$_2$ | 202 |
| 306 | 3-Cl—Ph | 4-$SCH_3$—Ph | H | $(CH_2)_2$ | —CONH$_2$ | 210 |
| 307 | 3-Cl—Ph | 4-$SCF_3$—Ph | H | $(CH_2)_2$ | —CONH$_2$ | 228 |
| 308 | 3-Cl—Ph | 4-$OCHF_2$—Ph | H | $(CH_2)_2$ | —CONH$_2$ | 210 |

TABLE 1-continued ($R^1$ = H, W = 0, Ph = phenyl)

| No. | $Ar^1$ | $Ar^2$ | $R^2$ | $(B)_n$ | Q | Melting point (°C.) |
|---|---|---|---|---|---|---|
| 309 | 3-Cl—Ph | 4-OCHF$_2$—Ph | CH$_3$ | — | —S—Ph | 96 |
| 310 | 3-Cl—Ph | 4-OCF$_3$—Ph | H | — | —CON(piperidine-N-COCF$_3$) | paste |
| 311 | 3-Cl—Ph | 4-OCF$_3$—Ph | CH$_3$ | — | —S—Ph-4-Cl | 119 |
| 312 | 3-Cl—Ph | 4-OCF$_3$—Ph | CH$_3$ | — | —S—Ph | 107 |
| 313 | 3-Cl—Ph | 4-OCH$_3$—Ph | H | (CH$_2$)$_2$ | —CONH$_2$ | 219 |
| 314 | 3-Br—Ph | 4-Br—Ph | H | (CH$_2$)$_2$ | —CONH$_2$ | 228 |
| 315 | 3-Br—Ph | 4-OCF$_3$—Ph | H | — | —CON(piperidine-N-CO$_2$C$_3$H$_7$-i) | 117 |
| 316 | 3-Br—Ph | 4-OCF$_3$—Ph | H | — | —CON(piperidine-N-CO$_2$CH$_3$) | 121 |
| 317 | 3-Br—Ph | 4-OCF$_3$—Ph | H | — | —CON(piperidine-N-SO$_2$CH$_3$) | 107 |
| 318 | 3-Br—Ph | 4-OCF$_3$—Ph | H | — | —CON(CH$_3$)$_2$ | paste |
| 319 | 3-Br—Ph | 4-OCF$_3$—Ph | H | — | —CONH—C(CH$_3$)(CN)—C$_3$H$_7$-i | paste |
| 320 | 3-CF$_3$—Ph | 4-OCF$_3$—Ph | H | — | —CON(piperidine-N-CONH$_2$) | 201 |
| 321 | 3-Br—Ph | 4-OCF$_3$—Ph | H | — | —CON(morpholine) | 171 |
| 322 | 3-CF$_3$—Ph | 4-OCF$_3$—Ph | H | — | —CON(3,5-dimethylpiperidine) | 147 |
| 323 | 3-Br—Ph | 4-OCF$_3$—Ph | H | — | —CON(CH$_3$)CH$_2$CO$_2$CH$_3$ | paste |
| 324 | 3-Br—Ph | 4-OCF$_3$—Ph | H | — | —CON(CH$_3$)C$_6$H$_{13}$-n | paste |
| 325 | 3-F—Ph | 4-OCF$_3$—Ph | H | — | —CON(CH$_3$)$_2$ | 174 |
| 326 | 3-F—Ph | 4-OCF$_3$—Ph | H | (CH$_2$)$_2$ | —CONH$_2$ | 196 |
| 327 | 4-F—Ph | 4-OCF$_3$—Ph | H | (CH$_2$)$_2$ | —CONH$_2$ | 206 |
| 328 | 3-CF$_3$—Ph | 4-Br—Ph | H | (CH$_2$)$_2$ | —CONH$_2$ | 208 |
| 329 | 3-CF$_3$—Ph | 4-NO$_2$—Ph | H | (CH$_2$)$_2$ | —CONH$_2$ | 246 |
| 330 | 3-CF$_3$—Ph | 4-OC$_3$H$_7$-i-Ph | H | (CH$_2$)$_2$ | —CONH$_2$ | 234 |
| 331 | 3-CF$_3$—Ph | 4-OCH$_3$—Ph | H | (CH$_2$)$_2$ | —CONH$_2$ | 225 |
| 332 | 3-CF$_3$—Ph | 4-SCF$_3$—Ph | H | (CH$_2$)$_2$ | —CONH$_2$ | 230 |

TABLE 1-continued ($R^1$ = H, W = 0, Ph = phenyl)

| No. | $Ar^1$ | $Ar^2$ | $R^2$ | $(B)_n$ | Q | Melting point (°C.) |
|---|---|---|---|---|---|---|
| 333 | 3-$CF_3$—Ph | 4-$OCF_3$—Ph | H | — | —CON⟨ ⟩$NCH_2C≡CH$ | paste |
| 334 | 3-$CF_3$—Ph | 4-$OCHF_2$—Ph | H | $(CH_2)_2$ | —$CONH_2$ | 209 |
| 335 | 3-$CF_3$—Ph | 4-$OCF_3$—Ph | $CH_3$ | — | —CON⟨ ⟩$NC=NCH_3$ \| $SCH_3$ | paste |
| 336 | 3-$CF_3$—Ph | 4-$OCF_3$—Ph | H | — | —CON⟨ ⟩$NCH_2CONH_2$ | 221 |
| 337 | 3-$CF_3$—Ph | 4-$CF_3$—Ph | H | $(CH_2)_2$ | —$CONH_2$ | 233 |
| 338 | 4-$OCH_3$—Ph | 4-$OCF_3$—Ph | H | — | —C=$NOCH_3$ \| $CH_3$ | 150 |
| 339 | 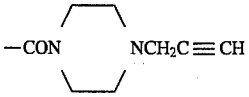 | 4-$OCF_3$—Ph | H | $(CH_2)_2$ | —$CONH_2$ | 230 |

Table 2 shows $^1$H-NMR data of compounds having physical properties expressed by the word "paste" or "vitreous" in Table 1.

TABLE 2

| No. | $^1$H—NMR [$CDCl_3$/TMS, δ value (ppm)] |
|---|---|
| 19 | 1.70(bs, 1H), 2.65–3.85(m, 8H), 7.16–7.75(m, 10H), 8.25(bs, 1H). |
| 21 | 2.25–3.90(m, 8H), 3.51(s, 2H), 7.15–7.70(m, 14H), 8.22(bs, 1H), 8.32(bs, 1H). |
| 82 | 1.57(d, 3H), 3.89(q, 1H), 7.10–7.60(m, 9H), 8.03 (bs, 1H), 8.34(bs, 1H). |
| 86 | 1.19–1.48(m, 4H), 3.99(s, 2H), 7.13–7.90(m, 14H), 8.27(bs, 1H), 8.73(bs, 1H). |
| 87 | 1.11–1.40(m, 4H), 3.79(s, 2H), 7.10–7.60(m, 15H), 8.22(bs, 1H). |
| 89 | 1.77(d, 3H), 2.84(s, 3H), 2.97(s, 3H), 4.14(q, 1H), 7.12–7.68(m, 9H), 9.21(bs, 1H). |
| 90 | 1.17–1.45(m, 4H), 2.10+2.30(s, 3H), 7.15–7.90(m, 9H), 8.27+8.34+8.42+8.78(bs, 2H). |
| 96 | 2.97(d, 3H), 6.75(m, 1H), 7.13–7.57(m, 8H), 7.92 (bs, 1H), 8.23(bs, 1H). |
| 98 | 1.04(t, 3H), 1.32(t, 3H), 3.18(q, 2H), 3.60(q, 2H), 7.18–7.70(m, 8H), 8.18(bs, 1H), 8.27(bs, 1H). |
| 100 | 0.98(t, 3H), 1.62(m, 2H), 3.33(q, 2H), 6.75(t, 1H), 7.11–7.53(m, 8H), 7.93(bs, 1H), 8.25(bs, 1H). |
| 103 | 1.10–2.12(m, 10H), 3.88(m, 1H), 6.60(bd, 1H), 7.10–7.56(m, 8H), 7.96(bs, 1H), 8.19(bs, 1H). |
| 104 | 0.95–1.96(m, 10H), 2.72+3.03(s, 3H), 3.23+4.55(m, 1H), 7.17–7.70(m, 8H), 8.16+8.18+8.21+8.25(bs, 2H). |
| 105 | 1.23(t, 3H), 2.53(m, 1H), 3.12(m, 2H), 3.45(m, 2H), 4.11(q, 2H), 4.40(m, 2H), 7.19–7.68(m, 8H), 8.18(bs, 1H), 8.62(bs, 1H). |
| 106 | 3.22–3.87(m, 8H), 7.18–7.95(m, 8H), 8.17(bs, 1H), 8.96(bs, 1H). |
| 107 | 1.70(bs, 1H), 2.60–3.90(m, 8H), 7.10–7.70(m, 9H), 8.15(bs, 1H). |
| 108 | 3.20–3.85(m, 8H), 3.73(s, 3H), 7.18–7.79(m, 8H), 8.15(bs, 1H), 8.54(bs, 1H). |
| 109 | 2.07+2.24(s, 3H), 3.20–3.90(m, 8H), 7.20–7.70(m, 8H), 8.15+8.55+8.58(bs, 2H). |
| 111 | 1.15(t, 3H), 3.20–3.87(m, 10H), 4.41(bt, 1H), 7.18–7.70(m, 8H), 8.17(bs, 1H), 8.56(bs, 1H). |
| 112 | 1.12(t, 6H), 3.05–3.85(m, 8H), 3.22(q, 4H), 7.18–7.70(m, 8H), 8.17(bs, 1H), 8.62(bs, 1H). |
| 160 | 3.92(s, 3H), 7.08–7.64(m, 8H), 8.23(bs, 1H), 11.50(bs, 1H). |
| 163 | 2.97(d, 3H), 6.70(bq. 1H), 7.15–7.58(m, 8H), 7.92 (bs, 1H), 8.11(bs, 1H). |
| 165 | 1.02(t, 3H), 1.30(t, 3H), 3.18(q, 2H), 3.61(q, 2H), 7.10–7.72(m, 8H), 8.19(bs, 2H). |
| 178 | 2.90(s, 3H), 3.18(s, 3H), 7.18–7.92(m, 8H), 8.16 (bs, 1H), 8.37(bs, 1H). |
| 181 | 7.12–8.05(m, 13H), 7.89(bs, 1H), 8.08(bs, 1H), 11.90(bs, 1H). |
| 185 | 3.22–3.80(m, 11H), 7.18–7.91(m, 8H), 8.18(bs, 1H), 9.12(bs, 1H). |
| 190 | 3.01+3.13(s, 3H), 4.34+4.53(s, 2H), 7.21–8.26(m, 8H), 7.92(bs, 1H), 9.86(bs, 1H). |
| 196 | 1.08+1.38(d, 3H), 3.07–5.10(m, 6H), 7.13–7.97(m, 8H), 8.18+8.20(bs, 1H), 9.25+9.28(bs, 1H). |
| 237 | 1.19+1.87(d, 3H), 5.34+5.64(q, 1H), 7.80–8.20(m, 12H), 7.75+8.05+9.63+10.20(bs, 1H). |
| 239 | 1.29(d, 3H), 2.72(dd, 1H), 3.20–3.90(m, 10H), 7.10–8.30(m, 9H), 9.94(bs, 1H). |
| 244 | 1.25(t, 3H), 1.42(d, 3H), 2.80–3.00(m, 1H), 4.10–4.30(m, 2H), 7.10–7.80(m, 8H), 7.51(bs, 1H), 8.40 (bs, 1H). |
| 247 | 1.10–1.95(m, 4H), 1.22(t, 3H), 4.22(q, 2H), 7.80–8.30(m, 8H), 7.97(bs, 1H), 8.65(bs, 1H). |
| 275 | 2.19(s, 3H), 3.40(s, 3H), 7.10–7.16(m, 2H), 7.45–7.60(m, 7H), 7.87(bs, 1H). |
| 279 | 1.27+1.34(d, 3H), 1.31+1.46(d, 3H), 2.68+3.22 |

TABLE 2-continued

| No. | $^1$H—NMR [CDCl$_3$/TMS, δ value (ppm)] |
|---|---|
|  | (septet, 1H), 7.15–7.20(m, 2H), 7.35–7.66(m, 7H), 8.03+8.31(bs, 1H), 8.90+12.27(bs, 1H). (Z:E=3:2) |
| 281 | 4.73(d, 2H), 4.92–5.04(m, 2H), 5.60–5.75(m, 1H), 7.15–7.20(m, 2H), 7.43–7.74(m, 7H), 8.12(bs, 1H), 8.71(bs, 1H). |
| 284 | 1.73(m, 2H), 2.08(s, 3H), 2.46(t, 2H), 2.70(t, 2H), 7.12–7.17(m, 2H), 7.41–7.77(m, 9H), 8.11(bs, 1H), 8.17(bs, 1H). |
| 310 | 3.26–3.85(m, 8H), 7.21–7.65(m, 8H), 8.19(bs, 1H), 9.47(bs, 1H). |
| 318 | 2.89(s, 3H), 3.11(s, 3H), 7.18–7.81(m, 8H), 8.20 (bs, 1H), 8.85(bs, 1H). |
| 319 | 1.02–1.06(m, 6H), 2.45(septet, 1H), 7.16–7.74(m, 8H), 8.60(bs, 1H), 9.58(bs, 1H), 10.05(bs, 1H). |
| 323 | 2.86(s, 3H), 3.87(s, 3H), 4.30(s, 2H), 7.16–7.87 (m, 8H), 8.21(bs, 1H), 9.32(bs, 1H). |
| 324 | 0.76–1.41(m, 11H), 2.81(bt, 2H), 3.08(s, 3H), 7.20–7.81(m, 8H), 8.17(bs, 1H), 8.50(bs, 1H). |
| 333 | 2.28(t, 1H), 2.43(t, 2H), 2.66(t, 2H), 3.27–3.33 (m, 4H), 3.86(t, 2H), 7.17–7.23(m, 2H), 7.54–7.88 (m, 6H), 8.17(bs, 1H), 8.79(bs, 1H). |
| 335 | 2.29(s, 3H), 2.80–3.05(m, 2H), 3.19(s, 3H), 3.25– 3.35(m, 4H), 3.50(s, 3H), 3.55–3.70(m, 2H), 7.18– 7.24(m, 2H), 7.50–7.89(m, 6H), 8.72(s, 1H). |

Porduction process 4.

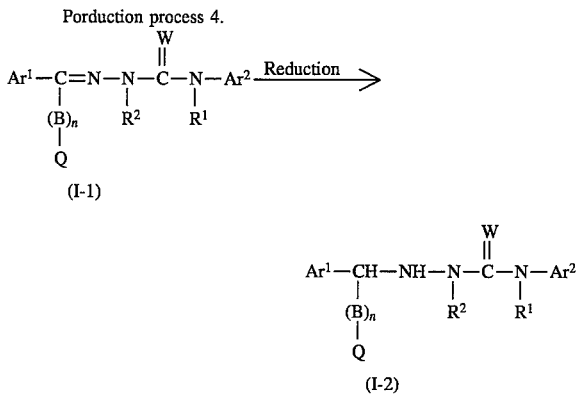

wherein Ar$^1$, Ar$^2$, R$^1$, R$^2$, B, n, Q and W are as defined above).

A hydrazine derivative of the general formula (I-2) can be produced by reducing a hydrazine derivative of the general formula (I-1) in the presence of a reducing agent.

This reduction reaction can be carried out by the use of a suitable reducing agent, or it can be carried out by catalytic reduction in the presence of a suitable catalyst. As the reducing agent, there can be used, for example, NaBH$_3$CN and NaBH$_4$.

The amount of the reducing agent used may be chosen so that its number of moles in terms of the number of moles of hydride as reducing agent may be equal to or larger than that of the hydrazine derivative of the general formula (I-1).

As an inert solvent usable in the reaction, any inert solvent may be used so long as it does not markedly inhibit the progress of the reaction. There can be exemplified alcohols such as methanol, ethanol, propanol, butanol, etc.; chain ethers such as diethyl ether, etc.; cyclic ethers such as dioxane, tetrahydrofuran, etc.; Cellosolves such as Methyl Cellosolve, etc.; esters such as ethyl acetate, etc.; aromatic hydrocarbons such as benzene, toluene, xylene, etc.; halogenated hydrocarbons such as dichloromethane, chloroform, carbon tetrachloride, etc.; diglyme; dimethylformamide; dimethylacetamide; dimethyl sulfoxide; sulfolane; and water. These inert solvents may be used singly or as a mixture thereof.

The reaction is carried out under acidic or neutral conditions in the pH range of 1 to 7. The pH is preferably in the range of 4 to 6 and is adjusted by adding hydrogen chloride, hydrogen bromide or the like to the reaction system.

It is also possible to carry out the reaction in the presence of a Lewis acid such as titanium tetrachloride (TiCl$_4$) in the reaction system for the purpose of accelerating the reaction.

The reaction temperature may be properly chosen in the range of –20° C. to the boiling point of the inert solvent used.

Although the reaction time is varied depending on the degree of the reaction, the reaction temperature, etc., it is several minutes to 48 hours.

After completion of the reaction, the desired compound is isolated from a reaction solution containing the desired compound by a conventional method such as distilling-off of the solvent, solvent extraction, or the like, and if necessary, purified by recrystallization, column chromatography, etc., whereby the desired compound can be produced.

When catalytic reduction is carried out as the reduction reaction, it is carried out according to, for example, the conventional method described in Shin Jikken Kagaku Koza, Vol. 15-II, Maruzen Co., Ltd., etc. As an inert solvent usable in this case, there can be exemplified alcohols such as methanol, ethanol, propanol, butanol, etc.; Cellosolves such as Methyl Cellosolve, etc.; cyclic ethers such as dioxane, tetrahydrofuran, etc.; hydrocarbons such as hexane, cyclohexane, etc.; fatty acids or esters thereof, such as acetic acid, ethyl acetate, etc.; and amides such as N,N-dimethylformamide, 1,3-dimethyl-2-imidazolidinone, N-methylpyrrolidone, etc. These inert solvents may be used singly or as a mixture thereof.

As the catalyst used in the reaction, there can be used typical catalysts for catalytic reduction, for example, palladium-carbon, palladium black, platinum dioxide and Raney nickel. The amount of the catalyst used may be properly chosen in the range of 0.0001 to 20% by weight based on the weight of the hydrazine derivative of the general formula (I-1).

The hydrogen pressure in the reaction can be chosen in the range of atmospheric pressure to 300 atmospheres, and is preferably in the range of atmospheric pressure to 50 atmospheres.

The reaction temperature may be properly chosen in the range of room temperature to the boiling point of the inert solvent used, and is preferably in the range of room temperature to 80° C.

Although the reaction time is varied depending on the degree of the reaction, the reaction temperature, etc., it is several minutes to 80 hours.

After completion of the reaction, a reaction solution containing the desired compound is treated in the same manner as in the case of using the reducing agent, whereby the desired compound can be produced.

Examples of the hydrazine derivative of the general formula (I-2) produced by production process 4 are given in Table 3 but they are not intended in any way to limit the scope of the present invention.

General formula (I-2):

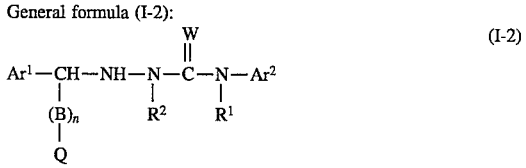

TABLE 3

($R^1$, $R^2$ = H, W = O)

| No. | $Ar^1$ | $Ar^2$ | $(B)_n$ | Q | Melting point (°C.) |
|---|---|---|---|---|---|
| 340 | Ph | 4-OCF$_3$—Ph | CH$_2$ | —CN | 169 |
| 341 | Ph | 4-OCF$_3$—Ph | CH$_2$ | —O—Ph-4-NO$_2$ | 138 |
| 342 | Ph | 4-OCF$_3$—Ph | CH$_2$ | —O—Ph-4-CN | 176 |
| 343 | Ph | 4-OCF$_3$—Ph | CH$_2$ | —SCH$_3$ | 174 |
| 344 | Ph | 4-OCF$_3$—Ph | CH$_2$ | —SCH$_2$Cl≡CH | 157 |
| 345 | Ph | 4-OCF$_3$—Ph | CH$_2$ | —SCH$_2$CO$_2$CH$_3$ | 143 |
| 346 | Ph | 4-OCF$_3$—Ph | CH$_2$ | —S—Ph-4-Cl | 188 |
| 347 | Ph | 4-OCF$_3$—Ph | CH$_2$ | —S—Ph-4-NO$_2$ | 167 |
| 348 | Ph | 4-OCF$_3$—Ph | CH$_2$ | —CO$_2$C$_2$H$_5$ | 186 |
| 349 | Ph | 4-OCF$_3$—Ph | CH$_2$ | —NHCOCH$_3$ | 202 |
| 350 | Ph | 4-OCF$_3$—Ph | CH$_2$ | —NHCO—Ph | 227 |
| 351 | Ph | 4-OCF$_3$—Ph | CH$_2$ | —NHCO—Ph-2,4-Cl$_2$ | 180 |
| 352 | Ph | 4-OCF$_3$—Ph | CH$_2$ | —NHCO—Ph-4-NO$_2$ | 227 |
| 353 | Ph | 4-OCF$_3$—Ph | CH$_2$ | —NHCONHC$_2$H$_5$ | 160 |
| 354 | Ph | 4-OCF$_3$—Ph | (CH$_2$)$_2$ | —CN | 168 |
| 355 | Ph | 4-OCF$_3$—Ph | (CH$_2$)$_2$ | —OC$_2$H$_5$ | 162 |
| 356 | Ph | 4-OCF$_3$—Ph | —C—(cyclopropyl) | —SCH$_3$ | paste |
| 357 | Ph | 4-OCF$_3$—Ph | —C(CH$_3$)$_2$— | —CN | 171 |
| 358 | 3-Cl—Ph | 4-OCF$_3$—Ph | CH$_2$ | —O—Ph-3-NO$_2$ | 70 |
| 359 | 3-Cl—Ph | 4-OCF$_3$—Ph | CH$_2$ | —O—Ph-4-NO$_2$ | 160 |
| 360 | 3-Cl—Ph | 4-OCF$_3$—Ph | CH$_2$ | —O—Ph-4-SCH$_3$ | paste |
| 361 | 3-Cl—Ph | 4-OCF$_3$—Ph | (CH$_2$)$_2$ | —CN | 174 |
| 362 | 3-Cl—Ph | 4-OCF$_3$—Ph | (CH$_2$)$_2$ | —CONH$_2$ | 164 |
| 363 | 3-Cl—Ph | 4-OCF$_3$—Ph | (CH$_2$)$_2$ | —CON(C$_2$H$_5$)$_2$ | 132 |
| 364 | 3-Cl—Ph | 4-OCF$_3$—Ph | (CH$_2$)$_2$ | —CONHCH$_2$CH=CH$_2$ | 148 |
| 365 | 3-Cl—Ph | 4-OCF$_3$—Ph | (CH$_2$)$_2$ | —CON(piperazinyl-NCH$_3$) | 113 |
| 366 | 3-Cl—Ph | 4-OCF$_3$—Ph | CH$_2$CH(CH$_3$) | —CN | paste |
| 367 | 3-Cl—Ph | 4-OCF$_3$—Ph | (CH$_2$)$_4$ | —CN | 165 |
| 368 | 4-Cl—Ph | 4-OCF$_3$—Ph | CH$_2$ | —O—Ph-4-NO$_2$ | 200 |
| 369 | 4-Cl—Ph | 4-OCF$_3$—Ph | CH$_2$ | —O—Ph-4-CN | 200 |
| 370 | 4-Cl—Ph | 4-OCF$_3$—Ph | CH$_2$ | —S—Ph-4-NO$_2$ | 180 |
| 371 | 4-Cl—Ph | 4-OCF$_3$—Ph | CH$_2$ | —S—Ph-4-CH$_3$ | 190 |
| 372 | 4-Cl—Ph | 4-OCF$_3$—Ph | CH$_2$ | —NHCO—Ph | 230 |
| 373 | 4-Cl—Ph | 4-OCF$_3$—Ph | (CH$_2$)$_4$ | —CN | 168 |
| 374 | 4-Br—Ph | 4-OCF$_3$—Ph | CH$_2$ | —O—Ph-4-CN | 190 |
| 375 | 3-NO$_2$—Ph | 4-OCF$_3$—Ph | CH$_2$ | —O—Ph-4-CN | 190 |
| 376 | 3-CH$_3$—Ph | 4-OCF$_3$—Ph | CH$_2$ | —O—Ph-4-CN | 155 |
| 377 | 3-CF$_3$—Ph | 4-OCF$_3$—Ph | CH$_2$ | —O—Ph-4-CN | paste |
| 378 | 3-CF$_3$—Ph | 4-OCF$_3$—Ph | CH$_2$ | —SC$_3$H$_7$-i | 127 |
| 379 | 3-CF$_3$—Ph | 4-OCF$_3$—Ph | CH$_2$ | —SCH$_2$-cyclopropyl | 108 |
| 380 | 3-CF$_3$—Ph | 4-OCF$_3$—Ph | CH$_2$ | —SCH$_2$CH=CH$_2$ | 107 |
| 381 | 3-CF$_3$—Ph | 4-OCF$_3$—Ph | CH$_2$ | —SCH$_2$CH$_2$CN | 80 |
| 382 | 3-CF$_3$—Ph | 4-OCF$_3$—Ph | CH$_2$ | —SCH$_2$CO$_2$CH$_3$ | 95 |
| 383 | 3-CF$_3$—Ph | 4-OCF$_3$—Ph | CH$_2$ | —SCH$_2$CH$_2$CO$_2$CH$_3$ | 100 |
| 384 | 3-CF$_3$—Ph | 4-OCF$_3$—Ph | CH$_2$ | —SCH$_2$CONHC$_4$H$_9$-t | 70 |
| 385 | 3-CF$_3$—Ph | 4-OCF$_3$—Ph | CH$_2$ | —CO$_2$C$_2$H$_5$ | 135 |
| 386 | 3-CF$_3$—Ph | 4-OCF$_3$—Ph | CH$_2$ | —NHCO—Ph | 199 |
| 387 | 3-CF$_3$—Ph | 4-OCF$_3$—Ph | CH$_2$ | —NHCO—Ph-2-Cl | 195 |
| 388 | 3-CF$_3$—Ph | 4-OCF$_3$—Ph | CH$_2$ | —NHCO—Ph-4-NO$_2$ | 193 |
| 389 | 3-CF$_3$—Ph | 4-OCF$_3$—Ph | (CH$_2$)$_2$ | —CN | 173 |
| 390 | 3-CF$_3$—Ph | 4-OCF$_3$—Ph | (CH$_2$)$_2$ | —CONH$_2$ | 135 |
| 391 | 3-CF$_3$—Ph | 4-OCF$_3$—Ph | (CH$_2$)$_3$ | —CN | 135 |

TABLE 3-continued ($R^1$, $R^2$ = H, W = O)

| No. | $Ar^1$ | $Ar^2$ | $(B)_n$ | Q | Melting point (°C.) |
|---|---|---|---|---|---|
| 392 | 3-$CF_3$—Ph | 4-$OCF_3$—Ph | $CH_2CH(CH_3)$ | —CN | paste |
| 393 | 3-$CF_3$—Ph | 4-$OCF_3$—Ph | $CH_2CH(CH_3)$ | —$CONH_2$ | 159 |
| 394 | 3-$CF_3$—Ph | 4-$OCF_3$—Ph | —C— (cyclopropyl) | —$SCH_3$ | paste |
| 395 | 3-$CF_3$—Ph | 4-$OCF_3$—Ph | $(CH_2)_4$ | —CN | 134 |
| 396 | 3-$CF_3$—Ph | 4-$OCF_3$—Ph | $(CH_2)_4$ | —$CONH_2$ | 180 |
| 397 | 3-$CF_3$—Ph | 4-$OCF_3$—Ph | $(CH_2)_5$ | —CN | 129 |
| 398 | 3-$CF_3$—Ph | 4-$OCF_3$—Ph | $(CH_2)_{10}$ | —CN | 113 |
| 399 | 3-$OCH_3$—Ph | 4-$OCF_3$—Ph | $CH_2$ | —O—Ph-4-CN | 185 |
| 400 | Ph | 4-$OCF_3$—Ph | $CH_2$ | —S-(pyrimidinyl) | 230 |
| 401 | Ph | 4-$OCF_3$—Ph | — | —CON(morpholine) | 175 |

Table 4 shows $^1$H-NMR data of compounds having physical properties expressed by the word "paste" or "vitreous" in Table 3.

TABLE 4

| No. | $^1$H—NMR [$CDCl_3$/TMS, δ value (ppm)] |
|---|---|
| 356 | 0.70–1.04(m, 4H), 1.74(s, 3H), 3.52(d, 1H), 4.51 (d, 1H), 6.08(bs, 1H), 6.95–7.55(m, 9H), 8.72(bs, 1H). |
| 360 | 2.41(s, 3H), 4.15(m, 2H), 4.33(m, 1H), 5.52(bs, 1H), 6.57(bs, 1H), 6.90–7.80(m, 12H), 8.89(bs, 1H). |
| 366 | 1.29(d, 3H), 1.70–1.90(m, 1H), 2.10–2.20(m, 1H), 2.40–2.60(m, 1H), 4.08(dt, 1H), 4.50(d, 1H), 6.35 (bs, 1H), 7.10–7.60(m, 8H), 8.15(bs, 1H). |
| 377 | 4.25(d, 2H), 4.44(m, 1H), 4.75(bs, 1H), 6.85(bs, 1H), 6.90–7.80(m, 12H), 8.08(bs, 1H). |
| 392 | 1.30(d, 3H), 1.70–1.90(m, 1H), 2.10–2.20(m, 1H), 2.40–2.60(m, 1H), 4.10(dt, 1H), 4.30(d, 1H), 6.48 (bs, 1H), 7.10–7.60(m, 8H), 8.19(bs, 1H). |
| 394 | 0.75–1.03(m, 4H), 1.62(s, 3H), 3.35(bs, 1H), 4.40 (bs, 1H), 6.30(bs, 1H), 6.96–7.53(m, 8H), 8.64 (bs, 1H). |

Production process 5.

$$Ar^1-N-N=C-C-OH \atop \underset{Q}{\overset{(B)_n}{|}} \quad \overset{W}{\underset{R^2}{\|}}$$

(XI)

$$HN-Ar^2 \atop |\ R^1$$

(XII)

Condensing agent and/or base

↓

$$Ar^1-N-N=C-C-N-Ar^2 \atop \underset{Q}{\overset{(B)_n}{|}} \quad \overset{W}{\underset{R^2}{\|}} \quad \overset{}{\underset{R^1}{|}}$$

(I-3)

wherein $Ar^1$, $Ar^2$, $R^1$, $R^2$, B, n, Q and W are as defined above).

A hydrazine derivative of the general formula (I-3) can be produced by reacting a compound of the general formula (XI) and a condensing agent with a compound of the general formula (XII) in the presence or absence of an inert solvent and/or in the presence of a base.

As the inert solvent usable in this reaction, there can be used, for example, acetone, methyl ethyl ketones, pyridine, etc. in addition to the inert solvents usable in production process 3.

As the condensing agent, there can be used, for example, halogenating agents (e.g. thionyl chloride, phosphorus trichloride and phosphorus pentachloride), carbodiimidazole, dicyclohexylcarbodiimide, and 2-chloro-1-methylpyridinium iodide. The amount of the condensing agent used may be properly chosen in the range of 1 mole to excess moles per mole of the compound of the general formula (XII).

It is also possible to carry out the reaction by addition of a catalytic amount of triethylamine, pyridine or dimethylformamide for the purpose of accelerating the reaction.

As the base used in the reaction, an inorganic base or an organic base may be used. As the inorganic base, there may be used, for example, hydroxides, carbonates or alcoholates of alkali metal atoms or alkaline earth metal atoms (e.g. sodium, potassium, magnesium and calcium), and hydrides of alkali metals, such as sodium hydride, etc. As the organic base, there may be used triethylamine, pyridine, N,N-dimethylaniline, 2,6-dimethylpyridine, 4-N,N-dimethylaminopyridine, 1,8-diazabicyclo[5,4,0]-7-undecene (DBU), etc. The amount of the base used may be chosen in the range of 1 mole to excess moles per mole of the compound of the general formula (XII).

The reaction temperature may be properly chosen in the range of room temperature to the boiling point of the inert solvent used.

Although the reaction time is varied depending on the degree of the reaction, the reaction temperature, etc., it is several minutes to 48 hours.

After completion of the reaction, the same treatment as in production process 1 is carried out, whereby the hydrazine derivative of the general formula (I-3) can be produced.

The compound of the general formula (XI) can be produced by the following process:

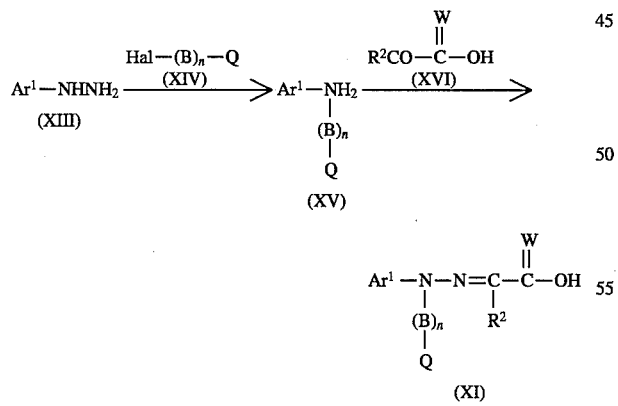

wherein $Ar^1$, $R^2$, B, n, Q, W and Hal are as defined above).

A compound of the general formula (XI) can be produced by reacting a compound of the general formula (XIII) with a halide of the general formula (XIV) to obtain a compound of the general formula (XV), and reacting the compound (XV) with a compound of the general formula (XVI) after or without isolating the compound (XV).

Production process 6.

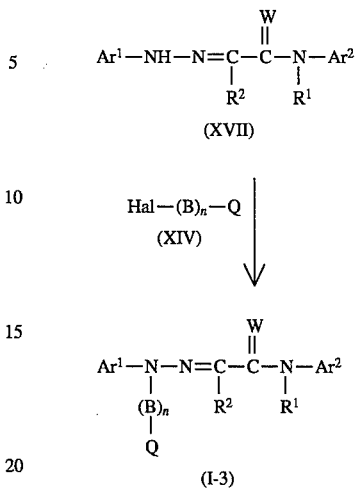

wherein $Ar^1$, $Ar^2$, $R^1$, $R^2$, B, n, Q, W and Hal are as defined above.

A hydrazine derivative of the general formula (I-3) can be produced by reacting a compound of the general formula (XVII) with a halide of the general formula (XIV) in the presence or absence of an inert solvent and in the presence of a base.

As the inert solvent and the base which are usable in this reaction, there can be used, for example, the inert solvents and bases which are exemplified in production process 4. The amount of the base used may be chosen in the range of 1 mole to excess moles per mole of the compound of the general formula (XIV).

Since the reaction is an equimolar reaction, it is sufficient that the reactants are used in equimolar amounts, though either of them may be used in excess.

The reaction temperature may be chosen in the range of 0° C. to the boiling point of the inert solvent used.

Although the reaction time is varied depending on the degree of the reaction, the reaction temperature, etc., it may be chosen in the range of several minutes to 48 hours.

After completion of the reaction, a reaction solution containing the desired compound is treated in the same manner as, for example, in production process 1, whereby the hydrazine derivative of the general formula (I-3) can be produced.

The compound of the general formula (XVII) used in the reaction can be produced by the following process:

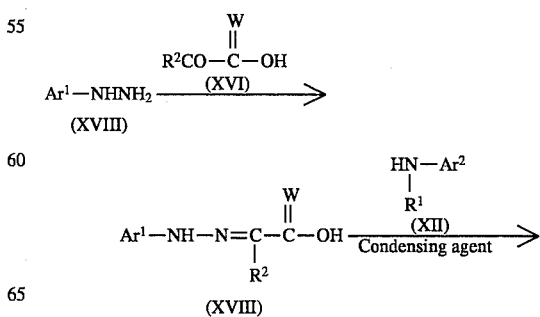

-continued

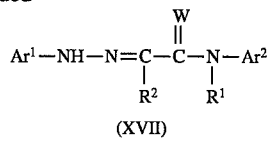

(XVII)

wherein $Ar^1$, $Ar^2$, $R^1$, $R^2$, and W are as defined above.

The compound of the general formula (XVII) can be produced by reacting a compound of the general formula (XIII) with a compound of the general formula (XVI) to obtain a compound of the general formula (XVIII), and reacting the compound (XVIII) with a compound of the general formula (XII) after or without isolating the compound (XVIII).

Typical examples of the hydrazine derivatives of the general formula (I-3) produced by production processes 5 and 6 are given in Table 5 but they are not intended in any way to limit the scope of the present invention.

General formula (I-3)

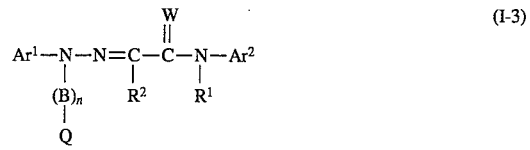
(I-3)

TABLE 5

($R^1$, $R^2$ = H, W = O)

| No. | $Ar^1$ | $Ar^2$ | $(B)_n$ | Q | Melting point (°C.) |
|---|---|---|---|---|---|
| 402 | Ph | 4-$OCF_3$—Ph | — | —CO—Ph-4-CN | 144.4–148.1 |
| 403 | Ph | 4-$OCF_3$—Ph | — | —CO—Ph-4-$CH_3$ | 152–154 |
| 404 | Ph | 4-Cl—Ph | $CH_2$ | —CONH—Ph | 253–255 |
| 405 | Ph | 4-$OCF_3$—Ph | $CH_2$ | —CONH—Ph | 243–245 |
| 406 | Ph | 4-$OCF_3$—Ph | $CH_2$ | —$CO_2CH_3$ | 137.8 |
| 407 | Ph | 4-$OCF_3$—Ph | $CH_2$ | —$CO_2C_2H_5$ | 129–131 |
| 408 | Ph | 4-$OCF_3$—Ph | $(CH_2)_2$ | —SO—Ph | 118–119 |
| 409 | Ph | 4-$OCF_3$—Ph | —CH—<br>\|<br>$CH_3$ | —$CO_2CH_3$ | nD 1.5545 (20° C.) |
| 410 | 3-Cl—Ph | Ph | $CH_2$ | —CH=CH—Ph | 160.5–161.1 |
| 411 | 3-Cl—Ph | 4-Cl—Ph | $CH_2$ | —CH=CH—Ph | 178.1–180.3 |
| 412 | 3-Cl—Ph | 4-CN—Ph | $CH_2$ | —CONH—Ph-4-Cl | 252.9–253.5 |
| 413 | 3-Cl—Ph | 4-CN—Ph | $CH_2$ | —CONH—Ph-4-$OCF_3$ | 257.1 |
| 414 | 3-Cl—Ph | 4-$OCF_3$—Ph | $CH_2$ | —CH=$CH_2$ | 79–81 |
| 415 | 3-Cl—Ph | 4-$OCF_3$—Ph | $CH_2$ | —C≡CH | 126 |
| 416 | 3-Cl—Ph | 4-$OCF_3$—Ph | — | —CO—◁ | nD 1.5575 (25° C.) |
| 417 | 3-Cl—Ph | 4-$OCF_3$—Ph | — | —$SO_2$—Ph-4-Cl | 121.0–122.7 |
| 418 | 3-Cl—Ph | 4-$OCF_3$—Ph | $CH_2$ | —$OCH_3$ | 99.3 |
| 419 | 3-Cl—Ph | 4-$OCF_3$—Ph | $CH_2$ | —$CONHCH_2CN$ | 228.4 |
| 420 | 3-Cl—Ph | 4-$OCF_3$—Ph | $CH_2$ | —$CONH_2$ | 221 |
| 421 | 3-Cl—Ph | 4-$OCF_3$—Ph | $CH_2$ | —CONH—Ph | 225.4–228.0 |
| 422 | 3-Cl—Ph | 4-$OCF_3$—Ph | $CH_2$ | —CONH—Ph-3-Cl | 218.9–220.4 |
| 423 | 3-Cl—Ph | 4-$OCF_3$—Ph | $CH_2$ | —CONH—Ph-4-Cl | 227.7–229.4 |
| 424 | 3-Cl—Ph | 4-$OCF_3$—Ph | $CH_2$ | —CONH—Ph-4-Br | 244.5 |
| 425 | 3-Cl—Ph | 4-$OCF_3$—Ph | $CH_2$ | —CONH—Ph-4-$NO_2$ | 187.5 |
| 426 | 3-Cl—Ph | 4-$OCF_3$—Ph | $CH_2$ | —CONH—Ph-4-CN | 227.9–228.7 |
| 427 | 3-Cl—Ph | 4-$OCF_3$—Ph | $CH_2$ | —CONH—Ph-4-$CH_3$ | 227.6–230.9 |
| 428 | 3-Cl—Ph | 4-$OCF_3$—Ph | $CH_2$ | —CONH—Ph-4-OCH | 239–242 |
| 429 | 3-Cl—Ph | 4-$OCF_3$—Ph | $CH_2$ | —CONH—Ph-3-$CF_3$ | 188 |
| 430 | 3-Cl—Ph | 4-$OCF_3$—Ph | $CH_2$ | —CONH—Ph-4-$OCF_3$ | 218.6–220.5 |
| 431 | 3-Cl—Ph | 4-$OCF_3$—Ph | $CH_2$ | —CON⟨NO⟩ (morpholino) | 227.1 |
| 432 | 3-Cl—Ph | 4-$OCF_3$—Ph | $CH_2$ | —CH=CH—Ph | 152 |
| 433 | 3-Cl—Ph | 4-$OCF_3$—Ph | $CH_2$ | —CH=CH—Ph-4-Cl | paste E- or Z-form |
| 434 | 3-Cl—Ph | 4-$OCF_3$—Ph | $CH_2$ | —CH=CH—Ph-4-Cl | 155–156 Z- or E-form |
| 435 | 3-Cl—Ph | 4-$OCF_3$—Ph | $CH_2$ | H\\ /H<br>—C=C\\<br>C≡C—$C_4H_9$-t | 99–101 |

TABLE 5-continued (R¹, R² = H, W = O)

| No. | Ar¹ | Ar² | (B)ₙ | Q | Melting point (°C.) |
|---|---|---|---|---|---|
| 436 | 3-Cl—Ph | 4-OCF₃—Ph | CH₂ | 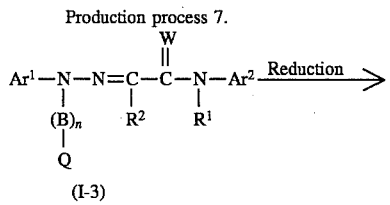 | 142–144 |
| 437 | 4-Cl—Ph | 4-Cl—Ph | CH₂ | —CONH—Ph-4-OCF₃ | 257.4–260.1 |
| 438 | 4-Cl—Ph | 4-OCF₃—Ph | CH₂ | —CONH—Ph-4-OCF₃ | 247.4 |
| 439 | 3-CF₃—Ph | 4-OCF₃—Ph | CH₂ | —CH═CH—Ph-4-CN | paste |

Table 6 shows $^1$H-NMR data of compounds having physical properties expressed by the word "paste" or "vitreous" in Table 5.

TABLE 6

| No. | $^1$H—NMR [CDCl₃/TMS, δ value (ppm)] |
|---|---|
| 433 | 3.68(d, 2H), 6.17(ddd, 1H), 6.50(d, 1H), 690–7.80(m, 12H), 8.10(s, 1H), 8.92(s, 1H). |
| 439 | 4.79(d, 2H), 6.33(ddd, 1H), 6.44(d, 1H), 6.95(s, 1H), 7.20–7.70(m, 12H), 8.55(s, 1H). |

Production process 7.

$$\underset{(I\text{-}3)}{\overset{\displaystyle Ar^1-\underset{\underset{Q}{|}}{\underset{(B)_n}{\overset{|}{N}}}-N=C-\overset{\overset{W}{\|}}{\underset{R^1}{\overset{|}{C}}}-\overset{}{\underset{}{N}}-Ar^2}{}} \xrightarrow{\text{Reduction}}$$

-continued $$\underset{(I\text{-}4)}{\overset{\displaystyle Ar^1-\underset{\underset{Q}{|}}{\underset{(B)_n}{\overset{|}{N}}}-NH-\underset{R^2}{\overset{|}{C}H}-\overset{\overset{W}{\|}}{\underset{R^1}{\overset{|}{C}}}-\overset{}{\underset{}{N}}-Ar^2}{}}$$

wherein Ar¹, Ar², R¹, R², B, n, Q and W are as defined above.

A hydrazine derivative of the general formula (I-4) can be produced by reducing a hydrazine derivative of the general formula (I-3) in the presence of a reducing agent.

This reaction is carried out in the same manner as in production process 4, whereby the hydrazine derivative of the general formula (I-4) can be produced.

Typical examples of the hydrazine derivative of the general formula (I-4) produced by production process 7 are given in Table 7 but they are not intended in any way to limit the scope of the present invention.

General formula (I-4)

$$\underset{}{\overset{\displaystyle Ar^1-\underset{\underset{Q}{|}}{\underset{(B)_n}{\overset{|}{N}}}-NH-\underset{R^2}{\overset{|}{C}H}-\overset{\overset{W}{\|}}{\underset{R^1}{\overset{|}{C}}}-\overset{}{\underset{}{N}}-Ar^2}{}} \quad (I\text{-}4)$$

TABLE 7

(R¹, R² = H, W = O)

| No. | Ar¹ | Ar² | (B)ₙ | Q | Melting point (°C.) |
|---|---|---|---|---|---|
| 440 | Ph | 4-OCF₃—Ph | CH₂ | —CONH—Ph | 180.5–180.8 |
| 441 | 3-Cl—Ph | 4-OCF₃—Ph | CH₂ | —CONH—Ph-4-OCF₃ | 171.5 |
| 442 | 3-Cl—Ph | 4-CN—Ph | CH₂ | —CONH—Ph-4-OCF₃ | 207.5–209.3 |
| 443 | 3-Cl—Ph | 4-OCF₃—Ph | CH₂ | —CONH—Ph-4-CN | 183.2–184.6 |
| 444 | 3-Cl—Ph | 4-OCF₃—Ph | CH₂ | -conh-Ph-3-CF₃ | 131.9–133.2 |
| 445 | 4-Cl—Ph | 4-OCF₃—Ph | CH₂ | —CONH—Ph-4-OCF₃ | 151–153 |
| 446 | 4-Cl—Ph | 4-OCF₃—Ph | CH₂ | —CH═CH—Ph | 99.3 |
| 447 | 4-Cl—Ph | 4-OCF₃—Ph | CH₂ | —CH═CH—Ph-4-Cl | 85–87 |
| 448 | 3-CF₃—Ph | 4-OCF₃—Ph | CH₂ | —CH═CH—Ph-4-CN | paste |
| 449 | 3-Cl—Ph | 4-OCF₃—Ph | CH₂ | 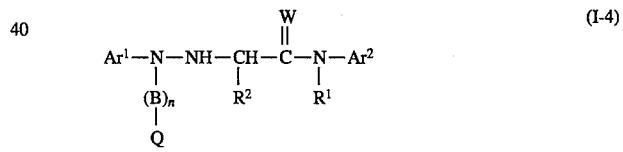 | paste |

Table 8 shows 1H-NMR data of the compounds having properties expressed by the word "paste" or "vitreous" in Table 7.

TABLE 8

| No. | $^1$H—NMR [CDCl$_3$/TMS, δ value (ppm)] |
|---|---|
| 448 | 3.75(s, 2H), 4.30(d, 2H), 6.31(ddd, 1H), 6.65(d, 1H), 7.00–7.70(m, 13H), 8.65(s, 1H). |
| 449 | 1.22(s, 9H), 3.63(s, 2H), 4.02(d, 2H), 5.73(d, 1H), 5.94(ddd, 1H), 6.90–7.50(m, 9H), 8.72(s, 1H). |

Typical examples concerning the hydrazine derivatives of the general formula (I) of the present invention are described below, but they should not be construed as limiting the scope of the invention.

EXAMPLES

Example 1

1-1. Production of α-(4-cyanophenoxy)acetophenone

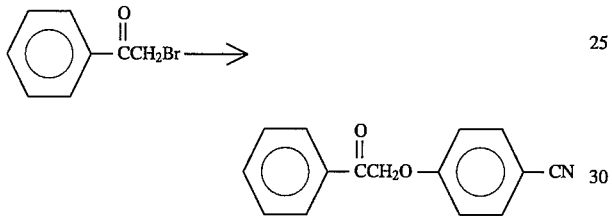

In 50 ml of acetone were dissolved 1.10 g (5.5 mmoles) of α-bromoacetophenone and 0.72 g (6.1 mmoles) of 4-cyanophenol, after which 0.76 g (5.5 mmoles) of anhydrous potassium carbonate was added to the resulting solution, and the reaction was carried out at room temperature for 2 hours.

After completion of the reaction, the solvent was removed by distillation under reduced pressure from the reaction mixture containing the desired compound. Water was added to the residue and the desired compound was extracted with ethyl acetate. The organic layer was washed with water, dried over anhydrous magnesium sulfate, and distilled under reduced pressure to remove the solvent, whereby 1.10 g of the desired compound was obtained.

Physical property: m.p. 162° C. Yield: 84%.

1-2. Production of 2-[2-(4-cyanophenoxy)-1-phenylethylidene]-N-(4-trifluoromethoxyphenyl)hydrazinecarboxamide (compound Nos. 28 and 29)

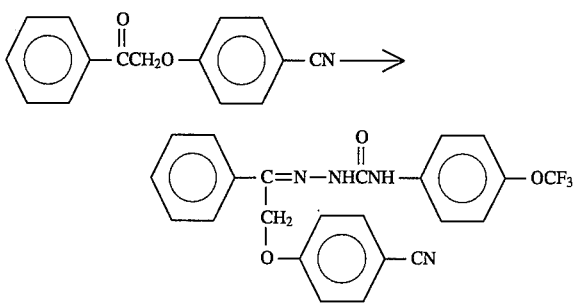

In 30 ml of methanol were dissolved 0.53 g (2.2 mmoles) of the α-(4-cyanophenoxy)acetophenone obtained in 1-1 and 0.53 g (2.2 mmoles) of N-(4-trifluoromethoxyphenyl)hydrazinecarboxamide, after which a drop of concentrated sulfuric acid was added to the resulting solution, and the reaction was carried out at room temperature for 8 hours.

After completion of the reaction, the solvent was removed by distillation under reduced pressure from the reaction solution. Water was added to the residue and the desired compound was extracted with ethyl acetate. The organic layer was washed with water, dried, and distilled to remove the solvent, whereby a crude product was isolated. The crude product obtained was purified and separated by a silica gel column chromatography (dichloromethane) to obtain two isomers of the desired compound, i.e., 0.46 g of Z-isomer and 0.40 g of E-isomer.

Z-isomer: Physical property m.p. 190° C. Yield 45%.
E-isomer: Physical property m.p. 179° C. Yield 39%.

Example 2

2-1. Production of γ-chloro-(3-trifluoromethyl)butyrophenone

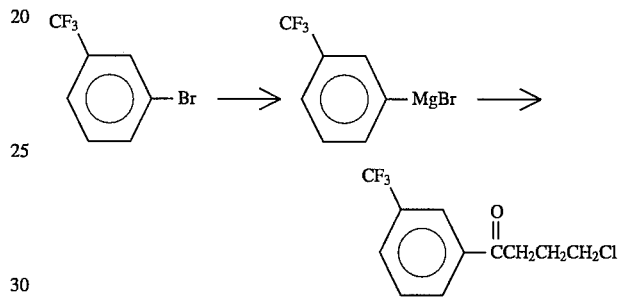

Under ice-cooling, 85 g (82 mmoles) of γ-chlorobutyronitrile was added dropwise to a solution in 100 ml of ether of a Grignard reagent prepared from 4.0 g (160 mmoles) of magnesium and 18.5 g (82 mmoles) of 3-bromobenzotrifluoride. After completion of the dropwise addition, the reaction was carried out with refluxing for 2 hours.

After completion of the reaction, the reaction solution was poured into ice water and neutralized with concentrated hydrochloric acid. The desired compound was extracted with ethyl acetate and the organic layer was washed with water, dried and then distilled under reduced pressure to remove the solvent, whereby 9.0 g of the desired compound was obtained.

Physical property: oil. Yield: 44%.

$^1$H-NMR [CDCl$_3$/TMS, δ values (ppm)] 2.23 (quintet, 2H), 3.20 (t, 2H), 3.67 (t, 2H), 7.5–8.26 (m, 4H).

2-2. Production of α-bromo-γ-chloro-(3-trifluoromethyl)butyrophenone

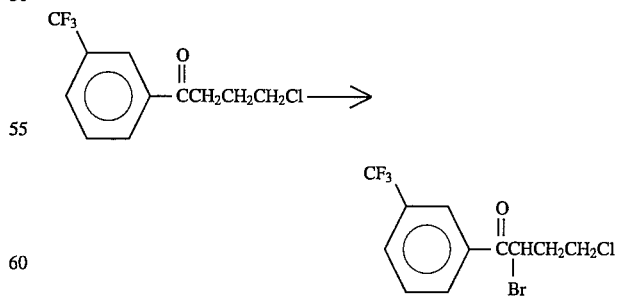

In 100 ml of acetic acid was dissolved 4.1 g (16 mmoles) of γ-chloro-(3-trifluoromethyl)butyrophenone, after which 2.9 g (18 mmoles) of bromine was added to the resulting solution, and the reaction was carried out at 50°–60° C. for 2 hours.

After completion of the reaction, the reaction mixture was poured into ice water and the desired compound was extracted with ethyl acetate. The organic layer was washed with an aqueous sodium thiosulfate solution and then an aqueous sodium hydrogencarbonate solution, dried over magnesium sulfate, and then distilled under reduced pressure to remove the solvent, whereby 4.8 g of the desired compound was obtained.

Physical property: oil. Yield: 89%. $^1$H-NMR [CDCl$_3$/TMS, δ values (ppm)] 2.55–2.64 (m; 2H), 3.74–3.90 (m, 2H), 5.40–5.50 (m, 1H), 7.60–8.35 (m, 4H).

2-3. Production of (3-trifluoromethylphenyl) (1-methylthiocyclopropyl)ketone

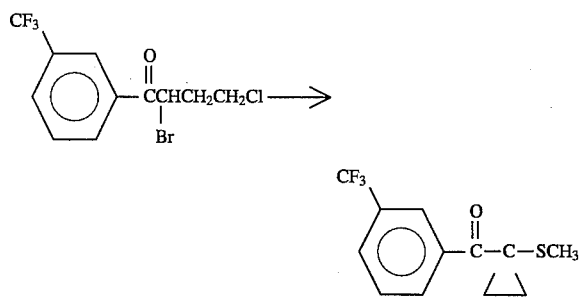

After 10 ml of a 50% aqueous sodium hydroxide solution and 2.8 g (6.1 mmoles) of a 15% aqueous methyl mercaptan sodium salt solution were mixed and then added to 30 ml of toluene, 10 mg of tetra-n-butylammonium bromide was added. Then, 1.0 g (3.0 mmoles) of α-bromo-γ-chloro-(3-trifluoromethyl)butyrophenone was added dropwise at room temperature, and the reaction was carried out for 2 hours.

After completion of the reaction, water was added to the reaction mixture and the desired compound was extracted with ethyl acetate. The organic layer was washed with water, dried, and then concentrated under reduced pressure. The resulting residue was purified by a silica gel column chromatography (ethyl acetate: n-hexane=1:10) to obtain 0.40 g of the desired compound.

Physical property: oil. Yield: 51%.
$^1$H-NMR [CDCl$_3$/TMS, δ values (ppm)] 1.28–1.60 (m, 4H), 2.06 (s, 3H), 7.55–8.35 (m, 4H).

2-4. Production of α-(1-methylthiocyclopropyl)-3-trifluoromethylbenzylidene-N-(4-trifluoromethoxyphenyl)hydrazinecarboxamide (compound No. 252)

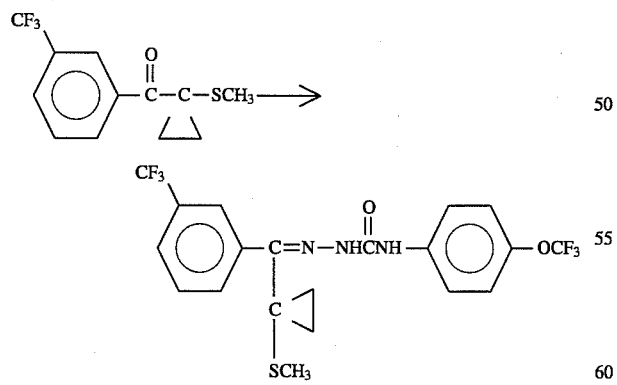

In 30 ml of methanol was dissolved 0.40 g (1.5 mmoles) of (3-trifluoromethylphenyl) (1-methylthiocyclopropyl)ketone, after which 0.43 g (1.9 mmoles) of N-(4-trifluoromethoxyphenyl)hydrazinecarboxamide and a drop of concentrated sulfuric acid were added to the resulting solution, and the reaction was carried out at 50°–60° C. for 8 hours.

After completion of the reaction, the solvent was removed by distillation under reduced pressure from the reaction mixture containing the desired compound. The resulting residue was purified by a silica gel column chromatography (ethyl acetate: n-hexane=1:4) to obtain 0.55 g of the desired compound as a mixture of E-form and Z-form.

Physical property: m.p. 142° C. Yield: 55%.

Example 3

3-1. Production of N,N-diethyl-4-fluorophenylglyoxamide

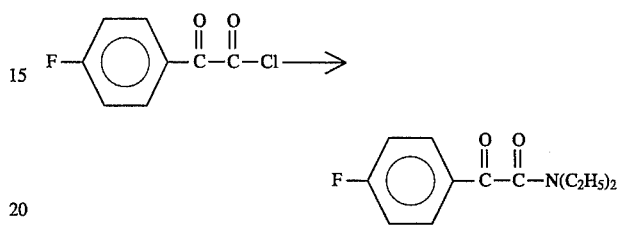

In 20 ml of tetrahydrofuran was dissolved 10 ml of diethylamine, after which a solution of 1.0 g (5.4 mmoles) of 4-fluorophenylglyoxylyl chloride in 3 ml of tetrahydrofuran was added dropwise at room temperature, and the reaction was carried out for 2 hours.

After completion of the reaction, the solvent was removed by distillation under reduced pressure from the reaction solution. Water was added to the residue and the desired compound was extracted with ethyl acetate. The organic layer was washed with diluted hydrochloric acid and an aqueous sodium hydrogencarbonate solution, dried over anhydrous magnesium sulfate, and distilled under reduced pressure to remove the solvent. The resulting residue was purified by a silica gel column chromatography (ethyl acetate: n-hexane=1:2) to obtain 0.62 g of the desired compound.

Physical property: paste. Yield: 52%.
$^1$H-NMR [CDCl$_3$/TMS, δ values (ppm)] 1.16 (t, 3H), 1.29 (t, 3H), 3.23 (q, 2H), 3.35 (q, 2H), 7.13–7.22 (m, 2H), 7.93–8.03 (m, 2H).

3-2. Production of 2-[α-(N,N-diethylcarbamoyl)-4-fluorobenzylidene]-N-(4-trifluoromethoxyphenyl)hydrazinecarboxamide (compound No. 165)

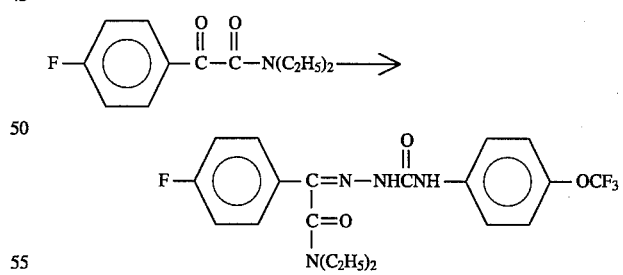

In 30 ml of methanol were dissolved 0.40 g (1.8 mmoles) of N,N-diethyl-4-fluorophenylglyoxamide and 0.42 g (1.8 mmoles) of N-(4-trifluoromethoxyphenyl)hydrazinecarboxamide, after which a drop of concentrated sulfuric acid was added to the resulting solution, and the reaction was carried out at 40°–50° C. for 16 hours.

After completion of the reaction, the solvent was removed by distillation under reduced pressure from the reaction solution. The resulting residue was purified by a silica gel column chromatography (ethyl acetate: n-hexane=2:3) to obtain 0.32 g of the desired compound.

Physical property: vitreous. Yield: 40%.

$^1$H-NMR [CDCl$_3$/TMS, δ values (ppm)] 1.02 (t, 3H), 1.30 (t, 3H), 3.18 (q, 2H), 3.61 (q, 2H), 7.10–7.72 (m, 8H), 8.19 (bs, 2H).

Example 4

4-1. Production of 1-(phenylglyoxylyl)piperazine

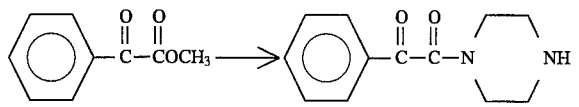

In 30 ml of methanol were dissolved 5.0 g (58 mmoles) of anhydrous piperazine and 0.80 g (4.9 mmoles) of methyl phenylglyoxylate, and the reaction was carried out at room temperature for 8 hours.

After completion of the reaction, the solvent was removed by distillation under reduced pressure from the reaction solution containing the desired compound. Water was added to the resulting residue and the desired compound was extracted with ethyl acetate (50 ml×3). The organic layer was washed with water, dried and then distilled under reduced pressure to remove the solvent, whereby 0.95 g of the desired compound was obtained.

Physical property: paste. Yield: 89%.

$^1$H-NMR [CDCl$_3$/TMS, δ values (ppm)] 1.78 (bs, 1H), 2.82 (t, 2H), 2.97 (t, 2H), 3.32 (t, 2H), 4.74 (t, 2H), 7.48–8.00 (m, 5H).

4-2. Production of 1-methoxycarbonyl-4-(phenylglyoxylyl)piperazine

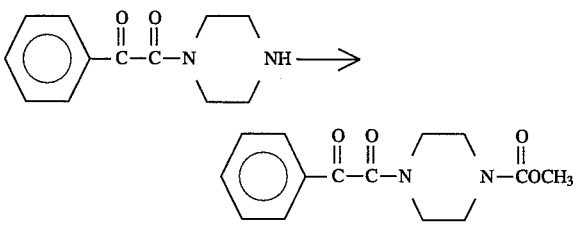

In 30 ml of tetrahydrofuran was dissolved 0.35 g (1.6 mmoles) of 1-(phenylglyoxylyl)piperazine, after which 0.5 ml of methyl chloroformate and 1 ml of triethylamine were added to the resulting solution, and the reaction was carried out at room temperature for 2 hours.

After completion of the reaction, the solvent was removed by distillation under reduced pressure from the reaction solution. Water was added to the resulting residue and the desired compound was extracted with ethyl acetate. The organic layer was washed with diluted hydrochloric acid and an aqueous sodium hydrogencarbonate solution, dried over anhydrous magnesium sulfate, and then distilled under reduced pressure to remove the solvent, whereby 0.37 g of the desired compound was obtained.

Physical property: paste. Yield: 83%.

$^1$H-NMR [CDCl$_3$/TMS, δ values (ppm)] 3.30–3.85 (m, 8H), 3.72 (s, 3H), 7.48–8.00 (m, 5H).

4-3. Production of 2-[α-[(4-methoxycarbonylpiperazino)carbonyl]benzylidene]-N-[4-trifluoromethoxyphenyl)hydrazinecarboxamide (compound No. 22)

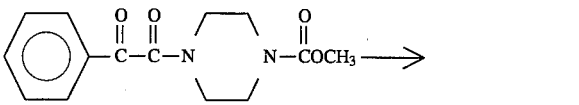

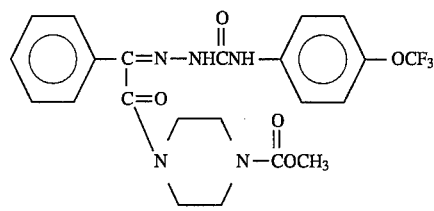

In 30 ml of methanol were dissolved 0.37 g (1.3 mmoles) of 1-methoxycarbonyl-4-(phenylglyoxylyl)piperazine and 0.32 g (1.3 mmoles) of N-(4-trifluoromethoxyphenyl)hydrazinecarboxamide, after which a drop of concentrated sulfuric acid was added to the resulting solution, and the reaction was carried out at 40°–50° C. for 24 hours.

After completion of the reaction, the solvent was removed by distillation under reduced pressure from the reaction solution. The resulting residue was purified by a silica gel column chromatography (ethyl acetate: n-hexane=1:1) to obtain 0.25 g of the desired compound.

Physical property: m.p. 186° C. Yield: 38%.

Example 5

5-1. Production of α-(N,N-diformylamino)-3-chloroacetophenone

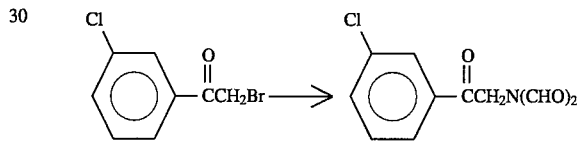

In 20 ml of acetonitrile was dissolved 20 g (86 mmoles) of α-bromo-3-chloroacetophenone, after which 8.14 g (86 mmoles) of sodium diformamide was added to the resulting solution, and the reaction was carried out at room temperature for 3 hours.

After completion of the reaction, the reaction mixture containing the desired compound was filtered under reduced pressure and the filtrate was concentrated. The desired compound was extracted with ethyl acetate, and the extracted solution was dried and then distilled under reduced pressure to remove the solvent, whereby 3.0 g of the desired compound was obtained.

Physical property: m.p. 71° C. Yield: 15%.

5-2. Production of α-amino-3-chloroacetophenone hydrochloride

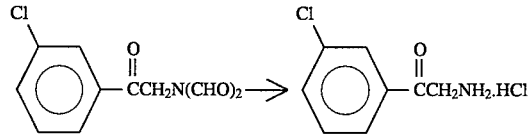

In 6N HCl aqueous solution was suspended in 12.7 g (56 mmoles) of α-(N,N-diformylamino)-3-chloroacetophenone, and the reaction was carried out with refluxing for 30 minutes.

After completion of the reaction, the reaction mixture was concentrated under reduced pressure, and the crystals precipitated were washed with a small volume of ether to obtain 11.2 g of the desired compound.

Physical property: m.p. 223° C. Yield: 97%.

5-3. Production of 3-chloro-α-benzoylaminoacetophenone

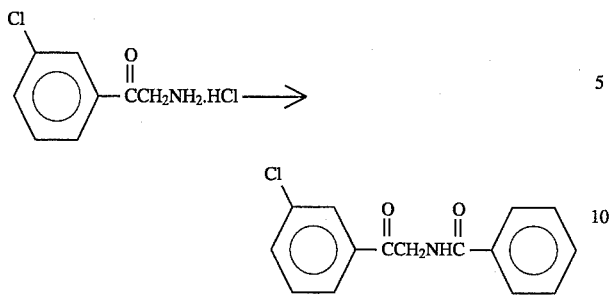

In 10 ml of tetrahydrofuran were dissolved 0.68 g (4.9 mmoles) of benzoyl chloride and 1.47 g (14.6 mmoles) of triethylamine, after which 1.0 g (4.9 mmoles) of α-amino-3-chloroacetophenone hydrochloride was added to the resulting solution, and the reaction was carried out at room temperature for 2 hours.

After completion of the reaction, the desired compound was extracted from the reaction mixture with ethyl acetate, and the extracted solution was washed with water, dried, and then distilled under reduced pressure to remove the solvent, whereby 0.60 g of the desired compound was obtained.

Physical property: m.p. 105° C. Yield: 43%.

5-4. Production of 2-[2-benzoylamino-1-(3-chlorophenyl)ethylidene]-N-(4-trifluoromethoxyphenyl)hydrazinecarboxamide (compound No. 124)

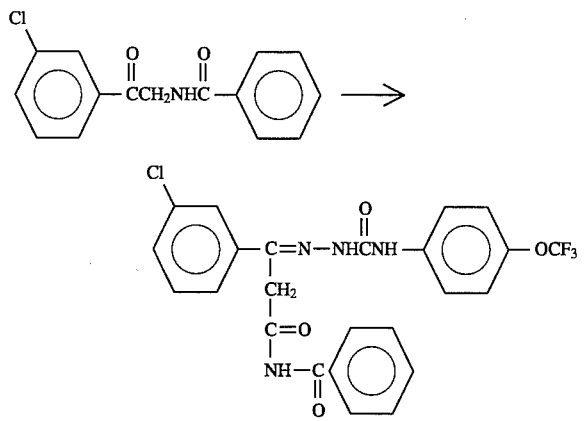

In 5 ml of ethanol was suspended 0.50 g (1.7 mmoles) of 3-chloro-α-benzoylaminoacetophenone, after which a drop of concentrated sulfuric acid was added to the resulting suspension, and the reaction was carried out at room temperature for 6 hours.

After completion of the reaction, the solvent was removed by distillation under reduced pressure from the reaction mixture. The desired compound was extracted from the resulting residue with ethyl acetate, and the extracted solution was washed with water, dried and then distilled under reduced pressure to remove the solvent, whereby 0.60 g of the desired compound was obtained.

Physical property: m.p. 190° C. Yield: 68%.

Example 6

6-1. Production of S-[2-oxo-(3-trifluoromethylphenyl)ethyl] acetate

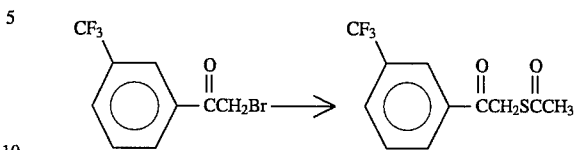

In 300 ml of ether was dissolved 4.3 g (56 mmoles) of thioacetic acid, followed by adding thereto 5.7 g (56 mmoles) of triethylamine. A solution of 15 g (56 mmoles) of α-bromo-3-trifluoromethylacetophenone in 50 ml of ether was added dropwise at room temperature over a period of 15 minutes. After completion of the dropwise addition, the reaction was carried out with refluxing for 1.5 hours.

After completion of the reaction, the insoluble materials were filtered off and the filtrate was concentrated under reduced pressure to obtain 15.4 g of the desired compound.

Physical property: crystals. Yield: 87%.

$^1$H-NMR [CDCl$_3$/TMS, δ values (ppm)] 2.43 (s, 3H), 4.40 (s, 2H), 7.64–8.26 (m, 4H).

6-2. Production of α-(2-propynylthio)-3-trifluoromethylacetophenone

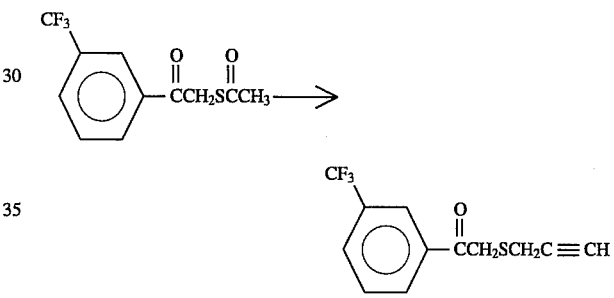

In 50 ml of methanol was dissolved 0.16 g (7.1 mmoles) of metallic sodium, and into the resulting solution was slowly dropped a solution of 1.0 g (5.2 mmoles) of S-[2-oxo-(3-trifluoromethylphenyl)ethyl]acetate in 10 ml of methanol. After completion of the dropping, the reaction was carried out for another 1.5 hours. Then, a solution of 0.71 g (6.0 mmoles) of 2-propynyl bromide in 15 ml of methanol was added to the reaction solution, and the resulting mixture was subjected to reaction for 1 hour.

After completion of the reaction, the reaction mixture was concentrated under reduced pressure and the desired compound was extracted with ethyl acetate. The extracted solution was washed with water, dried over anhydrous magnesium sulfate, and then distilled under reduced pressure to remove the solvent, whereby 0.95 g of the desired compound was obtained.

Physical property: oil. Yield: 97%.

6-3. Production of 2-[2-(2-propynylthio)-1-(3-trifluoromethylphenyl)ethylidene]-N-(4-trifluoromethoxyphenyl)hydrazinecarboxamide (compound No. 206)

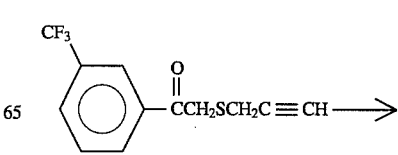

-continued

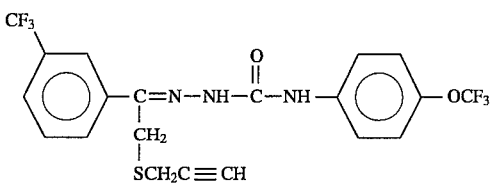

In 10 ml of ethanol was dissolved 0.95 g (5.0 mmoles) of α-(2-propynylthio)-3-trifluoromethylacetophenone, after which 1.23 g (5.25 mmoles) of N-(4-trifluoromethoxyphenyl)hydrazinecarboxamide and a drop of concentrated sulfuric acid were added to the resulting solution, and the reaction was carried out at room temperature for 6 hours.

After completion of the reaction, the reaction mixture was concentrated under reduced pressure and the desired compound was extracted with ethyl acetate. The extracted solution was washed with water, dried over anhydrous magnesium sulfate, and then distilled under reduced pressure to remove the solvent, whereby 1.1 g of the desired compound was obtained.

Physical property: m.p. 155° C. Yield: 54%.

Example 7

7-1. Production of 4-(3-trifluoromethylphenyl)-4-oxobutanamide

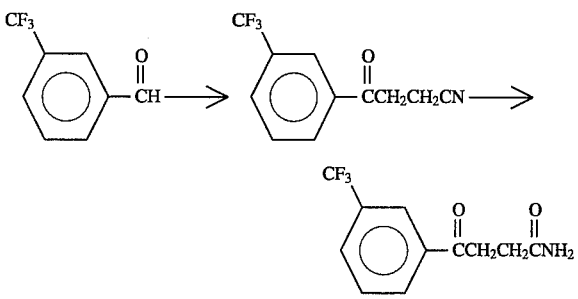

To a solution of 5.00 g (28.7 mmoles) of 3-trifluoromethylbenzaldehyde in 18 ml of dimethylformamide was added 0.28 g (5.7 mmoles) of powdered sodium cyanide, and the reaction was carried out at 45° C. for 30 minutes. Subsequently, a solution of 1.30 g (24.5 mmoles) of acrylonitrile in 2 ml of dimethylformamide was added dropwise to the reaction mixture over a period of 20 minutes. After completion of the dropwise addition, the resulting mixture was subjected to reaction for 4 hours. Then, 1 ml of acetic acid was added to the reaction mixture and the reaction was carried out for 10 minutes.

After completion of the reaction, the reaction mixture was concentrated under reduced pressure and the desired compound was extracted with ethyl acetate. The extracted solution was washed with water, dried over anhydrous magnesium sulfate, and then distilled under reduced pressure to remove the solvent. The resulting residue was purified by a silica gel column chromatography (n-hexane: ethyl acetate= 10:1) to obtain 5.63 g of 4-(3-trifluoromethylphenyl)-4-oxobutanenitrile.

Physical property: oil. Yield: 72.8%. $^1$H-NMR [CDCl$_3$/TMS, δ values (ppm)] 2.81 (t, 2H), 3.43 (t, 2H), 7.60–8.20 (m, 4H).

To 40 ml of concentrated sulfuric acid was added 5.50 (21.9 mmoles) of the obtained 4-(3-trifluoromethylphenyl)-4-oxobutanenitrile on an ice water bath, and the reaction was carried out at 0° C. for 30 minutes and then at room temperature for 5 hours.

After completion of the reaction, the reaction mixture was poured into 150 ml of ice water and the desired compound was extracted with chloroform. The extracted solution was washed with water, dried over anhydrous magnesium sulfate, and then distilled under reduced pressure to remove the solvent. The resulting residue was purified by a silica gel column chromatography (n-hexane: ethyl acetate=2:1) to obtain 2.70 g of the desired compound.

Physical property: m.p. 133° C. Yield: 45.6%.

7-2. Production of 2-[3-carbamoyl-1-(3-trifluoromethylphenyl)propylidene]-N-(4-trifluoromethoxyphenyl)hydrazinecarboxamide (compound No. 233)

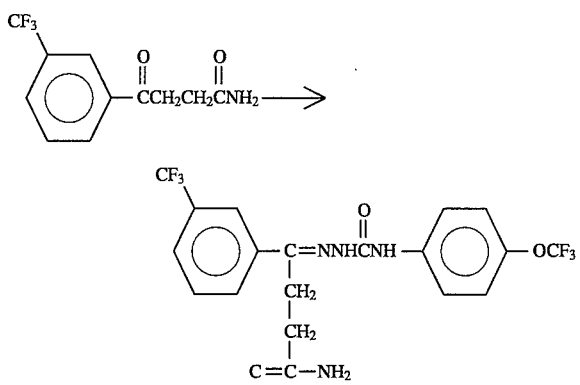

To a solution of 1.0 g (4.1 mmoles) of 4-(3-trifluoromethylphenyl)-4-oxobutanamide and 0.96 g (4.1 mmoles) of N-(4-trifluoromethoxyphenyl)hydrazinecarboxamide in 15 ml of tetrahydrofuran was added 15 ml of ethanol and then two drops of concentrated sulfuric acid, and the reaction was carried out at room temperature for 15 hours.

After completion of the reaction, the reaction solution was concentrated under reduced pressure and the desired compound was extracted with ethyl acetate. The extracted solution was washed with water, dried over anhydrous magnesium sulfate, and then distilled under reduced pressure to remove the solvent. The resulting residue was purified by a silica gel column chromatography (ethyl acetate) to obtain 1.14 g of the desired compound.

Physical property: m.p. 203° C. Yield: 60.4%.

Example 8

8-1. Production of 4-(3-trifluoromethylphenyl)-4-oxobutanoic acid

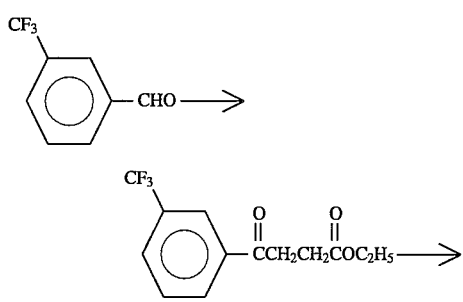

-continued

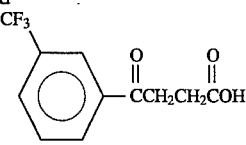

In 180 ml of dimethylformamide was dissolved 24.8 g (0.143 mole) of 4-trifluoromethylbenzaldehyde, after which 1.05 g (0.021 mole) of powdered sodium cyanide was added to the resulting solution, and the reaction was carried out at 45° C. for 30 minutes. Subsequently, a solution of 11.4 g (0.114 mole) of ethyl acrylate in 20 ml of dimethylformamide was added dropwise to the reaction mixture over a period of 20 minutes, and the resulting mixture was subjected to reaction for 4 hours. Then, 3 ml of acetic acid was added to the reaction mixture and the reaction was carried out for 30 minutes.

After completion of the reaction, the reaction mixture was poured into 300 ml of ice water and the desired compound was extracted with ethyl acetate. The extracted solution was washed with water, dried over anhydrous magnesium sulfate, and then distilled under reduced pressure to remove the solvent, whereby a crude product was obtained. The obtained crude product was purified by a silica gel column chromatography (n-hexane: ethyl acetate= 3:1) to obtain 24.6 g of ethyl 4-(3-trifluoromethylphenyl)-4-oxobutanoate.

Physical property: crystals. Yield: 63.0%.

In 200 ml of methanol was dissolved 20.0 g (73 mmoles) of the obtained ethyl 4-(3-trifluoromethylphenyl)-4-oxobutanoate, after which a solution of 8.2 g (0.20 mole) of lithium hydroxide monohydrate in 100 ml of water was added to the resulting solution, and the reaction was carried out for 10 hours.

After completion of the reaction, the reaction solution was concentrated under reduced pressure and adjusted to pH 2 with 6N hydrochloric acid. The crystals precipitated were collected by filtration and dried under reduced pressure to obtain 18.0 g of the desired compound.

Physical property: m.p. 88° C. Yield: 100%.

8-2. Production of N,N-diethyl-4-(3-trifluoromethylphenyl)-4-oxobutanamide

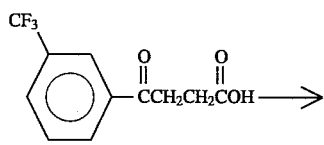

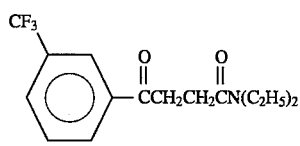

A mixture of 1.0 g (4.1 mmoles) of 4-(3-trifluoromethylphenyl)-4-oxobutanoic acid, 1.20 g (4.7 mmoles) of 2-chloro-1-methylpyridinium iodide and 0.36 g (4.9 mmoles) of diethylamine was dissolved in 20 ml of dichloromethane, followed by adding thereto 0.84 g (8.3 mmoles) of triethylamine, and the reaction was carried out with refluxing for 8 hours.

After completion of the reaction, the reaction mixture was poured into ice water and acidified with 2N hydrochloric acid. Then, the desired compound was extracted with methylene chloride, and the extracted solution was washed with water, dried over anhydrous magnesium sulfate, and then distilled under reduced pressure to remove the solvent, whereby a crude product was obtained.

The obtained crude product was purified by a silica gel column chromatography (n-hexane: ethyl acetate=1:1) to obtain 1.15 g of the desired compound.

Physical property: nD 1.5012 (21.6° C.).

Yield: 94%.

8-3. Production of 2-[3-(N,N-diethylcarbamoyl)-1-(3-trifluoromethylphenyl)propylidene]-N-(4-trifluoromethoxyphenyl)hydrazinecarboxamide (compound No. 235)

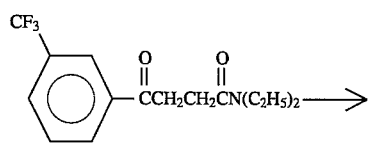

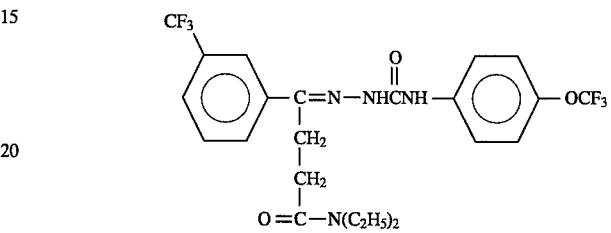

To 15 ml of tetrahydrofuran were added 0.67 g (2.2 mmoles) of N,N-diethyl-4-(3-trifluoromethyl)-4-oxobutanamide and 0.52 g (2.2 mmoles) of N-(4-trifluoromethoxyphenyl)hydrazinecarboxamide, and then 15 ml of ethanol and two drops of concentrated sulfuric acid, after which the reaction was carried out for 15 hours.

After completion of the reaction, the reaction mixture was concentrated under reduced pressure and the desired compound was extracted with ethyl acetate. The extracted solution was washed with water, dried over anhydrous magnesium sulfate, and then distilled under reduced pressure to remove the solvent, whereby a crude product was obtained.

The obtained crude product was purified by a silica gel column chromatography (n-hexane: ethyl acetate=2:1) to obtain 0.74 g of the desired compound.

Physical property: m.p. 148° C. Yield: 64%.

Example 9

9-1. Production of 4-oxo-4-phenyl-N-(4-trifluoromethoxyphenyl)-2-butenamide

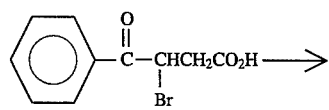

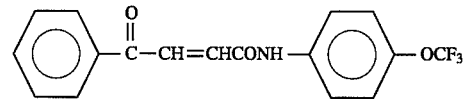

In 300 ml of tetrahydrofuran (THF) was dissolved 4.0 g (16 mmoles) of 3-bromo-4-oxo-4-phenylbutanoic acid, after which 2.0 g (19 mmoles) of ethyl chloroformate was added to the resulting solution, and then a solution of 4.7 g (47 mmoles) of triethylamine in 2 ml of THF was dropped thereinto slowly. Thereafter, the reaction was carried out at room temperature for 30 minutes. Subsequently, 3.3 g (19 mmoles) of 4-trifluoromethoxyaniline was added to the reaction mixture and the resulting mixture was subjected to reaction for 4 hours.

After completion of the reaction, water was added to the reaction mixture and the desired compound was extracted with ethyl acetate. The extracted solution was washed with water, dried over anhydrous magnesium sulfate, and then freed of the solvent under reduced pressure to obtain 2.8 g of the desired compound as crystals.

Physical property: m.p. 188° C. Yield: 60%.

9-2. Production of 2-[1-phenyl-3-[N'-(4-trifluoromethoxyphenyl)carbamoyl]-2-propenylidene]-N-(4-trifluoromethoxyphenyl)hydrazinecarboxamide (compound No. 294)

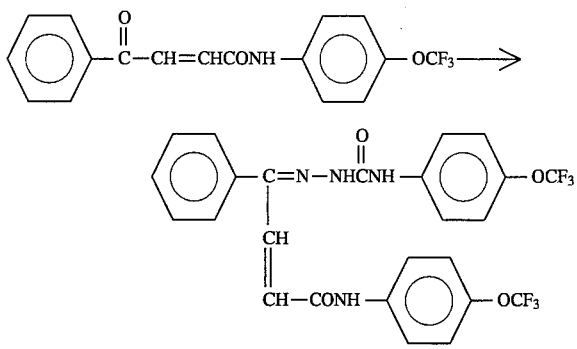

In 30 ml of methanol was dissolved 0.40 g (1.2 mmoles) of 4-oxo-4-phenyl-N-(4-trifluoromethoxyphenyl)-2-butenamide, after which a drop of concentrated sulfuric acid and 0.36 g (1.8 mmoles) of N-(4-trifluoromethoxyphenyl)-2-butenamide were added to the resulting solution, and the reaction was carried out with refluxing for 6 hours.

After completion of the reaction, the solvent was distilled off under reduced pressure and the desired compound was extracted from the residue with ethyl acetate. The extracted solution was washed with water, dried over anhydrous magnesium sulfate, and then freed of the solvent under reduced pressure to obtain 0.30 g of the desired compound as crystals.

Physical property: m.p. 237° C. Yield: 73%.

Example 10

10-1. Production of (2-propynyloxyimino)acetophenone

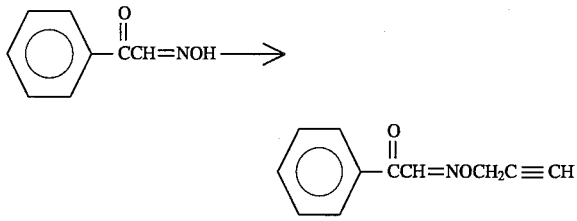

In 20 ml of acetonitrile were dissolved 3.0 g (19 mmoles) of isonitrosoacetophenone and 2.3 g (19 mmoles) of 2-propargyl bromide, after which 3.9 g (28 mmoles) of potassium carbonate was added to the resulting solution, and the reaction was carried out at room temperature for 3 hours.

After completion of the reaction, the reaction mixture was poured into water and the desired compound was extracted with ethyl acetate. The extracted solution was washed with water, dried over anhydrous magnesium sulfate, and then freed of the solvent under reduced pressure to obtain 2.5 g of the desired compound as paste.

Physical property: paste. Yield: 83%.

10-2. Production of 2-[1-phenyl-2-(2-propynyloxyimino)ethylene]-N-(4-trifluoromethoxyphenyl)hydrazinecarboxamide (compound Nos. 273 and 274)

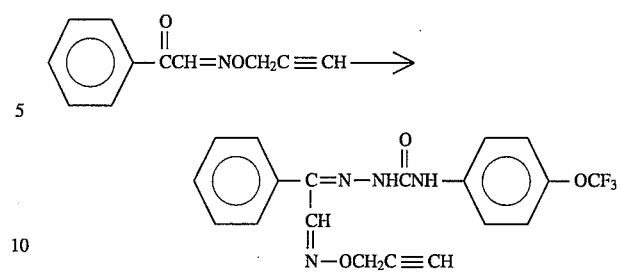

In 10 ml of ethanol were dissolved 0.50 g (2.5 mmoles) of (2-propynyloxyimino)acetophenone and 0.60 g (2.5 mmoles) of N-(4-trifluoromethoxyphenyl)hydrazinecarboxamide, after which a drop of concentrated sulfuric acid was added to the resulting solution, and the reaction was carried out at room temperature for 5 hours.

After completion of the reaction, the reaction solution was poured into water and the desired compound was extracted with ethyl acetate. The extracted solution was washed with water, dried over anhydrous magnesium sulfate, and freed of the solvent under reduced pressure. The residue was purified by a silica gel column chromatography (ethyl acetate: n-hexane=1:2) to obtain two forms of the desired compound, i.e., E-form and Z-form.

Physical property E-form: m.p. 169° C. Amount (yield) 0.23 g (22%). Z-form: m.p. 115° C. Amount (yield) 0.37 g (38%).

Example 11

11-1. Production of ethyl 2-(2-phenyl-2-oxoethylene)hydrazinecarboxylate

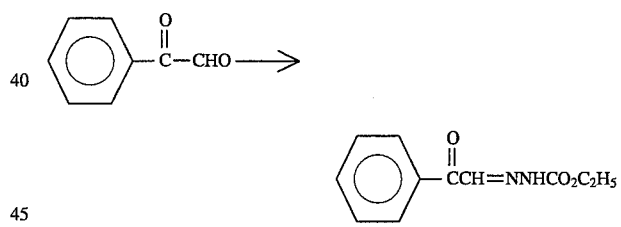

In ethanol were dissolved 1.0 g (7.5 mmoles) of phenylglyoxal and 1.6 g (15 mmoles) of ethyl carbamate, and the resulting solution was subjected to reaction at room temperature for 4 hours.

After completion of the reaction, the reaction solution was poured into water and the desired compound was extracted with ethyl acetate. The extracted solution was washed with water, dried over anhydrous magnesium sulfate, and then freed of the solvent under reduced pressure to obtain 0.40 g of the desired compound.

Physical property: m.p. 139° C. Yield: 27%.

11-2. Production of ethyl 2-[2-phenyl-2-[[N-(4-trifluoromethoxyphenyl)carbamoyl]hydrazono]ethylene]hydrazinecarboxylate (compound No. 272)

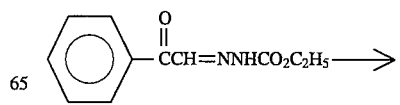

-continued

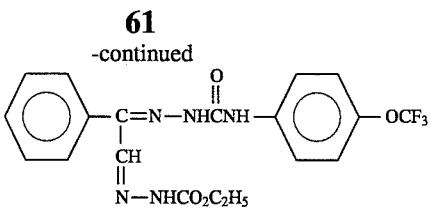

In 10 ml of ethanol were dissolved 0.30 g (1.4 mmoles) of ethyl 2-(2-phenyl-2-oxoethylene)hydrazinecarboxylate and 0.38 g (1.6 mmoles) of N-(4-trifluoromethoxyphenyl)hydrazinecarboxamide, after which a drop of concentrated sulfuric acid was added to the resulting solution, and the reaction was carried out at room temperature for 5 hours.

After completion of the reaction, the reaction solution was poured into water and the desired compound was extracted with ethyl acetate. The extracted solution was washed with water, dried over anhydrous magnesium sulfate, and then freed of the solvent under reduced pressure to obtain 0.26 g of the desired compound.

Physical property: m.p. 100° C. Yield: 42%.

Example 12

Production of 2-[2-(O,O-dimethoxyphosphoryl)-1-phenylethylidene]-N-(4-trifluoromethoxyphenyl)hydrazinecarboxamide (compound No. 288)

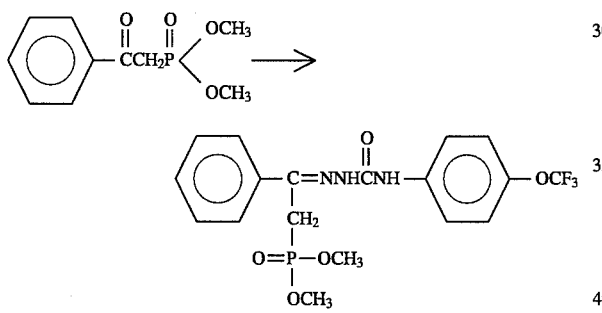

In 20 ml of methanol were dissolved 0.20 g (0.88 mmole) of dimethyl 2-oxo-2-phenylethanephosphonate and 0.21 g (0.88 mmole) of N-(4-trifluoromethoxyphenyl)hydrazinecarboxamide, after which a drop of concentrated sulfuric acid was added to the resulting solution, and the reaction was carried out with heating under reflux for 3 hours.

After completion of the reaction, the reaction solution was allowed to cool and distilled under reduced pressure to remove the solvent, and the desired compound was extracted with ethyl acetate. The extracted solution was washed with water, dried over anhydrous magnesium sulfate, and then freed of the solvent under reduced pressure to obtain crude crystals. The crude crystals were washed with ether to obtain 0.16 g of the desired compound.

Physical property: m.p. 222° C. Yield: 41%.

Example 13

13-1. Production of 4-phenylglyoxylylmorpholine

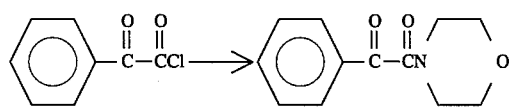

In 30 ml of tetrahydrofuran was dissolved 1.1 g (13 mmoles) of morpholine, after which a solution of 0.70 g (4.2 mmoles) of phenylglyoxylyl chloride in 5 ml of tetrahydrofuran was added dropwise to the resulting solution. After completion of the dropwise addition, the reaction was carried out at the same temperature for 2 hours.

After completion of the reaction, water was added to the reaction solution and the desired compound was extracted with ethyl acetate. The extracted solution was washed with diluted hydrochloric acid, dried over anhydrous magnesium sulfate, and then distilled under reduced pressure to remove the solvent, whereby 0.70 g of the desired compound was obtained as paste.

Physical property: paste. Yield: 77%.

$^1$H-NMR [CDCl$_3$/TMS, δ values (ppm)] 3.38 (t, 2H), 3.65 (t, 2H), 3.70 (s, 4H), 7.50–8.00 (m, 5H).

13-2. Production of 2-(α-morpholinocarbonylbenzylidene)-N-(4-trifluoromethoxyphenyl)hydrazinecarboxamide (compound No. 18)

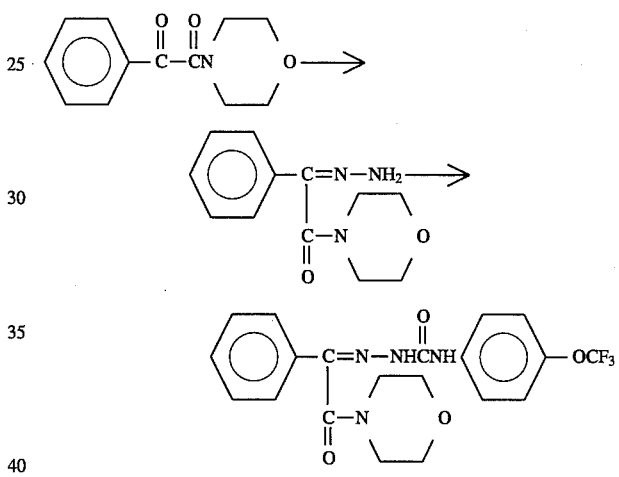

In 30 ml of methanol was dissolved 0.7 g (3.2 mmoles) of 4-phenylglyoxylylmorpholine, after which 10 ml of hydrazine hydrate and a drop of concentrated sulfuric acid were added to the resulting solution, and the reaction was carried out at 40°–50° C. for 4 hours.

After completion of the reaction, the reaction solution was concentrated under reduced pressure and the desired compound was extracted with ethyl acetate. The extracted solution was washed with water, dried over anhydrous magnesium sulfate, and then distilled under reduced pressure to remove the solvent, whereby a hydrazone was obtained as an intermediate.

The obtained hydrazone was dissolved in 30 ml of tetrahydrofuran, after which 5 ml of pyridine and 0.58 g (2.9 mmoles) of 4-trifluoromethoxyphenyl isocyanate were added to the resulting solution at room temperature, and the reaction was carried out for 8 hours.

After completion of the reaction, the reaction solution was concentrated under reduced pressure, followed by purification by a silica gel column chromatography (ethyl acetate: n-hexane=2:3), whereby 0.30 g of the desired compound was obtained.

Physical property: m.p. 155° C. Yield: 30%.

Example 14

14-1. Production of N,N-dimethyl-2-hydrazono-2-phenylethanesulfonamide

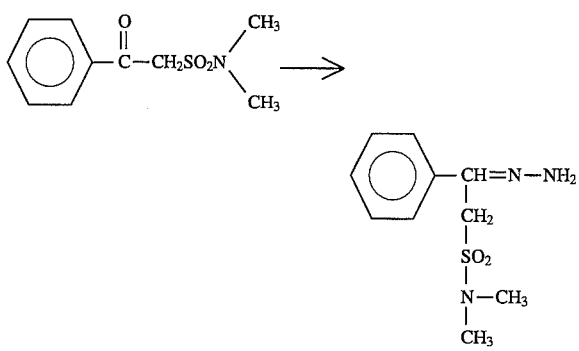

In 40 ml of ethanol were dissolved 1.0 g (4.4 mmoles) of N,N-dimethyl-2-oxo-2-phenylethanesulfonamide and 0.44 g (8.8 mmoles) of hydrazine hydrate, after which a drop of concentrated sulfuric acid was added to the resulting solution, and the reaction was carried out with heating under reflux for 2 hours.

After completion of the reaction, the reaction solution was allowed to cool and distilled under reduced pressure to remove the solvent, and the desired compound was extracted with ethyl acetate. The extracted solution was washed with water, dried over anhydrous magnesium sulfate, and then freed of the solvent under reduced pressure to obtain 0.73 g of the desired compound as crystals.

Physical property: crystals. Yield: 69%.

14-2. Production of 2-[2-N',N'-dimethylaminosulfonyl)-1-phenyl]ethylidene-N-(4-trifluoromethoxyphenyl)hydrazinecarboxamide (compound No. 290)

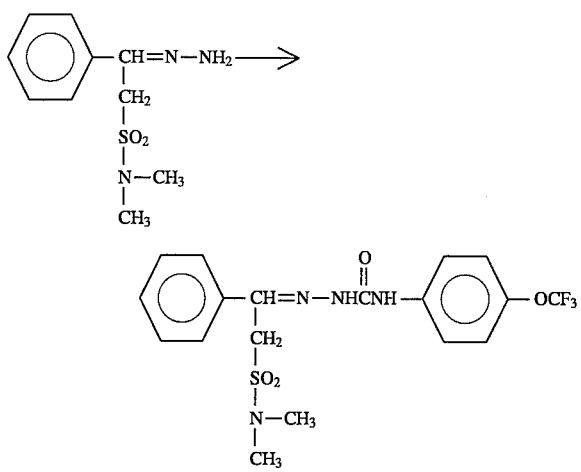

In a mixed solvent of 15 ml of tetrahydrofuran and 15 ml of pyridine was dissolved 0.50 g (2.1 mmoles) of N,N-dimethyl-2-hydrazono-2-phenylethanesulfonamide, followed by adding thereto 0.42 g (2.1 mmoles) of 4-trifluoromethoxyphenyl isocyanate, and the reaction was carried out at room temperature for 2 hours.

After completion of the reaction, the solvent was distilled off under reduced pressure and the crude crystals thus obtained were washed with toluene to obtain 0.60 g of the desired compound.

Physical property: m.p. 210° C. Yield: 65%.

Example 15

15-1. Production of 2-thiobenzoyl-N-(4-trifluoromethoxyphenyl)hydrazinecarboxamide

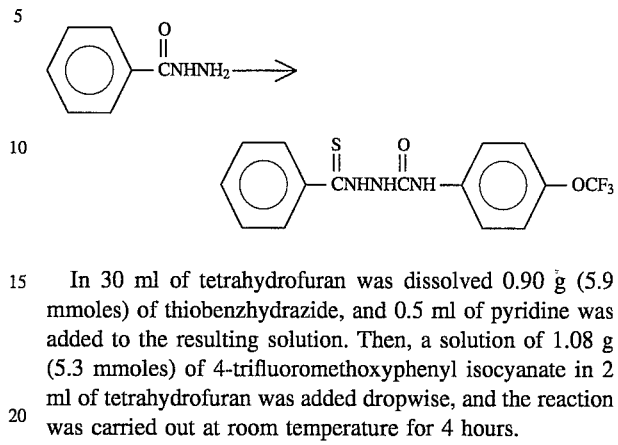

In 30 ml of tetrahydrofuran was dissolved 0.90 g (5.9 mmoles) of thiobenzhydrazide, and 0.5 ml of pyridine was added to the resulting solution. Then, a solution of 1.08 g (5.3 mmoles) of 4-trifluoromethoxyphenyl isocyanate in 2 ml of tetrahydrofuran was added dropwise, and the reaction was carried out at room temperature for 4 hours.

After completion of the reaction, the solvent was distilled off under reduced pressure to obtain 1.18 g of the desired compound.

Physical property: m.p. 191° C. Yield: 62%.

15-2. Production of 2-(α-isopropylthiobenzylidene)-N-(4-trifluoromethoxyphenyl)hydrazinecarboxamide (compound No. 278)

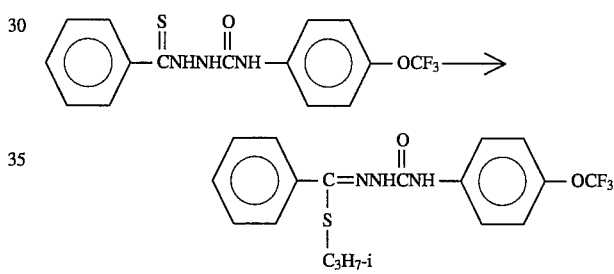

In 30 ml of acetone was suspended 1.5 g (4.2 mmoles) of 2-thiobenzoyl-N-(4-trifluoromethoxyphenyl)hydrazinecarboxamide, after which 0.72 g (4.2 mmoles) of isopropyl iodide and 1.5 g of anhydrous potassium carbonate were added to the resulting suspension, and the reaction was carried out at room temperature for 1 hour.

After completion of the reaction, the solvent was distilled off under reduced pressure and the desired compound was extracted with ethyl acetate. The extracted solution was washed with water, dried over anhydrous magnesium sulfate, and then freed of the solvent under reduced pressure to obtain 1.3 g of the desired compound as crystals.

Physical property: m.p. 122° C. Yield: 79%.

15-3. Production of 2-(α-isopropylsulfinylbenzylidene)N-(4-trifluoromethoxyphenyl)hydrazinecarboxamide (compound No. 279) and 2-(α-isopropylsulfonylbenzylidene)-N-(4-trifluoromethoxyphenyl)hydrazinecarboxamide (compound No. 280)

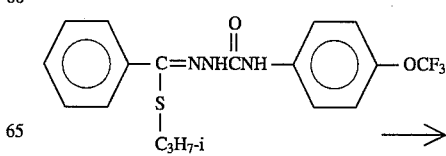

-continued

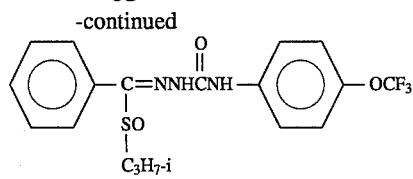

In 20 ml of methanol was dissolved 0.50 g (1.3 mmoles) of 2-(α-isopropylthiobenzylidene)-N-(4-trifluoromethoxyphenyl)hydrazinecarboxamide, after which a suspension of 2.0 g (3.3 mmoles) of sodium peroxymonosulfate in 10 ml of water was added to the resulting solution, and the reaction was carried out at room temperature for 30 minutes.

After completion of the reaction, the reaction mixture was poured into water and the desired compound was extracted with ethyl acetate. The extracted solution was washed with water, dried over anhydrous magnesium sulfate, and then freed of the solvent under reduced pressure. The product thus obtained was purified by a silica gel column chromatography (ethyl acetate: n-hexane=1:2) to obtain the desired compound.

Physical property Sulfoxide product: paste. Amount (yield) 0.23 g (44%). Sulfone product: m.p. 124° C. (decomp.). Amount (yield) 0.10 g (19%).

Example 16

Production of 2-[2-(4-cyanophenoxy)-1-phenylethyl]-N-(4-trifluoromethoxyphenyl)hydrazinecarboxamide (compound No. 342)

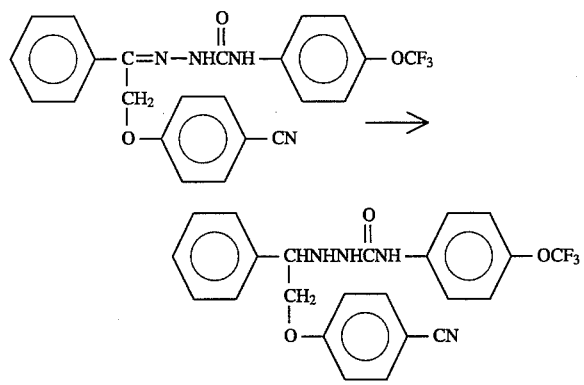

In a mixed solvent of 15 ml of methanol and 15 ml of tetrahydrofuran was dissolved 0.30 g (0.66 mmole) of 2-[2-(4-cyanophenoxy)-1-phenylethylidene]-N-(4-trifluoromethoxyphenyl)hydrazinecarboxamide, after which 0.20 g (3.2 mmoles) of sodium cyanoborohydride (NaBH₃CN) was added to the resulting solution. The resulting mixture was maintained at pH 4 to 6 with hydrogen chloride (a methanolic solution) with stirring. After confirming the completion of the reaction by a thinlayer chromatography, the solvent was distilled off under reduced pressure and water was added to the residue, followed by neutralization with sodium hydrogencarbonate. The desired compound was extracted with ethyl acetate, and the organic layer was washed with water, dried over anhydrous magnesium sulfate, and then distilled under reduced pressure to remove the solvent, whereby 0.32 g of the desired compound was obtained.

Physical property: m.p. 176° C. Yield: 76%.

Example 17

Production of 2-[2-benzoylamino-1-(4-chlorophenyl)ethyl]-N-(4-trifluoromethoxyphenyl)hydrazinecarboxamide (compound No. 372)

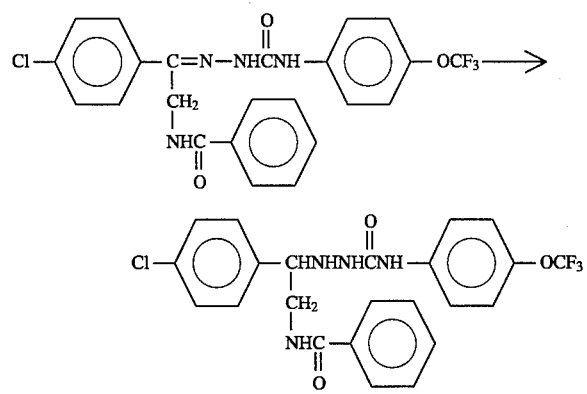

In 10 ml of methanol was suspended 0.30 g (0.59 mmole) of 2-[2-benzoylamino-1-(3-chlorophenyl)ethylidene]-N-(4-trifluoromethoxyphenyl)hydrazinecarboxamide, and 0.07 g (1 mmole) of sodium cyanoborohydride was added to the resulting suspension. The resulting mixture was adjusted to pH 4 to 6 with a methanolic solution of hydrogen chloride at room temperature and subjected to reaction.

After confirming the completion of the reaction by a thin-layer chromatography, the desired compound was extracted with ethyl acetate, and the organic layer was washed with an aqueous sodium hydrogencarbonate solution, dried over anhydrous magnesium sulfate, and then distilled under reduced pressure to remove the solvent, whereby 0.20 g of the desired compound was obtained.

Physical property: m.p. 230° C. Yield: 67%.

Example 18

Production of 2-[2-(2-propynylthio)-1-phenylethyl]-N-(4-trifluoromethoxyphenyl)hydrazinecarboxamide (compound No. 344)

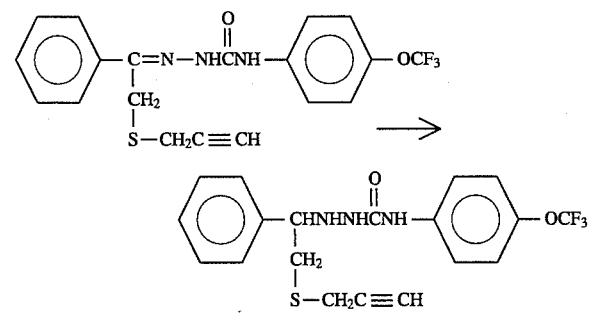

In 10 ml of methanol was suspended 0.50 g (1.2 mmoles) of 2-[2-(2-propynylthio)-1-phenylethylidene]-N-(4-trifluoromethoxyphenyl)hydrazinecarboxamide, and 0.37 g (4.7 mmoles) of sodium cyanoborohydride was added to the resulting suspension. The resulting mixture was adjusted to pH 4 to 6 with a methanolic solution of hydrogen chloride at room temperature and subjected to reaction.

After confirming the completion of the reaction by a thin-layer chromatography, the desired compound was extracted with ethyl acetate, and the organic layer was washed with an aqueous sodium hydrogencarbonate solution, dried over anhydrous magnesium sulfate, and then distilled under reduced pressure to remove the solvent, whereby 0.36 g of the desired compound was obtained.

Physical property: m.p. 157° C. Yield: 73%.

Example 19

Production of 2-[3-carbamoyl-1-(3-trifluoromethylphenyl)propyl]-N-(4-trifluoromethoxyphenyl)hydrazinecarboxamide (compound No. 390)

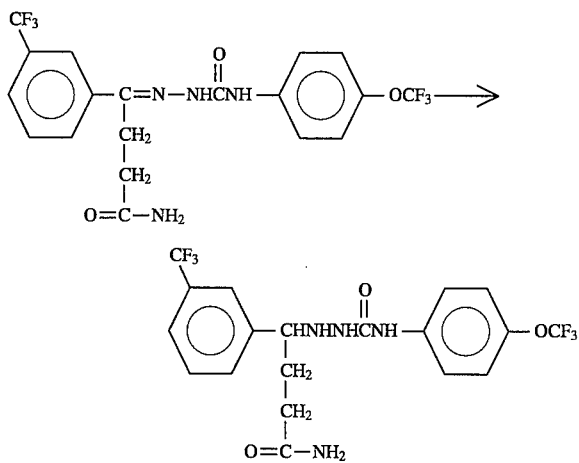

In a mixed solvent of 15 ml of tetrahydrofuran and 15 ml of methanol was dissoved 0.46 g (1.0 mmole) of 2-[3-carbamoyl-1-(3-trifluoromethylphenyl)propylidene]-N-(4-trifluoromethoxyphenyl)hydrazinecarboxamide, after which to the resulting solution were added 0.46 g (7.7 mmoles) of sodium cyanoborohydride and then 5 drops of a saturated methanolic solution of hydrochloric acid, and the reaction was carried out for 36 hours.

After completion of the reaction, the reaction mixture was concentrated under reduced pressure and the desired compound was extracted with ethyl acetate. The extracted solution was washed with water, dried and then distilled under reduced pressure to remove the solvent. The resulting residue was purified by a silica gel column chromatography (methanol: ethyl acetate) to obtain 0.35 g of the desired compound.

Physical property: m.p. 135° C. Yield: 76%.

Example 20

20-1. Production of 2-phenyl-2-(N-phenylcarbamoylmethyl)hydrazonoacetic acid

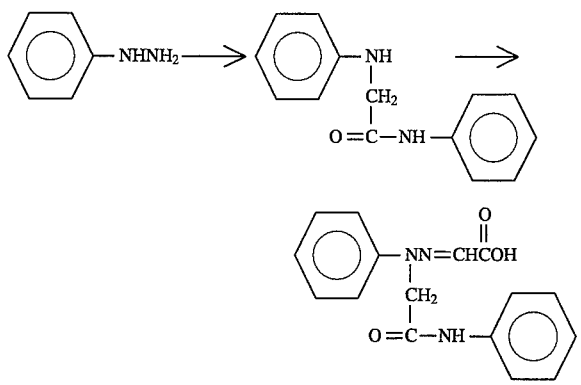

To 30 ml of toluene were added 3.00 g (27.8 mmoles) of phenylhydrazine, 4.71 g of chloroacetanilide and 2.81 g (27.8 mmoles) of triethylamine, and the reaction was carried out with heating under reflux for 13 hours.

After completion of the reaction, 50 ml of water was added to the reaction mixture and the desired compound was extracted with ethyl acetate (50 ml×2). The extracted solution was washed with water, dried over anhydrous magnesium sulfate, and then distilled under reduced pressure to remove the solvent, whereby 5.43 g of a crude product of 2-(1-phenylhydrazino)acetanilide was obtained.

In a mixed solvent of 50 ml of ethanol and 10 ml of dioxane was dissolved 2.50 g (10.4 mmoles) of the obtained 2-(1-phenylhydrazino)acetanilide, after which to the resulting solution was added 1.73 g (9.3 mmoles) of a 40% aqueous glyoxylic acid solution under ice-cooling, and the reaction was carried out at room temperature for 2 hours.

After completion of the reaction, the solvent was removed by distillation under reduced pressure from the reaction solution containing the desired compound, and the residue was washed with ether to obtain 1.13 g of the desired compound.

Physical property: m.p. 193°–194° C. Yield: 33%.

20-2. Production of 2-phenyl-2-(N-phenylcarbamoylmethyl)hydrazono-(4-trifluoromethoxy)acetanilide (compound No. 405)

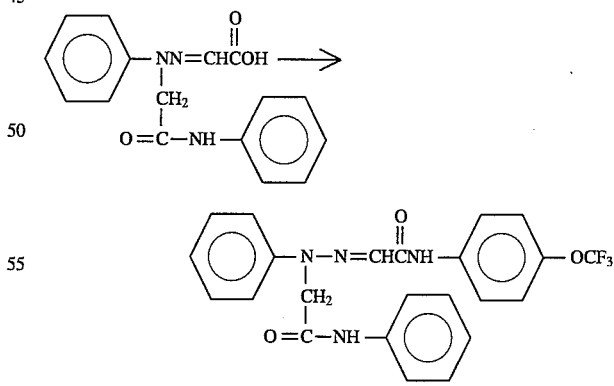

To 10 ml of dried carbon tetrachloride were added 0.40 g (1.4 mmoles) of 2-phenyl-2-(N-phenylcarbamoylmethyl)hydrazonoacetic acid and 0.32 g (2.7 mmoles) of thionyl chloride, and the reaction was carried out with heating under reflux for 1 hour.

After completion of the reaction, the reaction solution was allowed to cool and distilled under reduced pressure to remove the solvent and the excess thionyl chloride. The resulting concentrate was added dropwise to a solution of 0.26 g (2.5 mmoles) of triethylamine and 0.22 g (1.3 mmoles) of 4-trifluoromethoxyaniline in dried tetrahydrofuran, and the reaction was carried out at room temperature for 5 hours.

After completion of the reaction, 80 ml of water was added to the reaction solution and the desired compound was extracted with ethyl acetate (100 ml×2). The organic layer was washed with water, dried over anhydrous magnesium sulfate, and then distilled under reduced pressure to remove the solvent. The crystals thus obtained were washed with an ether-ethyl acetate mixed solution to obtain 0.35 g of the desired compound.

Physical property: m.p. 243°–245° C. Yield: 60%.

Example 21

21-1. Production of 2-(3-chlorophenyl)hydrazinoacetic acid

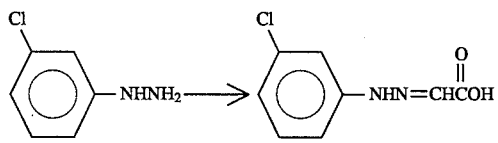

In 50 ml of ethanol was dissolved 15.0 g (0.11 mole) of 3-chlorophenylhydrazine, followed by adding dropwise thereto 19.5 g (0.11 mole) of a 40% aqueous glyoxylic acid solution and a solution of 4.2 g (0.11 mole) of sodium hydroxide in 20 ml of water under ice-cooling, and the reaction was carried out at room temperature for 2 hours.

After completion of the reaction, 80 ml of water was added to the reaction solution and the desired compound was extracted with ethyl acetate (100 ml×2). The organic layer was washed with water, dried over anhydrous magnesium sulfate, and then distilled under reduced pressure to remove the solvent. The crystals thus obtained were washed with an ether-ethyl acetate mixed solution to obtain 12.2 g of the desired compound.

Yield 58.4%.

$^1$H-NMR [CDCl$_3$/TMS, δ values (ppm)] 2.05 (bs, 1H), 6.98–7.01 (m, 2H), 7.08 (s, 1H), 7.18–7.25 (m, 2H), 8.50 (s, 1H).

21-2. Production of 2-(3-chlorophenyl)hydrazono-(4-trifluoromethoxy)acetanilide

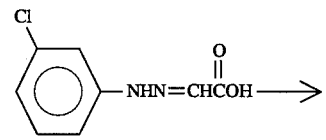

In 150 ml of dried dichloromethane was dissolved 8.9 g (50 mmoles) of 4-trifluoromethoxyaniline, and 12.9 g (50 mmoles) of 2-chloro-1-methylpyridinium iodide was added to the resulting solution. Then, a solution of 12.7 g (130 mmoles) of triethylamine and 10.0 g (50 mmoles) of 2-(3-chlorophenyl)hydrazonoacetic acid in 50 ml of dried tetrahydrofuran was added dropwise at room temperature. After completion of the dropwise addition, the reaction was carried out at room temperature for 10 hours.

After completion of the reaction, the solvent was removed by distillation under reduced pressure from the reaction solution, and 100 ml of water was added to the residue. The desired compound was extracted with ethyl acetate (200 ml×2), and the organic layer was washed with water, dried over anhydrous magnesium sulfate, and then distilled under reduced pressure to remove the solvent. The resulting residue was purified by a silica gel column chromatography (n-hexane: ethyl acetate=3:1) to obtain 5.64 g of the desired compound.

Physical property: m.p. 196°–197° C. Yield: 31.6%.

21-3. Production of 2-allyl-2-(3-chlorophenyl)hydrazono-(4-trifluoromethoxy)acetanilide (compound No. 414)

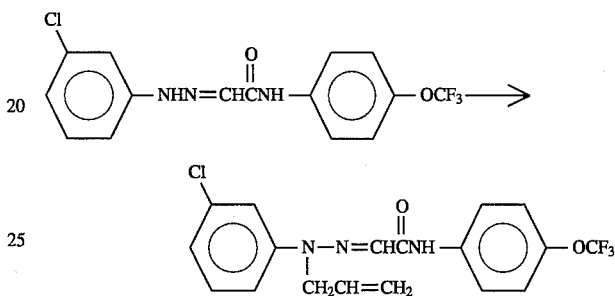

In 15 ml of dried dimethylformamide was dissolved 0.60 g (1.7 mmoles) of 2-(3-chlorophenyl)hydrazono-(4-trifluoromethoxy)acetanilide, and 0.08 g (2.0 mmoles) of 60% sodium hydride was added to the resulting solution under ice-cooling and stirred for 10 minutes. Then, 0.22 g (1.9 mmoles) of 3-propenylbromide was added dropwise and the reaction was carried out at room temperature for 1 hour.

After completion of the reaction, the reaction mixture was poured into ice water and the desired compound was extracted with ethyl acetate (50 ml×2). The organic layer was washed with water, dried over anhydrous magnesium sulfate, and then distilled under reduced pressure to remove the solvent. The resulting residue was purified by a silica gel column chromatography (n-hexane: ethyl acetate=3:1) to obtain 0.27 g of the desired compound.

Physical property: m.p. 79°–81° C. Yield: 40%.

Example 22

Production of 2-(3-chlorophenyl)-2-[N-(4-cyanophenylcarbamoylmethyl)]hydrazino-(4-trifluoromethoxy)acetanilide (compound No. 443)

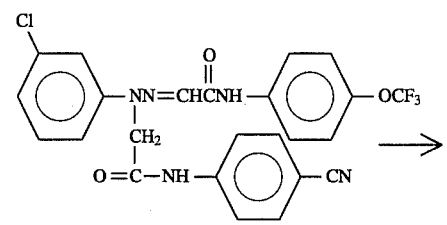

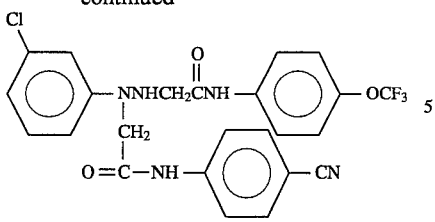

In a mixed solvent of 1 ml of dried tetrahydrofuran and 3 ml of methanol was dissolved 0.18 g (0.35 mmole) of 2-(3-chlorophenyl)-2-[N-(4-cyanophenylcarbamoylmethyl)]hydrazono-(4-trifluoromethoxy)acetanilide, followed by adding thereto 0.09 g (1 mmole) of sodium cyanotrihydroborate and 3 ml of a saturated methanolic solution of hydrochloric acid under ice-cooling, and the reaction was carried out at room temperature for 1 hour.

After completion of the reaction, the solvent was removed by distillation under reduced pressure from the reaction mixture, and 30 ml of a saturated aqueous sodium hydrogencarbonate solution was added to the residue. The desired compound was extracted with ethyl acetate (300 ml×2), and the organic layer was washed with water, dried over anhydrous magnesium sulfate, and then distilled under reduced pressure to remove the solvent. The resulting residue was purified by a silica gel column chromatography (n-hexane: ethyl acetate=1:1) to obtain 0.17 g of the desired compound.

Physical property: m.p. 183.2°–184.6° C. Yield: 94%.

Example 23

23-1. Production of S-Phenyl 3-chloro-N-methylbenzhydrazonethioate.

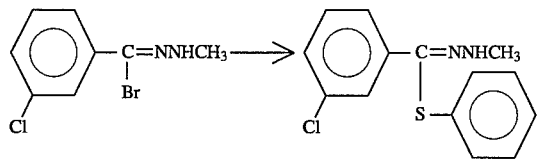

In 30 ml of dimethylformamide was dissolved 2.0 g (8.1 mmoles) of 3-chloro-N-methylbenzhydrazonoyl bromide, after which 1.1 g (9.7 mmoles) of thiophenol and 2.0 g (14 mmoles) of anhydrous potassium carbonate was added to the resulting solution, and the reaction was carried out at room temperature for 4 hours.

After completion of the reaction, the reaction mixture was poured into ice water and extracted with ether. The extracted solution was dried over anhydrous magnesium sulfate, and then distilled under reduced pressure to remove the solvent, whereby 1.7 g of the desired compound was obtained as oil.

Physical property: nD 1.6621 (29° C.). Yield: 99%.

23.2. Production of 2-(3-chloro-α-phenylthiobenzylidene)-N-(4-difluoromethoxyphenyl)-1-methylhydrazinecarboxamide. (Compound No. 309)

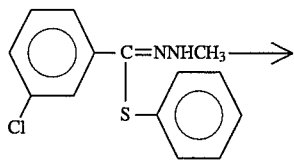

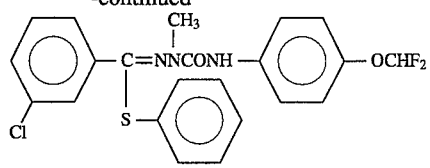

In 20 ml tetrahydrofran was dissolved 0.43 g (2.0 mmoles) of S-phenyl 3-chloro-N-methylbenzhydrazonethioate, after which 0.5 ml of pyridine was added to the resulting solution. Subsequently, a solution of 0.36 g (1.9 mmoles) of 4-difluoromethoxyphenyl isocyanate in 1 ml tetrahydrofran solution was added dropwise to the reaction mixture. The reaction was carried out at room temperature for 2 hours.

After completion of the reaction, the reaction mixture was distilled under reduced pressure to remove the solvent, whereby a crude product was obtained. The obtained crude product was purified by a silica-gel column chromatography (n-hexane: ethyl acetate=4:1) to obtain 0.32 g of desired compound as crystals.

Physical property: m.p. 96° C. Yield: 41%.

Agricultural and horticultural insecticides containing the hydrazine derivative of the general formula (I) of the present invention as an active ingredient are suitable for controlling various insect pests such as agricultural insect pests, forest insect pests, horticultural insect pests, stored grain insect pests, sanitary insect pests, nematodes, etc. They have an insecticidal effect also, for example, on LEPIDOPTERA including summer fruit tortrix (*Adoxophyes orana fasciata*), smaller tea tortrix (Adoxophes sp.), Manchurian fruit moth (*Grapholita inopinata*), oriental fruit moth (*Grapholita mlesta*), soybean pod border (*Leguminivora glycinivorella*), mulberry leafroller (*Olethreutes mori*), tea leafroller (*Caloptilla thevivora*), Caloptilia sp. (*Calopilia zachrysa*), apple leafminer (*Phyllonorycter rengoniella*), pear barkminer (*Spulerina astaurota*), common white (*Piers rapae crucivora*), tabacco budworm (*Heliothis armigera*), codling moth (*Laspeyresia pomonella*), diamondback moth (*Plutella xylostella*), apple fruit moth (*Argyresthia conjugella*), peach fruit moth (*Carposina niponensis*), rice stem borer (*Chilo suppressalia*), rice leafroller (*Cnaphalocrocis medinalis*), tabacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticeps*), brown rice planthopper (*Nilaparvata lugens*), whitebacked rice planthopper (*Sogatella furcifera*), citrus psylla (*Diaphorina citri*), grape whitefly (*Aleurolobus taonabae*), sweetpotato whitefly (*Bemisia tabaci*), greenhouse whitefly (*Trialeurodes vaporariorum*), turnip aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), San Jose scale (*Comstockaspis perniciosa*), arrowhead scale (*Unaspis yanonensis*), etc.; COLEOPTERA including soybean beetle (*Anomala rufocuprea*), Japanese beetle (*Popillia japonica*), tabacco beetle (*Lasioderma serricorne*), powderpost beetle (*Lyctus brunneus*), twenty-eight-spotted ladybird (*Epilachna vigintioctopunctata*), adzuki bean weevile (*Callosobruchus chinensis*), vegetable weevil (*Listroderes costirostris*), maize weevil (*Sitophilus zeamais*), boll weevil (*Anthonomus grandis grandis*), rice water weevil (*Lissorhoptrus oryzophilus*), cucurbit leaf beetle (*Aulacophora femoralis*), rice leaf beetle (*Outlema oryzae*), striped flea beetle (*Phyllotreta striolata*), pine shoot beetle (*Tomicus piniperda*), Colorado potato beetle (*Leptinotarsa decemilineata*), Mexican bean beetle (*Epilachna varivestis*), corn rootworm (Diabrotica sp.), etc.; DIPTERA including melon fly (*Dacus*(Zeugodacus) *cucurbitae*), oriental fruit fly (*Dacus*(Bactrocera) *dorsalis*), rice leafminer (*Agnomyza oryzae*), onion maggot (*Delia antiqua*), seedcorn maggot (*Delia platura*), soybeanpod gall midge (Asphodylia sp.), muscid fly (*Musca domestica*), house mosquito (*Culex pipiens*), etc.; and TYLENCHIDA including root-lesion nematode (Pratylenchus sp.), coffer root-lesion nematode (*Pratylenchus coffeae*), potato cyst nematode (*Globodera rostochiensis*), root-knot nematode (meloidogyne sp.), citrus nematode (*Tylenchulus semipenetrans*), Aphelenchus sp. (*Aphelenchus avenae*), chrysanthemum foliar (*Aphelenchoides ritzemabosi*), etc. The insecticides are markedly effective particularly against insect pest belonging to LEPIDOPTERA, COLEOPTERA and the like.

The zoological names and the like are in accordance with Applied Zoology and Entomology Society of Japan, "List of Agricultural and Forest Injurious Animals and Insects", published in 1987.

The agricultural and horticultural insecticide containing the hydrazine derivative of the general formula (I) of the present invention as an active ingredient has a marked insecticidal effect on the above-exemplified insect pests, sanitary insect pests, and/or nematodes, which are inurious to paddy rice, fruit trees, vegetables and other crops, and flowers and ornament plants. Therefore, the desired effect of the insecticide of the present invention can be obtained by applying the insecticide to the paddy field water, stalks and leaves of fruit trees, vegetables, other crops, flowers and ornament plants, soil, etc., or to the inside of a house or ditches around a house, in which the above-exemplified sanitary insect pests injurious to men and beasts appear or are expected to appear. The application is carried out at a season at which the insect pests, sanitary pests or nematodes are expected to appear, before their appearance or at the time when their appearance is confirmed. The present invention however should not be limited to these embodiments.

When the hydrazine derivative of the general formula (I) of the present invention is used as an agricultural and horticultural insecticide, it is generally prepared into conveniently usable forms according to an ordinary manner for preparation of agrochemicals.

That is, the hydrazine derivative of the general formula (I) of the present invention and, optionally, an adjuvant are blended with a suitable inert carrier in a proper proportion and prepared into a suitable preparation form such as a suspension, emulsifiable concentrate, soluble concentrate, wettable powder, granules, dust or tablet through dissolution, dispersion, suspension, mixing, impregnation, adsorption or sticking.

The inert carrier in this invention may be either solid or liquid. As the solid carrier, there can be exemplified soybean flour, cereal flour, wood flour, bark flour, saw dust, powdered tobacco stalks, powdered walnut shells, bran, powdered cellulose, extraction residues of vegetables, powdered synthetic polymers or resins, clays (e.g. kaolin, bentonite, and acid clay), talcs (e.g. talc and pyrophyllite), silica powders or flakes [e.g. diatomaceous earth, silica sand, mica and white carbon, i.e. synthetic, high-dispersion silicic acid, also called finely divided hydrated silica or hydrated silicic acid, some of commercially available products contain calcium silicate as the major component)], activated carbon, powdered sulfur, powdered pumice, calcined diatomaceous earth, ground brick, fly ash, sand, calcium carbonate powder, calcium phosphate powder and other inorganic or mineral powders, chemical fertilizers (e.g. ammonium sulfate, ammonium phosphate, ammonium nitrate, urea and ammonium chloride), and compost. These carriers may be used alone or as a mixture thereof.

The liquid carrier is that which itself has solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, Cellosolve, dipropyl ether and tetrahydrofuran; aliphatic hydrocarbons such as kerosene and mineral oils; aromatic hydrocarbons such as benzene, toluene, xylene, solvent naphtha and alkylnaphthalene; halogenated hydrocarbons such as dichloroethane, chloroform and carbon tetrachloride; esters such as ethyl acetate, diisopropyl phthalate, dibutyl phthalate and dioctyl phthalate; amides such as dimethylformamide, diethylformamide and dimethylacetamide; nitriles such as acetonitrile; and dimethyl sulfoxide.

The following are typical examples of the adjuvant, which are used depending upon purposes and used alone or in combination in some cases, or need not to be used at all.

To emulsify, disperse, dissolve and/or wet an active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and lignin sulfonates.

To improve the flowability of a solid product, there may be used adjuvants such as waxes, stearates and alkyl phosphates.

Adjuvants such as naphthalenesulfonic acid condensation products and polycondensates of phosphates may be used as a peptizer for dispersible products.

Adjuvants, e.g. silicon oils may also be used as a defoaming agent.

The content of the active ingredient may be varied as required. In dusts or granules, the suitable content thereof is from 0.01 to 50% by weight. In emulsifiable concentrates or flowable wettable powders, it is also from 0.01 to 50% by weight.

An agricultural and horticultural insecticide containing the hydrazine derivative of the general formula (I) of the present invention as an active ingredient is used to control a variety of insect pests in the following manner. That is, it is applied to the insect pests or a site where appearance or growth of the insect pests is undesirable, as it is or after being properly diluted with or suspended in water or the like, in an amount effective for control of the insect pests.

The applying dosage of the agricultural and horticultural insecticide containing the hydrazine derivative of the general formula (I) of the present invention as an active ingredient is varied depending upon various factors such as a purpose, insect pests to be controlled, a growth state of a plant, tendency of insect pests appearance, weather, environmental conditions, a preparation form, an application method, an application site and an application time. It may be properly chosen in the range of 0.01 g to 5 kg (in terms of the active ingredient) per 10 ares depending upon purposes.

The agricultural and horticultural insecticide containing the hydrazine derivative of the general formula (I) of the present invention as an active ingredient may be used in admixture with other insecticides or fungicides in order to expand both spectrum of controllable insect pest species and the period of time when effective applications are possible or to reduce the dosage.

Typical preparation examples and test examples of the present invention are described below but they should not be construed as limiting the scope of the invention.

In the preparation examples, parts are all by weight.

Formulation Example 1

| | |
|---|---|
| Each compound of the invention | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| | |
|---|---|
| Each compound of the invention | 3 parts |
| Clay powder | 82 parts |
| Diatomaceous earth powder | 15 parts |

A dust was prepared by mixing uniformly and grinding the above ingredients.

Formulation Example 3

| | |
|---|---|
| Each compound of the invention | 5 parts |
| Mixed powder of bentonite and clay | 90 parts |
| Calcium lignin sulfonate | 5 parts |

Granules were prepared by mixing the above ingredients uniformly, and kneading the resulting mixture together with a suitable amount of water, followed by granulation and drying.

Formulation Example 4

| | |
|---|---|
| Each compound of the invention | 20 parts |
| Mixture of kaolin and synthetic, high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Insecticidal effect on common cutworm (*Spodoptera litura*)

A piece of cabbage leaf (cultivar; Shikidori) was immersed for about 30 seconds in a liquid chemical prepared by diluting a preparation containing each compound of the present invention as an active ingredient to adjust the concentration to 500 ppm.

After air-drying, it was placed in a plastic Petri dish with a diameter of 9 cm and inoculated with second-instar larvae of common cutworm, after which the dish was closed and then allowed to stand in a room thermostated at 25%.

Eight days after the inoculation, the dead and alive were counted. The mortality was calculated according to the following equation and the insecticidal effect was judged according to the criterion shown below.

The test was carried out with triplicate groups of 10 insects.

$$\text{Corrected mortality (\%)} = \left( \frac{\text{Number of dead larvae}}{\text{Number of inoculated larvae}} \right) \times 100$$

Criterion:

| Effect | Mortality (%) |
|---|---|
| A | 100 |
| B | 99–90 |
| C | 89–80 |
| D | 79–50 |

The results obtained are shown in Table 9.

TABLE 9

| Compound No. | Concentration (ppm) | Judgement |
|---|---|---|
| 2 | 500 | A |
| 3 | 500 | A |
| 4 | 500 | D |
| 5 | 500 | A |
| 6 | 500 | C |
| 7 | 500 | B |
| 8 | 500 | D |
| 10 | 500 | A |
| 11 | 500 | A |
| 12 | 500 | A |
| 13 | 500 | A |
| 14 | 500 | A |
| 15 | 500 | A |
| 16 | 500 | A |
| 17 | 500 | A |
| 18 | 500 | A |
| 19 | 500 | A |
| 20 | 500 | A |
| 26 | 500 | D |
| 31 | 500 | A |
| 32 | 500 | A |
| 33 | 500 | A |
| 34 | 500 | A |
| 35 | 500 | C |
| 39 | 500 | D |
| 41 | 500 | B |
| 45 | 500 | A |
| 46 | 500 | A |
| 47 | 500 | A |
| 48 | 500 | A |
| 49 | 500 | A |
| 21 | 500 | A |
| 22 | 500 | A |
| 23 | 500 | A |
| 25 | 500 | A |
| 29 | 500 | C |
| 50 | 500 | A |
| 51 | 500 | C |
| 52 | 500 | A |
| 53 | 500 | A |
| 54 | 500 | A |
| 55 | 500 | A |
| 56 | 500 | A |
| 57 | 500 | A |

TABLE 9-continued

| Compound No. | Concentration (ppm) | Judgement |
|---|---|---|
| 58 | 500 | A |
| 59 | 500 | A |
| 60 | 500 | A |
| 61 | 500 | A |
| 62 | 500 | A |
| 65 | 500 | A |
| 66 | 500 | A |
| 67 | 500 | A |
| 68 | 500 | A |
| 69 | 500 | A |
| 70 | 500 | A |
| 72 | 500 | A |
| 73 | 500 | A |
| 74 | 500 | A |
| 75 | 500 | A |
| 76 | 500 | A |
| 77 | 500 | A |
| 78 | 500 | A |
| 79 | 500 | A |
| 80 | 500 | A |
| 81 | 500 | A |
| 82 | 500 | C |
| 83 | 500 | A |
| 84 | 500 | D |
| 85 | 500 | A |
| 86 | 500 | A |
| 87 | 500 | A |
| 88 | 500 | A |
| 89 | 500 | A |
| 90 | 500 | A |
| 92 | 500 | A |
| 93 | 500 | A |
| 94 | 500 | A |
| 95 | 500 | A |
| 96 | 500 | D |
| 97 | 500 | A |
| 98 | 500 | A |
| 99 | 500 | A |
| 100 | 500 | A |
| 101 | 500 | D |
| 103 | 500 | A |
| 104 | 500 | B |
| 105 | 500 | A |
| 106 | 500 | A |
| 107 | 500 | A |
| 108 | 500 | A |
| 109 | 500 | A |
| 110 | 500 | B |
| 111 | 500 | A |
| 112 | 500 | A |
| 113 | 500 | A |
| 114 | 500 | B |
| 115 | 500 | A |
| 116 | 500 | A |
| 117 | 500 | A |
| 118 | 500 | A |
| 119 | 500 | A |
| 120 | 500 | A |
| 121 | 500 | A |
| 122 | 500 | A |
| 123 | 500 | A |
| 124 | 500 | A |
| 125 | 500 | A |
| 126 | 500 | A |
| 127 | 500 | A |
| 128 | 500 | A |
| 129 | 500 | A |
| 130 | 500 | A |
| 131 | 500 | A |
| 132 | 500 | A |
| 133 | 500 | A |
| 134 | 500 | A |
| 135 | 500 | A |
| 136 | 500 | A |
| 137 | 500 | A |
| 138 | 500 | A |
| 139 | 500 | A |
| 140 | 500 | A |
| 141 | 500 | D |
| 142 | 500 | A |
| 143 | 500 | A |
| 144 | 500 | A |
| 145 | 500 | A |
| 147 | 500 | A |
| 148 | 500 | C |
| 150 | 500 | C |
| 152 | 500 | C |
| 154 | 500 | A |
| 155 | 500 | A |
| 156 | 500 | A |
| 157 | 500 | A |
| 158 | 500 | A |
| 159 | 500 | A |
| 160 | 500 | A |
| 161 | 500 | A |
| 162 | 500 | A |
| 163 | 500 | A |
| 164 | 500 | A |
| 165 | 500 | A |
| 166 | 500 | A |
| 167 | 500 | A |
| 168 | 500 | A |
| 169 | 500 | A |
| 170 | 500 | A |
| 171 | 500 | A |
| 172 | 500 | A |
| 173 | 500 | A |
| 174 | 500 | A |
| 175 | 500 | A |
| 176 | 500 | A |
| 177 | 500 | A |
| 178 | 500 | A |
| 179 | 500 | A |
| 180 | 500 | A |
| 181 | 500 | A |
| 182 | 500 | D |
| 183 | 500 | A |
| 184 | 500 | A |
| 185 | 500 | A |
| 186 | 500 | A |
| 187 | 500 | A |
| 188 | 500 | A |
| 189 | 500 | D |
| 190 | 500 | A |
| 191 | 500 | C |
| 192 | 500 | D |
| 193 | 500 | A |
| 195 | 500 | A |
| 196 | 500 | A |
| 197 | 500 | A |
| 198 | 500 | A |
| 199 | 500 | A |
| 200 | 500 | A |
| 201 | 500 | A |
| 202 | 500 | A |
| 203 | 500 | A |
| 204 | 500 | A |
| 205 | 500 | A |
| 206 | 500 | A |
| 207 | 500 | A |
| 208 | 500 | A |
| 209 | 500 | A |
| 210 | 500 | A |
| 211 | 500 | A |
| 213 | 500 | D |
| 214 | 500 | A |
| 215 | 500 | A |
| 216 | 500 | A |
| 217 | 500 | A |
| 218 | 500 | A |
| 219 | 500 | A |
| 220 | 500 | A |

TABLE 9-continued

| Compound No. | Concentration (ppm) | Judgement |
|---|---|---|
| 222 | 500 | A |
| 223 | 500 | A |
| 224 | 500 | A |
| 225 | 500 | A |
| 226 | 500 | A |
| 227 | 500 | A |
| 228 | 500 | A |
| 229 | 500 | A |
| 230 | 500 | A |
| 231 | 500 | A |
| 232 | 500 | A |
| 233 | 500 | A |
| 234 | 500 | A |
| 235 | 500 | A |
| 236 | 500 | A |
| 237 | 500 | A |
| 238 | 500 | A |
| 239 | 500 | A |
| 240 | 500 | A |
| 241 | 500 | A |
| 242 | 500 | A |
| 243 | 500 | A |
| 244 | 500 | A |
| 245 | 500 | B |
| 246 | 500 | A |
| 247 | 500 | A |
| 248 | 500 | A |
| 249 | 500 | A |
| 250 | 500 | A |
| 251 | 500 | A |
| 252 | 500 | A |
| 253 | 500 | A |
| 254 | 500 | A |
| 255 | 500 | A |
| 256 | 500 | A |
| 257 | 500 | A |
| 258 | 500 | A |
| 259 | 500 | C |
| 261 | 500 | B |
| 262 | 500 | A |
| 264 | 500 | A |
| 265 | 500 | A |
| 266 | 500 | A |
| 267 | 500 | C |
| 268 | 500 | A |
| 269 | 500 | A |
| 270 | 500 | A |
| 271 | 500 | A |
| 272 | 500 | A |
| 274 | 500 | A |
| 275 | 500 | D |
| 276 | 500 | A |
| 277 | 500 | A |
| 278 | 500 | A |
| 279 | 500 | A |
| 280 | 500 | A |
| 281 | 500 | A |
| 282 | 500 | B |
| 285 | 500 | A |
| 286 | 500 | A |
| 287 | 500 | A |
| 288 | 500 | A |
| 289 | 500 | A |
| 290 | 500 | A |
| 291 | 500 | A |
| 292 | 500 | A |
| 293 | 500 | A |
| 294 | 500 | D |
| 295 | 500 | D |
| 296 | 500 | A |
| 297 | 500 | A |
| 298 | 500 | A |
| 300 | 500 | A |
| 301 | 500 | A |
| 302 | 500 | D |
| 303 | 500 | A |
| 304 | 500 | A |
| 305 | 500 | D |
| 307 | 500 | A |
| 308 | 500 | A |
| 309 | 500 | A |
| 310 | 500 | A |
| 311 | 500 | A |
| 312 | 500 | A |
| 314 | 500 | A |
| 315 | 500 | A |
| 316 | 500 | A |
| 317 | 500 | A |
| 318 | 500 | A |
| 319 | 500 | D |
| 320 | 500 | D |
| 321 | 500 | A |
| 322 | 500 | A |
| 323 | 500 | A |
| 324 | 500 | A |
| 325 | 500 | A |
| 326 | 500 | A |
| 327 | 500 | A |
| 328 | 500 | A |
| 329 | 500 | C |
| 330 | 500 | D |
| 332 | 500 | A |
| 333 | 500 | A |
| 334 | 500 | A |
| 335 | 500 | A |
| 336 | 500 | A |
| 337 | 500 | A |
| 338 | 500 | A |
| 341 | 500 | C |
| 343 | 500 | A |
| 344 | 500 | A |
| 345 | 500 | B |
| 349 | 500 | A |
| 350 | 500 | A |
| 352 | 500 | A |
| 354 | 500 | A |
| 356 | 500 | A |
| 357 | 500 | A |
| 359 | 500 | A |
| 360 | 500 | A |
| 361 | 500 | A |
| 362 | 500 | A |
| 363 | 500 | A |
| 364 | 500 | A |
| 365 | 500 | A |
| 366 | 500 | A |
| 367 | 500 | A |
| 368 | 500 | A |
| 369 | 500 | A |
| 370 | 500 | A |
| 371 | 500 | B |
| 372 | 500 | A |
| 373 | 500 | A |
| 374 | 500 | A |
| 375 | 500 | A |
| 376 | 500 | A |
| 377 | 500 | A |
| 378 | 500 | A |
| 379 | 500 | A |
| 380 | 500 | A |
| 381 | 500 | A |
| 382 | 500 | A |
| 384 | 500 | A |
| 386 | 500 | A |
| 387 | 500 | A |
| 388 | 500 | A |
| 389 | 500 | A |
| 390 | 500 | A |
| 391 | 500 | A |
| 392 | 500 | A |
| 393 | 500 | A |
| 394 | 500 | A |

TABLE 9-continued

| Compound No. | Concentration (ppm) | Judgement |
|---|---|---|
| 395 | 500 | A |
| 396 | 500 | A |
| 397 | 500 | A |
| 398 | 500 | A |
| 399 | 500 | A |
| 401 | 500 | A |
| 403 | 500 | A |
| 405 | 500 | C |
| 406 | 500 | A |
| 407 | 500 | A |
| 408 | 500 | A |
| 409 | 500 | C |
| 410 | 500 | B |
| 411 | 500 | A |
| 412 | 500 | D |
| 413 | 500 | A |
| 414 | 500 | B |
| 415 | 500 | B |
| 416 | 500 | A |
| 418 | 500 | A |
| 419 | 500 | A |
| 420 | 500 | A |
| 421 | 500 | A |
| 422 | 500 | A |
| 423 | 500 | A |
| 424 | 500 | A |
| 425 | 500 | A |
| 426 | 500 | A |
| 427 | 500 | B |
| 428 | 500 | A |
| 429 | 500 | A |
| 430 | 500 | A |
| 431 | 500 | A |
| 432 | 500 | A |
| 433 | 500 | D |
| 434 | 500 | B |
| 436 | 500 | B |
| 437 | 500 | B |
| 438 | 500 | B |
| 440 | 500 | A |
| 441 | 500 | A |
| 442 | 500 | D |
| 443 | 500 | A |
| 444 | 500 | A |
| 445 | 500 | A |
| 446 | 500 | A |
| 447 | 500 | A |
| 448 | 500 | A |
| 449 | 500 | A |

Test Example 2

Insecticidal effect on adult maize weevil (*Sitophilus zeamais*)

Brown rice grains were immersed for about 30 seconds in a liquid chemical prepared by diluting a preparation containing each compound of the present invention as an active ingredient to adjust the concentration to 200 ppm.

After air-drying, it was placed in a glass Petri dish with a diameter of 4 cm and inoculated with adult maize weevil, after which the dish was closed and then allowed to stand in a room thermostated at 25%.

Eight days after the inoculation, the dead and alive were counted. The mortality was calculated in the same manner as in Test Example 1 and the insecticidal effect was judged according to the criterion shown in Test Example 1.

The test was carried out with triplicate groups of 10 insects.

The results obtained are shown in Table 10.

TABLE 10

| Compound No. | Concentration (ppm) | Judgement | Compound No. | Concentration (ppm) | Judgement |
|---|---|---|---|---|---|
| 5 | 200 | D | 29 | 200 | A |
| 10 | 200 | A | 30 | 200 | A |
| 12 | 200 | A | 31 | 200 | A |
| 14 | 200 | A | 32 | 200 | A |
| 17 | 200 | A | 33 | 200 | A |
| 18 | 200 | A | 34 | 200 | A |
| 21 | 200 | C | 36 | 200 | A |
| 22 | 200 | C | 37 | 200 | B |
| 24 | 200 | D | 39 | 200 | C |
| 25 | 200 | C | 45 | 200 | A |
| 27 | 200 | A | 47 | 200 | A |
| 28 | 200 | A | 49 | 200 | A |
| 50 | 200 | A | 80 | 200 | A |
| 53 | 200 | A | 82 | 200 | D |
| 54 | 200 | A | 85 | 200 | A |
| 56 | 200 | A | 86 | 200 | A |
| 57 | 200 | C | 87 | 200 | A |
| 58 | 200 | A | 88 | 200 | C |
| 59 | 200 | A | 89 | 200 | A |
| 60 | 200 | A | 90 | 200 | A |
| 62 | 200 | A | 92 | 200 | A |
| 65 | 200 | A | 93 | 200 | A |
| 66 | 200 | A | 94 | 200 | A |
| 67 | 200 | A | 95 | 200 | A |
| 68 | 200 | A | 96 | 200 | A |
| 69 | 200 | A | 97 | 200 | A |
| 73 | 200 | A | 98 | 200 | A |
| 74 | 200 | A | 99 | 200 | A |
| 75 | 200 | A | 100 | 200 | A |
| 76 | 200 | A | 101 | 200 | A |
| 77 | 200 | A | 104 | 200 | A |
| 78 | 200 | C | 105 | 200 | D |
| 79 | 200 | A | 106 | 200 | A |
| 108 | 200 | A | 139 | 200 | A |
| 109 | 200 | A | 141 | 200 | A |
| 112 | 200 | C | 142 | 200 | A |
| 113 | 200 | C | 143 | 200 | A |
| 114 | 200 | A | 144 | 200 | A |
| 115 | 200 | A | 145 | 200 | A |
| 117 | 200 | D | 146 | 200 | C |
| 118 | 200 | A | 147 | 200 | C |
| 119 | 200 | A | 153 | 200 | D |
| 120 | 200 | C | 154 | 200 | A |
| 121 | 200 | C | 157 | 200 | A |
| 122 | 200 | C | 158 | 200 | A |
| 124 | 200 | A | 160 | 200 | A |
| 125 | 200 | A | 162 | 200 | A |
| 127 | 200 | C | 164 | 200 | A |
| 128 | 200 | A | 165 | 200 | A |
| 129 | 200 | A | 166 | 200 | A |
| 130 | 200 | C | 167 | 200 | C |
| 131 | 200 | A | 169 | 200 | A |
| 137 | 200 | A | 170 | 200 | A |
| 138 | 200 | C | 172 | 200 | C |
| 173 | 200 | D | 201 | 200 | A |
| 174 | 200 | A | 202 | 200 | A |
| 175 | 200 | A | 203 | 200 | A |
| 177 | 200 | A | 204 | 200 | A |
| 178 | 200 | A | 206 | 200 | A |
| 179 | 200 | A | 207 | 200 | A |
| 180 | 200 | C | 208 | 200 | A |
| 183 | 200 | A | 209 | 200 | A |
| 184 | 200 | A | 210 | 200 | C |
| 185 | 200 | A | 211 | 200 | A |
| 186 | 200 | A | 212 | 200 | A |
| 187 | 200 | C | 214 | 200 | A |
| 188 | 200 | D | 215 | 200 | A |
| 190 | 200 | A | 216 | 200 | A |
| 194 | 200 | A | 217 | 200 | A |
| 195 | 200 | A | 218 | 200 | A |
| 196 | 200 | C | 219 | 200 | A |
| 197 | 200 | A | 220 | 200 | A |
| 198 | 200 | A | 221 | 200 | A |
| 199 | 200 | A | 222 | 200 | A |

TABLE 10-continued

| Compound No. | Concentration (ppm) | Judgement | Compound No. | Concentration (ppm) | Judgement |
|---|---|---|---|---|---|
| 200 | 200 | A | 225 | 200 | A |
| 226 | 200 | A | 247 | 200 | A |
| 227 | 200 | A | 248 | 200 | A |
| 228 | 200 | A | 249 | 200 | A |
| 229 | 200 | A | 250 | 200 | A |
| 230 | 200 | A | 251 | 200 | A |
| 231 | 200 | A | 252 | 200 | A |
| 232 | 200 | A | 254 | 200 | C |
| 233 | 200 | A | 256 | 200 | A |
| 234 | 200 | A | 258 | 200 | A |
| 235 | 200 | A | 259 | 200 | A |
| 236 | 200 | C | 268 | 200 | A |
| 237 | 200 | A | 269 | 200 | A |
| 238 | 200 | C | 270 | 200 | A |
| 239 | 200 | A | 271 | 200 | A |
| 240 | 200 | A | 272 | 200 | A |
| 241 | 200 | A | 274 | 200 | D |
| 242 | 200 | A | 276 | 200 | A |
| 243 | 200 | A | 278 | 200 | A |
| 244 | 200 | A | 279 | 200 | A |
| 245 | 200 | A | 281 | 200 | C |
| 246 | 200 | A | 282 | 200 | A |
| 283 | 200 | D | 321 | 200 | A |
| 288 | 200 | A | 322 | 200 | A |
| 290 | 200 | D | 323 | 200 | A |
| 291 | 200 | A | 324 | 200 | D |
| 292 | 200 | A | 325 | 200 | A |
| 293 | 200 | A | 326 | 200 | A |
| 294 | 200 | C | 327 | 200 | A |
| 297 | 200 | A | 328 | 200 | A |
| 298 | 200 | A | 329 | 200 | A |
| 302 | 200 | C | 332 | 200 | A |
| 303 | 200 | A | 333 | 200 | A |
| 305 | 200 | C | 334 | 200 | A |
| 307 | 200 | C | 335 | 200 | D |
| 308 | 200 | D | 336 | 200 | A |
| 310 | 200 | A | 337 | 200 | A |
| 314 | 200 | A | 339 | 200 | A |
| 315 | 200 | D | 341 | 200 | A |
| 316 | 200 | A | 342 | 200 | A |
| 317 | 200 | A | 343 | 200 | A |
| 318 | 200 | A | 344 | 200 | A |
| 320 | 200 | C | 345 | 200 | A |
| 349 | 200 | A | 378 | 200 | A |
| 350 | 200 | A | 379 | 200 | A |
| 351 | 200 | D | 380 | 200 | A |
| 352 | 200 | C | 381 | 200 | A |
| 354 | 200 | A | 382 | 200 | A |
| 355 | 200 | A | 383 | 200 | A |
| 356 | 200 | A | 384 | 200 | C |
| 358 | 200 | C | 385 | 200 | D |
| 359 | 200 | A | 386 | 200 | A |
| 360 | 200 | A | 387 | 200 | A |
| 361 | 200 | A | 388 | 200 | A |
| 362 | 200 | A | 389 | 200 | A |
| 363 | 200 | A | 390 | 200 | A |
| 364 | 200 | C | 391 | 200 | A |
| 365 | 200 | A | 392 | 200 | A |
| 366 | 200 | A | 393 | 200 | A |
| 368 | 200 | A | 394 | 200 | A |
| 371 | 200 | A | 396 | 200 | A |
| 372 | 200 | A | 397 | 200 | A |
| 375 | 200 | D | 398 | 200 | A |
| 377 | 200 | A | 399 | 200 | D |
| 400 | 200 | A | 428 | 200 | D |
| 401 | 200 | A | 429 | 200 | A |
| 406 | 200 | D | 430 | 200 | A |
| 410 | 200 | C | 432 | 200 | A |
| 411 | 200 | A | 433 | 200 | D |
| 412 | 200 | A | 434 | 200 | A |
| 414 | 200 | A | 435 | 200 | C |
| 415 | 200 | A | 436 | 200 | A |
| 417 | 200 | A | 437 | 200 | A |
| 418 | 200 | A | 438 | 200 | A |
| 419 | 200 | A | 439 | 200 | A |
| 420 | 200 | C | 441 | 200 | A |
| 421 | 200 | A | 442 | 200 | A |
| 422 | 200 | A | 443 | 200 | A |
| 423 | 200 | A | 444 | 200 | A |
| 424 | 200 | A | 445 | 200 | A |
| 425 | 200 | A | 446 | 200 | A |
| 426 | 200 | A | 447 | 200 | A |
| 427 | 200 | A | 449 | 200 | A |

What is claimed is:

1. A hydrazine derivative represented by the formula (I):

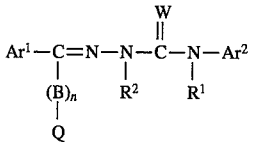

wherein, $Ar^1$ and $Ar^2$, which are the same or different, are unsubstituted phenyl groups; substituted phenyl groups having 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which are the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which are the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups; unsubstituted pyridyl groups having 1 to 3 heteroatoms which are the same or different and are selected from the group consisting of nitrogen atom, oxygen atom and sulfur atom; or substituted 5- or 6-membered heteroaryl groups which are the same as the above unsubstituted 5- or 6-membered heteroaryl groups, except for having as the substituent(s) one or more halogen atoms or $(C_{1-6})$alkyl groups, which are the same or different, $R^1$ and $R^2$, which are the same or different, are hydrogen atoms, $(C_{1-6})$alkyl groups, $(C_{2-6})$alkenyl groups or $(C_{2-6})$-alkynyl groups, B is an unsubstituted and linear or branched $(C_{1-6})$alkylene group, or the cycloalkylene group having 3 to 7 carbon atoms by bonding of substituents on the same carbon atoms to each other, n is zero or 1, Q is $-CON(R^5)R^6$ (wherein $R^5$ is a hydrogen atom; a $(C_{1-6})$alkyl group; a $(C_{2-6})$alkenyl group; a $(C_{2-6})$alkynyl group; an unsubstituted phenyl group; or a substituted phenyl group having 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which are the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which are the same or different and are selected from the group consisting of halogen atoms, $(C_{1-6})$alkyl groups and halo$(C_{1-6})$alkyl groups, dioxy$(C_{1-6})$alkylene groups, and dioxyhalo$(C_{1-6})$alkylene groups, and $R^6$ is a hydrogen atom; a $(C_{1-6})$alkyl group; a halo$(C_{1-6})$alkyl group; a $(C_{2-6})$alkenyl group; a $(C_{2-6})$alkynyl group; a $(C_{1-6})$alkoxy$(C_{1-6})$alkyl group; a halo$(C_{1-6})$alkoxy$(C_{1-6})$alkyl group; a $(C_{1-6})$alkylthio$(C_{1-6})$alkyl group; a halo$(C_{1-6})$alkylthio$(C_{1-6})$alkyl group; a $(C_{1-6})$alkylsulfinyl$(C_{1-6})$alkyl group; a halo$(C_{1-6})$alkylsulfinyl$(C_{1-6})$alkyl group; a $(C_{1-6})$alkylsulfonyl$(C_{1-6})$alkyl group; a halo$(C_{1-6})$alkylsulfonyl$(C_{1-6})$alkyl group; a cyano$(C_{1-6})$alkyl group; a hydroxy$(C_{1-6})$alkyl group; a $(C_{3-6})$cycloalkyl group; a $(C_{3-6})$cycloalkyl$(C_{1-6})$alkyl group; a $(C_{1-6})$alkoxycarbonyl$(C_{1-6})$alkyl group; a $(C_{1-6})$alkylcarbonyl-$(C_{1-6})$alkyl group; a carbamoyl$(C_{1-6})$alkyl group; a substituted carbamoyl$(C_{1-6})$alkyl group having one or two substituents which are the same or different and are selected from $(C_{1-6})$alkyl groups; an unsubstituted amino$(C_{1-6})$alkyl group; or a substituted amino$(C_{1-6})$alkyl group having one or two substituents which are the same or different and are selected from the group consisting of $(C_{1-6})$alkyl groups and $(C_{1-6})$alkylcarbonyl groups;

$R^5$ and $R^6$ when taken together to represent a $(C_{4-6})$alkylene group containing between adjacent carbon atoms of the carbon chain, —O—, —S(O)$_m$— (wherein m is as defined above) and said alkylene group having one or more substituents which are the same or different and are selected from the group consisting of $(C_{1-6})$alkyl groups, $(C_{1-6})$alkoxycarbonyl groups and phenyl group, or —N($R^7$)— wherein $R^7$ is hydrogen atoms; formyl groups; cyano groups; $(C_{1-6})$alkyl groups; $(C_{2-6})$alkenyl groups; $(C_{2-6})$alkynyl groups; $(C_{1-6})$alkylcarbonyl groups; halo$(C_{1-6})$alkylcarbonyl groups; $(C_{1-6})$alkoxycarbonyl groups; halo$(C_{1-6})$alkoxycarbonyl groups; $(C_{3-6})$cycloalkylcarbonyl group; phenoxycarbonyl groups; $(C_{1-6})$alkylsulfonyl groups; unsubstituted carbamoyl groups; substituted carbamoyl groups having as the substituent(s) one or two $(C_{1-6})$alkyl groups which are the same or different; unsubstituted carbamoyl$(C_{1-6})$alkyl groups; substituted carbamoyl$(C_{1-6})$alkyl groups having as the substituent(s); one or two $(C_{1-6})$alkyl groups which are the same or different; unsubstituted thiocarbamoyl groups; substituted thiocarbamoyl groups having as the substituent(s) one or two $(C_{1-6})$alkyl groups which are the same or different; unsubstituted sulfamoyl groups; substituted sulfamoyl groups having as the substituent(s) one or two $(C_{1-6})$alkyl groups which are the same or different; unsubstituted $(C_{1-6})$alkoxycarboimidoyl groups; substituted $(C_{1-6})$alkoxycarboimidoyl groups having $(C_{1-6})$alkyl group as the substituent; unsubstituted $(C_{1-6})$alkylthiocarboimidoyl groups; substituted $(C_{1-6})$alkylthiocarboimidoyl groups having $(C_{1-6})$alkyl group as the substituent; unsubstituted phenyl groups; substituted phenyl groups having 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which are the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which are the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups; unsubstituted phenyl$(C_{1-6})$alkyl groups; substituted phenyl$(C_{1-6})$alkyl groups having on the ring 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which are the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which are the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups; unsubstituted phenylcarbamoyl groups; substituted phenylcarbamoyl groups having on the ring 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which are the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which are the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups; unsubstituted phenylcarbonyl groups; substituted phenylcarbonyl groups having on the ring 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which are the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which are the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups; unsubstituted phenylsulfonyl groups; or substituted phenylsulfonyl groups having on the ring 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which are the same or different and are selected from the group consisting of halogen atoms, $(C_{1-6})$alkyl groups and halo$(C_{1-6})$alkyl groups, unsubstituted pyridyloxy group, substituted pyridyloxy groups having 1 to 4 substituents which are the same or different and are selected from the group consisting of halogen atoms, $(C_{1-6})$alkyl groups and halo$(C_{1-6})$alkyl groups, dioxy$(C_{1-3})$alkylene groups, and dioxyhalo$(C_{1-3})$alkylene groups); and W is an oxygen atom or a sulfur atom.

2. A hydrazine derivative according to claim 1, wherein $Ar^1$ and $Ar^2$, which are the same or different, are unsubstituted phenyl groups; or substituted phenyl groups having 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkylsulfinyl groups, halo$(C_{1-6})$alkylsulfinyl groups, $(C_{1-6})$alkylsulfonyl groups, halo$(C_{1-6})$alkylsulfonyl groups, $(C_{1-6})$alkoxycarbonyl groups, unsubstituted phenoxy group, substituted phenoxy groups having 1 to 5 substituents which are the same or different and are selected from the group consisting of halogen atoms, $(C_{1-6})$alkyl groups and halo$(C_{1-6})$alkyl groups, unsubstituted pyridyloxy group, and substituted pyridyloxy groups having 1 to 4 substituents which are the same or different and are selected from the group consisting of halogen atoms, $(C_{1-6})$alkyl groups and halo$(C_{1-6})$alkyl groups;

$R^1$ and $R^2$, which are the same or different, are hydrogen atoms or $(C_{1-6})$alkyl groups, B is an unsubstituted and linear or branched $(C_{1-6})$alkylene group, which is formed by bonding of alkyl substituents on the same carbon atom of a branched alkylene group to each other, n is zero or 1, Q is

—CON($R^5$)$R^6$ (wherein $R^5$ is a hydrogen atom; a $(C_{1-6})$alkyl group; a $(C_{2-6})$ alkenyl group; a $(C_{2-6})$ alkynyl group; an unsubstituted phenyl group; or a substituted phenyl group having 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups and halo$(C_{1-6})$alkoxy groups, and $R^6$ is a hydrogen atom or a $(C_{1-6})$alkyl group, $R^5$ and $R^6$ when taken together to represent a $(C_{4-6})$alkylene group containing between adjacent carbon atoms of the carbon chain, —O— or —N($R^7$)— (wherein $R^7$ is hydrogen atoms; formyl groups; cyano groups; $(C_{1-6})$ alkyl groups; $(C_{2-6})$ alkenyl groups; $(C_{2-6})$ alkynyl groups; $(C_{2-6})$ alkylcarbonyl groups; halo$(C_{1-6})$ alkylcarbonyl groups; $(C_{1-6})$alkoxycarbonyl groups: halo$(C_{1-6})$alkoxycarbonyl groups; $(C_{3-6})$cycloalkylcarbonyl group; phenoxycarbonyl groups; $(C_{1-6})$alkylsulfonyl groups; unsubstituted carbamoyl groups; substituted carbamoyl groups having as the substituent(s) one or two $(C_{1-6})$alkyl groups which are the same or different; unsubstituted phenyl groups; substituted phenyl groups having 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups and halo$(C)$alkoxy groups; unsubstituted phenyl$(C_{1-6})$alkyl groups; substituted phenyl$(C_{1-6})$alkyl groups having on the ring 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups and halo$(C_{1-6})$alkoxy groups; unsubstituted phenylcarbamoyl groups; substituted phenylcarbamoyl groups having on the ring 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups and halo$(C_{1-6})$alkoxy groups; unsubstituted phenylcarbonyl groups; substituted phenylcarbonyl groups having on the ring 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups and halo$(C_{1-6})$alkoxy groups; unsubstituted phenylsulfonyl groups; or substituted phenylsulfonyl groups having on the ring 1 to 5 substituents which are the same or different and are selected from the group consisting of halogen atoms, cyano group, nitro group, $(C_{1-6})$alkyl groups, halo$(C_{1-6})$alkyl groups, $(C_{1-6})$alkoxy groups and halo$(C_{1-6})$alkoxy groups); and W is an oxygen atom or a sulfur atom.

3. An agricultural and horticultural insecticide comprising a hydrazine derivative set forth in claim 1 as an active ingredient in an insecticidally effective amount and an agriculturally, horticulturally or agriculturally and horticulturally, acceptable carrier.

4. An agricultural and horticultural insecticide comprising a hydrazine derivative set forth in claim 2 as an active ingredient in an insecticidally effective amount and an agriculturally, horticulturally or agriculturally and horticulturally, acceptable carrier.

* * * * *